US011473087B2

(12) United States Patent
Zeng et al.

(10) Patent No.: US 11,473,087 B2
(45) Date of Patent: Oct. 18, 2022

(54) FMRP AND CANCER TREATMENT

(71) Applicant: ECOLE POLYTECHNIQUE FEDERALE DE LAUSANNE (EPFL), Lausanne (CH)

(72) Inventors: Qiqun Zeng, Lausanne (CH); Douglas Hanahan, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 6 days.

(21) Appl. No.: 16/867,763

(22) Filed: May 6, 2020

(65) Prior Publication Data
US 2020/0354718 A1 Nov. 12, 2020

(30) Foreign Application Priority Data

May 7, 2019 (EP) .................................... 19172927

(51) Int. Cl.
*C12N 15/113* (2010.01)
*A61P 35/00* (2006.01)
*C07K 16/18* (2006.01)
*A61K 45/06* (2006.01)

(52) U.S. Cl.
CPC ............ *C12N 15/113* (2013.01); *A61P 35/00* (2018.01); *C07K 16/18* (2013.01); *A61K 45/06* (2013.01); *C12N 2310/14* (2013.01); *C12N 2310/141* (2013.01); *C12N 2310/20* (2017.05)

(58) Field of Classification Search
None
See application file for complete search history.

(56) References Cited

U.S. PATENT DOCUMENTS

| 8,629,120 B2 | 1/2014 | Gleicher et al. | |
| 2013/0012569 A1 | 1/2013 | Gleicher et al. | |
| 2013/0149297 A1* | 6/2013 | Bagni ................... | C07K 16/18 424/130.1 |

FOREIGN PATENT DOCUMENTS

| WO | 2009086202 A2 | 7/2009 |
| WO | 2012001178 A1 | 1/2012 |
| WO | 2019154884 A1 | 8/2019 |

OTHER PUBLICATIONS

Ernst et al. Nature Communications 8 1411, pp. 1-10 (Year: 2017).*
Daman, K. et al., "High-Throughput Screening to Identify Compounds That Increase Fragile X Mental Retardation Protein Expression in Neural Stem Cells Differentiated From Fragile X Syndrome Patient-Derived Induced Pluripotent Stem Cells: HTS Using an FMRP Assay and FXS . . . ", Stem Cells Translational Medicine, vol. 4, No. 7, May 21, 2015, 800-808.
Danae, C-M et al., "RNA-binding proteins as molecular links between cancer and neurodegeneration", Biogerontology, Kluwer, Amsterdam, NL, vol. 15, No. 6, Sep. 18, 2014, 587-610.
Gleicher, N. et al., "Absence of BRCA/FMR1 Correlations in Women with Ovarian Cancers", PLOS One, vol. 9, Issue 7, 2014, 1-8.
Hargadon, K. M. et al., "Immune checkpoint blockade therapy for cancer: An overview of FDA-approved irrmune checkpoint inhibitors", International Immunopharmacology, vol. 62, Jul. 2, 2018, 29-39.
Leanne, L. et al., "GKAP Acts as a Genetic Modulator of NMDAR Signaling to Govern Invasive Tumor Growth", Cancer Cell, Cell Press, US, vol. 33, No. 4, Mar. 29, 2018, 736.
Luca, R. et al., "The Fragile X Protein binds mRNAs involved in cancer progression and modulates metastasis formation", EMBO Molecular Medicine, vol. 5, No. 10, Sep. 16, 2013, 1523-1536.
Romano, G. et al., "New frontiers in oncology: Immune checkpoint inhibitors in combination therapy", Drugs of Today, vol. 53, No. 2, 2017, 103.
Weghofer, A. et al., "BRCA 1/2 Mutations Appear Embryo-Lethal Unless Rescued by Low (CGG n<26) FMR1 Sub-Genotypes: Explanation for the "BRCA Paradox"?", PLOS One, vol. 7, Issue 9, 2012, 1-7.
Zalfa, F. et al., "The fragile X mental retardation protein regulates tumor invasiveness-related pathways in melanoma cells", Cell Death & Disease, vol. 8, No. 11, Nov. 1, 2017, e3169-e3169.
Zhou, X. et al., "Fragile X mental retardation protein promotes astrocytoma proliferation via the MEK/ERK signaling pathway", Oncotarget, vol. 7, No. 46, Sep. 23, 2016, 75394-75406.
Bassell, G. J. et al., "Loss of Local mRNA Regulation Alters Synaptic Development and Function", Neuron, 60, DOI 10.1016/j. neuron.2008.10.004, Oct. 23, 2008, 201-214.
Brahmer, J. R. et al., "Safety and Activity of Anti-PD-L1 Antibody in Patients with Advanced Cancer", NE J. Med., 366, Jun. 28, 2012, 2455-2465.
Darnell, J. C. et al., "Kissing complex RNAs mediate interaction between the Fragile-X mental retardation protein KH2 domain and brain polyribosomes", Genes Dev., 19, http://www.genesdev.org/cgi/doi/10.1101/gad.1276805, 2005, 903-918.
Hassler, M. R. et al., "Comparison of partially and fully chemically-modified siRNA in conjugate-mediated delivery in vivo", Nucleic Acids Res., 46(5), doi: 10.1093/nar/gky037. PMID: 29432571, 2018, 2185-2196.
Ishizuka, et al., "Loss of ADAR1 in tumours overcomes resistance to immune checkpoint blockade", Nature, 565(7737), doi: 10.1038/s41586-018-0768-9, Jan. 3, 2019, 43-48.
Jeon, S. J. et al., "Cellular stress-induced up-regulation of FMRP promotes cell survival by modulating PI3K-Akt phosphorylation cascades", J. Biomed. Sci., 18(17), http://www.jbiomedsci.com/content/18/1/17, 2011, 17.
Li, L. et al., "Hijacking the neuronal NMDAR signaling circuit to promote tumor growth and invasion", Cell, 153, http://dx.doi.org/10.1016/j.cell.2013.02.051, Mar. 28, 2013, 86-100.

(Continued)

*Primary Examiner* — Brian Whiteman
(74) *Attorney, Agent, or Firm* — Elmore Patent Law Group, P.C.; Joseph C. Zucchero

(57) ABSTRACT

The present invention provides compositions and methods for down-modulating the expression and/or the immuno-suppressive activity of i) the FMRP protein, ii) an mRNA encoding the FMRP protein, and/or iii) the FMR1 gene for the treatment and/or prevention of primary cancer and/or cancer metastasis in a subject in need thereof.

13 Claims, 32 Drawing Sheets

Specification includes a Sequence Listing.

(56) References Cited

OTHER PUBLICATIONS

Mali, P. et al., "RNA-Guided Human Genome Engineering via Cas9", Science, 339(6121), doi:10.1126/science.1232033., Feb. 15, 2013, 823-826.

Roos, M. et al., "A Small-Molecule Inhibitor of Lin28", ACS Chem. Biol. 11(10), doi:10.1021/acschembio.6b00232., Aug. 22, 2016, 2773-2781.

Royal, R. E. et al., "Phase 2 trial of single agent Ipilimumab (anti-CTLA-4) for locally advanced or metastatic pancreatic adenocarcinoma", J. Immunother., 33, doi:10.1097/CJI.0b013e3181eec14c, Oct. 2010, 828-833.

Santoro, M. R. et al., "Molecular Mechanisms of Fragile X Syndrome: A Twenty-Year Perspective", Annu. Rev. Pathol. Mech. Dis., 7, doi:10.1146/annurev-pathol-011811-132457, 2012, 219-245.

Schoenfeld, et al., "Acquired Resistance to Immune Checkpoint Inhibitors", Cancer Cell, 37, https://doi.org/10.1016/j.ccell.2020.03.017, Apr. 13, 2020, 443-455.

Selvam, C. et al., "Therapeutic potential of chemically modified siRNA: Recent trends", Chem Biol Drug Des., 90(5), doi: 10.1111/cbdd.12993, Nov. 2017, 665-678.

Tran, et al., "Widespread RNA editing dysregulation in brains from autistic individuals", Nat. Neurosci., 22(1), doi: 10.1038/s41593-018-0287-x, Jan. 2019, 25-36.

Vasilyev, N. et al., "Crystal structure reveals specific recognition of a G-quadruplex RNA by a β-turn in the RGG motif of FMRP", PNAS, 112(39), doi: 10.1073/pnas.1515737112, Sep. 15, 2015, E5391-E5400.

Vuong, W. et al., "High-Throughput Screen for Inhibitors of Androgen Receptor-RUNX2 Transcriptional Regulation in Prostate Cancer", J. Pharmacol. Exp. Ther., 359(2), doi: 10.1124/jpet.116.234567, Nov. 2016, 256-261.

Zhang, H. et al., "Targeting CDK9 Reactivates Epigenetically Silenced Genes in Cancer", Cell, 175(5), doi: 10.1016/j.cell.2018.09.051, Nov. 15, 2018, 1244-1258.

\* cited by examiner

FMRP AND CANCER TREATMENT

RELATED APPLICATION

The present application claims the benefit of EP patent application serial number 19172927.6, filed on May 7, 2019, the contents of which are incorporated herein by reference in its entirety.

FIELD OF THE INVENTION

The present invention provides compositions and methods for modulating the expression and/or activity of i) the FMRP protein (hereinafter "FMRP"), ii) an mRNA encoding the FMRP and/or iii) the FMR1 gene that encodes FMRP for the treatment and/or prevention of cancer and/or cancer metastasis in a subject in need thereof.

BACKGROUND OF THE INVENTION

The discovery of immune checkpoint receptors and the development of checkpoint blockade-based immunotherapy is one of the most notable successes in basic research and clinical treatment for cancer, for it raised the possibility to cure some malignant tumors[1]. Immunomodulatory agents targeting T cell co-inhibitory immune checkpoints such as the programmed death-1 (PD-1) or its ligand (PD-L1), the cytotoxic T-lymphocyte antigen 4 (CTLA-4) have been approved for the treatment of different types of malignant tumors[1].

However, across the spectrum of human cancer types, a widely variable proportion (40-90%) of patients with different forms of cancer have little or no benefit from the well-known PD-1 or CTLA-4 blockade-based immunotherapy[2], notably including those with pancreatic ductal adenocarcinoma (PDAC)[3,4]. Thus, additional immunotherapeutic strategies are still urgently needed.

SUMMARY OF THE INVENTION

The present invention provides an agent capable of down-modulating the expression and/or the immuno-suppressive activity of i) the FMRP protein, ii) an mRNA encoding the FMRP protein, and/or iii) the FMR1 gene that encodes FMRP for use in the treatment and/or prevention of primary cancer and/or cancer metastasis in a subject in need thereof.

Also provided is a plasmid or a vector comprising one or more nucleic acid(s) encoding the miRNA, siRNA, piRNA, hnRNA, snRNA, esiRNA, shRNA, and/or antisense oligonucleotide of the invention.

Further provided is a host cell comprising a plasmid or vector of the invention or one or more nucleic acid(s) encoding the miRNA, siRNA, piRNA, hnRNA, snRNA, esiRNA, shRNA, and/or antisense oligonucleotide of the invention.

Also provided is a plasmid or a vector comprising one or more nucleic acid(s) encoding the peptide or analog thereof, an antibody or an antigen-binding fragment of said antibody, or antibody mimetic of the invention.

Further provided is a host cell comprising a plasmid or vector of the invention or one or more nucleic acid(s) encoding the peptide or analog thereof, an antibody or an antigen-binding fragment of said antibody, or antibody mimetic of the invention.

Further provided is a pharmaceutical composition comprising:
  i) a therapeutically effective amount of an agent capable of modulating the expression and/or activity of the FMRP protein, an mRNA encoding the FMRP and/or the FMR1 gene, or
  ii) a plasmid or a vector of the invention, or
  iii) a host cell of the invention,
and a pharmaceutically acceptable carrier or diluent.

Further provided is a pharmaceutical composition that targets FMRP for selective and efficient degradation comprising an agent as disclosed herein, wherein such agent is chemically linked to an E3-ubiquitin ligase. The agent binds tightly to the FMRP to form an FMRP-agent complex while the E3-ubiquitin ligase that directs the bound protein to the proteasome for degradation.

Also provided is a method of treatment and/or prevention of cancer and/or cancer metastasis in a subject in need thereof, comprising administering to said subject an agent of the invention.

Also provided is a method of treatment and/or prevention of cancer and/or cancer metastasis in a subject in need thereof, comprising administering to said subject a pharmaceutical composition of the invention.

Without wishing to be bound to any particular theory, it is believed that engineered upregulation in cells or tissues of the FMR1 gene (endogenous or via gene therapy) to produce FMRP protein at similar levels as in many tumors, or delivery of FMRP protein or FMR1 mRNA, could be a strategy to ameliorate autoimmune diseases such as Type 1 diabetes, et al, where there is chronic or otherwise inappropriate infiltration of CD8 (cytotoxic) T cells with pathological effects. Similarly, the success of cell therapies involving transplantation of stem and other cells could be enhanced if such cells were engineered to over-express FMRP, either stably (via lentivirus transduction or CRISPR/Cas9 genome editing), or transiently via AAV.

DESCRIPTION OF THE INVENTION

Figure 1A:
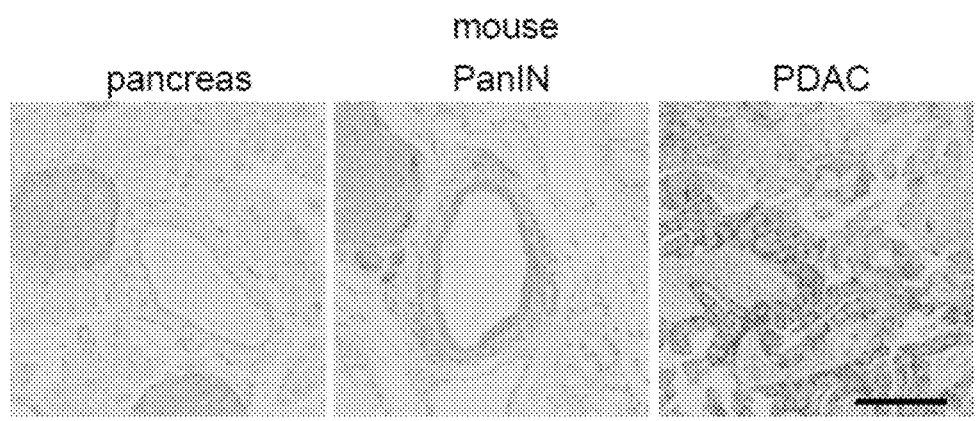
FIG. 1A-1J. Deletion of FMRP in mouse PDAC cancer cells strikingly prolongs overall survival and severely impairs tumor growth and metastasis in immunocompetent but not immuno-deficient mice. (A) Representative images and quantification of FMRP expression in mouse normal pancreas, premalignant PanIN lesions, and PDAC tumor tissues of P48-cre; LSL-KrasG12D; P53R172H/+ PDAC mouse model in the FVBN background. n=3 mice per group. Student T-test was used. Scale bar, 100 µm. Immunostaining of human PDAC tissue-microarrays (not shown) corroborates the results in mouse PDAC. (B) Expression of FMRP in a 'wild-type (WT)' mouse PDAC cell line (4361.12) and its absence in derivative FMRP deficient cells ('KO'), which are generated by transiently transfection of Cas9/SgRNA vectors targeting the mouse FMR1 gene that encodes FMRP, as revealed by western blotting using two different FMRP antibodies that recognize different epitopes of the FMRP protein (Abcam, ab191411; Cell signaling, 4317s). Three independent experiments. (C) Colony formation of 4361.12 WT2 and FMRP KO2 cells in culture. Indicated number of cancer cells were seeded into one well of a six-well plate. Ten days later, the cells were fixed and stained by crystal violet. Three independent experiments; (D) Schematic of the in vivo lung metastasis assay. In brief, 2×10^5 cells were injected into the tail vein of immunocompetent FVBN or immunodeficient SCID/Beige mice, which seeds cancer cells in the lung. Mice were monitored twice per week, and were sacrificed when reaching a veterinary endpoint. (E-F) Overall survival of syngeneic immunocompetent FVBn or immunodeficient SCID/Beige mice injected with murine PDAC WT2 or FMRP KO2 cells, n=5 mice per group, Kaplan-Meier test was used. (G) Expression of FMRP in mouse PDAC cell line 4361.12 WT cells and its absence in a second FMRP KO cell line (KO8), also generated by transiently transfection with Cas9/SgRNA vectors targeting the mouse FMR1 gene, as revealed by western blotting. Three independent experiments. (H) Schematic of the in vivo subcutaneous (s.c.) primary tumor growth model. In brief, $5\times10^5$ cells were s.c. injected under the skin of FVBN or NSG mice. Tumor-bearing mice were monitored twice per week, and sarcrified at day 25 after the injection, when WT tumor volume reaches 1000 mm^3. (I-J) Tumor weight from FVBn (I) or immunodeficient NSG (J) mice injected with murine PDAC WT (2 independent clones WT2 and WT3) or FMRP KO (2 independent clones KO2 and KO8) cells at day 28, n=4~10 mice per group, the unpaired T-test was used.
Figure 1A:
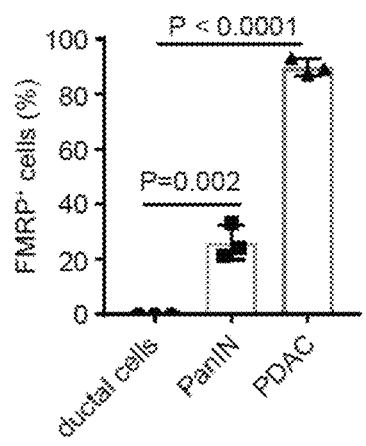

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise/comprising" is generally used in the sense of include/including, that is to say permitting the presence of one or more features or components.

As used in the specification and claims, the singular form "a", "an" and "the" include plural references unless the context clearly dictates otherwise.

As used herein, "at least one" means "one or more", "two or more", "three or more", etc.

As used herein the terms "subject"/"subject in need thereof", or "patient"/"patient in need thereof" are well-recognized in the art, and, are used interchangeably herein to refer to a mammal, including dog, cat, rat, mouse, monkey, cow, horse, goat, sheep, pig, camel, and, most preferably, a human. In some cases, the subject is a subject in need of treatment or a subject with a disease or disorder. However, in other aspects, the subject can be a normal subject. The term does not denote a particular age or sex. Thus, adult and newborn subjects, whether male or female, are intended to be covered. Preferably, the subject is a human. Most preferably a human suffering from of cancer and/or cancer metastasis or a human that might be at risk of suffering from cancer and/or cancer metastasis.

The terms "nucleic acid", "polynucleotide," and "oligonucleotide" are used interchangeably and refer to any kind of deoxyribonucleotide (e.g. DNA, cDNA, . . . ) or ribonucleotide (e.g. RNA, mRNA, . . . ) polymer or a combination of deoxyribonucleotide and ribonucleotide (e.g. DNA/RNA) polymer, in linear or circular conformation, and in either single—or double—stranded form. These terms are not to be construed as limiting with respect to the length of a polymer and can encompass known analogues of natural nucleotides, as well as nucleotides that are modified in the base, sugar and/or phosphate moieties (e.g. phosphorothioate backbones). In general, an analogue of a particular nucleotide has the same base-pairing specificity, i.e., an analogue of A will base-pair with T.

The term "vector", as used herein, refers to a viral vector or to a nucleic acid (DNA or RNA) molecule such as a plasmid or other vehicle, which contains one or more heterologous nucleic acid sequence(s) of the invention and, preferably, is designed for transfer between different host cells. The terms "expression vector", "gene delivery vector" and "gene therapy vector" refer to any vector that is effective to incorporate and express one or more nucleic acid(s) of the invention, in a cell, preferably under the regulation of a promoter. A cloning or expression vector may comprise additional elements, for example, regulatory and/or post-transcriptional regulatory elements in addition to a promoter.

The term "about," particularly in reference to a given quantity, is meant to encompass deviations of plus or minus ten (10) percent.

While focusing on the role of FMRP in promoting the invasive growth of pancreatic neuroendocrine and ductal cancer[5], the Inventors surprisingly discovered the unexpected and unprecedented role of FMRP in suppressing anti-tumor immunity in vivo.

The fragile X mental retardation protein (FMRP), an RNA-binding protein that is highly expressed in the brain, binds to a subset of specific mRNAs of synaptic (and other) proteins and regulates their translation in neurons[6]. Due to the critical role of FMRP in synaptic function, the lack of its expression leads to the fragile X syndrome (FXS), the most common form of inherited intellectual disabilities and one main cause of autism[7]. Different from this role, other studies of FMRP have revealed it to be expressed in several types of cancer[8,9], and have implicated it in cancer cell survival, invasion, and metastasis. The term FMRP also refers to FMRP isoforms in the present disclosure.

The inventors have shown that the absence of the FMRP expression in mouse pancreatic ductal adenocarcinoma cells (PDAC) and colon carcinoma cells strikingly prolongs overall survival and severely impairs tumor growth in syngeneic immunocompetent mice.

The present invention thus provides an agent capable of modulating the expression and/or activity of i) the FMRP protein, ii) an mRNA encoding the FMRP and/or iii) the FMR1 gene for use in the treatment and/or prevention of cancer and/or cancer metastasis in a subject in need thereof.

Preferably, the modulation of the expression and/or activity of the FMRP protein includes the regulatory interactions of the FMRP protein with its mRNA and miRNA targets (through, e.g., its RNA-binding domains), and/or with other proteins.

In certain embodiments, the modulation is a reduction in FMRP mRNA level. In certain embodiments, the modulation is a reduction in FMRP protein level and/or activity. In certain embodiments, both FMRP mRNA and protein levels are reduced. Such reduction may occur in a time-dependent or in a dose-dependent manner.

As used herein, "inhibition" or "reduction" are used interchangeably to mean a reduction of target nucleic acid levels or target protein levels in the presence of an agent of the invention compared to target nucleic acid levels or target protein levels in the absence of the agent of the invention.

In one aspect, the agent of the invention inhibits the translation of an RNA encoding FMRP.

In another aspect, the agent of the invention inhibits the transcription of a DNA encoding FMRP.

In a further aspect, the agent inhibits or impairs the binding of the FMRP to a target mRNA, and/or the agent inhibits or impairs the binding of FMRP to its interacting proteins or other molecules via which it transmits its immune-suppressive activity.

Preferably, the cancer and/or cancer metastasis to be treated is resistant to immunotherapy and is selected from the non-limiting examples of cancers including carcinoma, blastoma, sarcoma, melanoma, lymphoma, and leukemia or lymphoid malignancies. More particular examples of such cancers include breast cancer, colon cancer, rectal cancer, colorectal cancer, kidney or renal cancer, clear cell cancer lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, prostatic neoplasms, liver cancer, bladder cancer, cancer of the peritoneum, hepatocellular cancer, gastric or stomach cancer including gastrointestinal cancer, gastrointestinal stromal tumor, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma, myelodysplasia disorders, myeloproliferative disorders, chronic myelogenous leukemia, and acute hematologic malignancies, endometrial or uterine carcinoma, endometriosis, endometrial stromal sarcoma, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, mast cell sarcoma, ovarian sarcoma, uterine sarcoma, melanoma, malignant mesothelioma, skin carcinomas, Schwannoma, oligodendroglioma, neuroblastomas, neuroectodermal tumor, rhabdomyosarcoma, osteogenic sarcoma, leiomyosarcomas, Ewing Sarcoma, peripheral primitive neuroectodermal tumor, urinary tract carcinomas, thyroid carcinomas, Wilm's tumor, as well as abnormal vascular proliferation associated with phakomatoses, edema (such as that associated with brain tumors), and Meigs' syndrome.

Usually, the agent of the invention is a chemical compound, a peptide or analog thereof, a nucleic acid, an antibody, an antigen-binding fragment of said antibody or antibody mimetic. Preferably, the agent is able to access the intracellular compartments of cancer cells, given the predominant subcellular localization of FMRP in the cytoplasm.

As used herein, a "chemical agent or compound" is a compound that produces change by virtue of its chemical composition and its effects on living tissues and organisms. The chemical agent may be a small molecule inhibitor (SMI), a nucleic acid—e.g. a siRNA—or a peptide. In embodiments, the chemical compound is preferably a non-peptidyl molecule. Most preferably, the non-peptidyl molecule is inducing selective intracellular proteolysis of a peptide encoded by a nucleic acid sequence of the invention. Examples of chemical compounds inducing selective intracellular proteolysis comprise proteolysis targeting chimera (PROTAC) protein degraders and small-molecule chemical modulators of deubiquitinating enzymes upstream of or on the proteasome. As known in the art, PROTACs, also known as Active Degraders, are heterobifunctional small molecules composed of two active domains and a linker capable of removing specific unwanted proteins.

Compositions of matter that inhibit FMRP and thus recapitulate the invention revealed by gene knockout can be discovered and validated using a number of techniques and methodologies known to those of skill in the art. The following are illustrative of the spectrum of approaches that can be used to identify FMRP inhibitors with potential for therapeutic development of anti-cancer drugs.

In case the agent is a peptide, then it will preferably be conjugated to an agent that increases the accumulation of the peptide in the cancer cell. Such an agent can be a compound which induces receptor mediated endocytosis such as for example the membrane transferrin receptor mediated endocytosis of transferrin conjugated to therapeutic drugs (Qian Z. M. et al., "Targeted drug delivery via the transferrin receptor-mediated endocytosis pathway" Pharmacological Reviews, 54, 561, 2002) or a cell membrane permeable carrier which can, be selected e.g. among the group of fatty acids such as decanoic acid, myristic acid and stearic acid, which have already been used for intracellular delivery of peptide inhibitors of protein kinase C (Ioannides C. G. et al., "Inhibition of IL-2 receptor induction and IL-2 production in the human leukemic cell line Jurkat by a novel peptide inhibitor of protein kinase C" Cell Immunol., 131, 242, 1990) and protein-tyrosine phosphatase (Kole H.K. et al., "A peptide-based protein-tyrosine phosphatase inhibitor specifically enhances insulin receptor function in intact cells" J. Biol. Chem. 271, 14302, 1996) or among peptides. Preferably, cell membrane permeable carriers are used. More preferably a cell membrane permeable carrier peptide is used.

In case the cell membrane permeable carrier is a peptide then it will preferably be a positively charged amino acid rich peptide.

Preferably such positively charged amino acid rich peptide is an arginine rich peptide. It has been shown in Futaki et al. (Futaki S. et al., "Arginine-rich peptides. An abundant source of membrane-permeable peptides having potential as carriers for intracellular protein delivery" J. Biol. Chem., 276, 5836, 2001), that the number of arginine residues in a cell membrane permeable carrier peptide has a significant influence on the method of internalization and that there seems to be an optimal number of arginine residues for the internalization, preferably they contain more than 6 arginines, more preferably they contain 9 arginines (R9).

The peptide may be conjugated to the cell membrane permeable carrier by a spacer (e.g. two glycine residues). Any cell membrane permeable carrier can be used as determined by the skilled artisan. In this case, the cell membrane permeable carrier is preferably a peptide.

Usually arginine rich peptides are selected from the non-limiting group comprising the HIV-TAT 48-57 peptide (GRKKRRQRRR; SEQ ID NO. 14), the FHV-coat 35-49 peptide (RRRRNRTRRNRRRVR; SEQ ID NO. 15), the HTLV-II Rex 4-16 peptide (TRRQRTRRARRNR; SEQ ID NO. 16) and the BMV gag 7-25 peptide (KMTRAQRRAAARRNRWTAR)(SEQ ID NO. 17).

Since an inherent problem with native peptides (in L-form) is degradation by natural proteases, the peptide, as well as the cell membrane permeable peptide, of the invention may be prepared to include D-forms and/or "retro-inverso isomers" of the peptide. In this case, retro-inverso isomers of fragments and variants of the peptide, as well as of the cell membrane permeable peptide, of the invention are prepared.

In case the agent is a nucleic acid, then it is selected from the group comprising a nucleic acid encoding an miRNA, an siRNA, a piRNA, an hnRNA, an snRNA, an sg RNA, an esiRNA, an shRNA, and an antisense oligonucleotide (e.g. modified ASO), or a combination thereof.

When the agent is a nucleic acid, the agent can be prepared by any suitable art recognized method such as phosphoramidite or H-phosphonate chemistry, which can be carried out manually or by an automated synthesizer. The nucleic acid based agents of the invention may also be modified in a number of ways without compromising their ability to hybridize to their target (see e.g., Agrawal and Gait, Advances in Nucleic Acid Therapeutics, (2019) doi.org/10.1039/9781788015714).

In embodiments wherein the agent is an miRNA, siRNA, piRNA, hnRNA, snRNA, sgRNA, esiRNA, shRNA, or antisense compound the agent is targeted to a human FMRP nucleic acid. Nucleotide sequences that encode human FMRP include, without limitation, the following: GENBANK Accession No. NM_001185075.1 (incorporated herein as SEQ ID NO: 1); GENBANK Accession No. NM_001185076.1 (incorporated herein as SEQ ID NO: 2), GENBANK Accession No. NM_001185081.2 (incorporated herein as SEQ ID NO: 3); GENBANK Accession No. NM_001185082.2 (incorporated herein as SEQ ID NO: 4); and GENBANK Accession No. NM_002024.6 (incorporated herein as SEQ ID NO: 5).

Nucleotide sequences that encode murine (mouse) FMRP include, without limitation, the following: GENBANK Accession No. NM_001290424.1 (incorporated herein as SEQ ID NO: 6); GENBANK Accession No. NM_001374719.1 (incorporated herein as SEQ ID NO: 7), and GENBANK Accession No. NM_008031.3 (incorporated herein as SEQ ID NO: 8).

The terms "microRNA," "miRNA," and "MiR" are interchangeable and refer to endogenous or artificial non-coding RNAs that are capable of regulating gene expression. It is believed that miRNAs function via RNA interference. The design of such microRNAs is within the skill of ordinary artisans.

The terms "siRNA" and "short interfering RNA" are interchangeable and refer to single-stranded or double-stranded RNA molecules that are capable of inducing RNA interference. siRNA molecules typically have a duplex region that is between 18 and 30 base pairs in length. The design of such siRNAs is within the skill of ordinary artisans.

The terms "piRNA" and "Piwi-interacting RNA" are interchangeable and refer to a class of small RNAs involved in gene silencing. PiRNA molecules typically are between 26 and 31 nucleotides in length. The design of such PiRNAs is within the skill of ordinary artisans. Examples of modified antisense oligonucleotides (ASOs) include the GapmeRs. As used herein, a GapmeR is a chimeric antisense oligonucleotide that contains a central block of deoxynucleotide monomers sufficiently long to induce RNase H cleavage. Usually, the GapmeRs of the invention are directed against one or more mRNA encoding the FMRP or a target mRNA. The design of such GapmeRs is within the skill of ordinary artisans.

The terms "sgRNA" and "guideRNA" are interchangeable and refer to a specific RNA sequence that recognizes the target DNA region of interest and directs the endonuclease there for editing. The gRNA is usually made up of two parts: crispr RNA (crRNA), a 17-20 nucleotide sequence complementary to the target DNA, and a tracr RNA, which serves as a binding scaffold for the Cas nuclease.

Any suitable engineered sgRNA, or crRNA and tracrRNA, can be employed as long as it is effective for recognizing a target DNA of the invention. The design of such sgRNA, or crRNA and tracrRNA is within the skill of ordinary artisans. The sgRNA can, e.g., be directed to recognize the FMR1 DNA, for example, an sgRNA selected from the group comprising 5'-GTGGAAGTGCGGGGCTC-CAA-3' (SEQ ID NO: 12) and 5'-GAGCTGGTGGTG-GAAGTGCG-3 (SEQ ID NO: 13), or a combination thereof.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs. The design of such snRNA is within the skill of ordinary artisans.

In particular, the invention therefore provides isolated siRNA comprising short double-stranded RNA from about 18 to about 30 nucleotides in length, that are targeted to the mRNA encoding the FMRP or the target mRNA. The term "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered. The siRNAs of the invention can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the invention can also comprise a 3' overhang. A "3' overhang" refers to at least one unpaired nucleotide extending from the 3'-end of an RNA strand. Thus, in one aspect, the siRNA of the invention comprises at least one 3' overhang of from one to about six nucleotides (which includes ribonucleotides or deoxynucleotides) in length, preferably from one to about five nucleotides in length, more preferably from one to about four nucleotides in length, and particularly preferably from about one to about two nucleotides in length.

In the case both strands of the siRNA molecule comprise a 3' overhang, the length of the overhangs can be the same or different for each strand. In a most preferred embodiment, the 3' overhang is present on both strands of the siRNA and is two nucleotides in length. In order to enhance the stability of the present siRNAs, the 3' overhangs can also be stabilized against degradation. In one embodiment, the overhangs are stabilized by including purine nucleotides, such as adenosine or guanosine nucleotides.

Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

The siRNAs of the invention can be targeted to any stretch of approximately 18-30, preferably 19-25 contiguous nucleotides in any of the target mRNA sequences (including the mRNA encoding the FMRP). Techniques for selecting target sequences for siRNA are well known in the art. Thus, the sense strand of the present siRNA comprises a nucleotide sequence identical to any contiguous stretch of about 18 to about 30 nucleotides in the target mRNA.

The siRNAs of the invention can be obtained using a number of techniques known to those of skill in the art. For example, the siRNAs can be chemically synthesized or recombinantly produced using methods known in the art. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Qiagen (Hilden, Germany) and Cruachem (Glasgow, UK).

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment. The siRNA expressed from recombinant plasmids either can be isolated from cultured cell expression systems by standard techniques or can be expressed intracellularly in neurons.

The siRNAs of the invention can also be expressed from recombinant viral vectors intracellularly in neurons. The recombinant viral vectors comprise sequences encoding the siRNAs of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in the brain (e.g., in hippocampal neurons), in the prostate, etc. . . .

In one embodiment, the one or more siRNA of the invention is selected from the non-limiting group comprising siRNA targeting human FMRP (S5317, S5316) from Thermo Scientific.

In one embodiment, the one or more siRNA of the invention is selected from the non-limiting group consisting of siFMRP#1: AUAAG AGACA ACUUG GUGC (SEQ ID NO: 10); and siFMRP#2: UAACUUCGGAAUUAUGUAG (SEQ ID NO: 11).

The agent of the invention may also be selected from an antibody, an antigen-binding fragment of said antibody, or an antibody mimetic. Preferably, when the agent is an antibody, an antigen-binding fragment of said antibody, or an antibody mimetic, it is in the form of a plasmid or a vector comprising one or more nucleic acid(s) encoding the antibody, antigen-binding fragment of said antibody, or antibody mimetic, such that it can be delivered inside the cancer cell, where FMRP is localized in the cytoplasm and the nucleus.

As used herein, an "antibody" is a protein molecule that reacts with a specific antigenic determinant or epitope and belongs to one or five distinct classes based on structural properties: IgA, IgD, IgE, IgG and IgM. The antibody may be a polyclonal (e.g. a polyclonal serum) or a monoclonal antibody, including but not limited to fully assembled antibody, single chain antibody, antibody fragment, and chimeric antibody, humanized antibody as long as these molecules are still biologically active and still bind to at least one peptide of the invention. Preferably the antibody is a monoclonal antibody. Preferably also the monoclonal antibody will be selected from the group comprising the IgG1, IgG2, IgG2a, IgG2b, IgG3 and IgG4 or a combination thereof. Most preferably, the monoclonal antibody is selected from the group comprising the IgG1, IgG2, IgG2a, and IgG2b, or a combination thereof.

A typical antibody is composed of two immunoglobulin (Ig) heavy chains and two Ig light chains. Several different types of heavy chain exist that define the class or isotype of an antibody. These heavy chain types vary between different animals. All heavy chains contain a series of immunoglobulin domains, usually with one variable (VH) domain that is important for binding antigen and several constant (CH) domains. Each light chain is composed of two tandem immunoglobulin domains: one constant (CL) domain and one variable domain (VL) that is important for antigen binding.

For the production of antibodies, various host animals may be immunized by injection with the FMRP gene product, or a portion thereof including, but not limited to, portions of the FMRP gene product in a recombinant protein. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and corynebacterium parvum.

Monoclonal antibodies may be prepared by using any technique which provides for the production of antibody molecules by continuous cell lines in culture. These include but are not limited to the hybridoma technique originally described by Kohler and Milstein, 1975, Nature, 256:495-497, the human B-cell hybridoma technique (Kosbor et al., 1983, Immunology Today, 4:72, Cote et al., 1983, Proc. Natl. Acad. Sci., 80:2026-2030) and the EBV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to one of the binding partners.

The term "isolated", when used as a modifier of an antibody of the invention means that the antibody is made by the hand of man or is separated, completely or at least in part, from their naturally occurring in vivo environment. Generally, isolated antibodies are substantially free of one or more materials with which they normally associate with in nature, for example, one or more protein. The term "isolated" does not exclude alternative physical forms of the antibodies, such as multimers/oligomers, modifications (e.g., phosphorylation, glycosylation, lipidation) or derivatized forms, or forms expressed in host cells produced by the hand of man.

An "isolated" antibody can also be "substantially pure" or "purified" when free of most or all of the materials with which it typically associates with in nature. Thus, an isolated antibody that also is substantially pure or purified does not include polypeptides or polynucleotides present among millions of other sequences, such as antibodies of an antibody library or nucleic acids in a genomic or cDNA library.

Antibody fragments which recognize specific epitopes may be generated by known techniques. An "antigen binding fragment" comprises a portion of a full-length antibody. Examples of antigen binding fragments include Fab, Fab', F(ab')2, and Fv fragments; diabodies; minobodies; nanobodies; linear antibodies (Zapata et al. (1995) Protein Eng. 8(10):1057-1062); single-chain antibody molecules; and multispecific antibodies formed from antibody fragments.

Such fragments can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275-1281) to allow rapid and easy identification of monoclonal Fab fragments with the desired specificity.

Preferably, the antibody or an antigen-binding fragment of said antibody is either engineered so that it penetrates into cells or is directly expressed within cells using a gene therapy style approach. These latter are intracellular antibodies, which may also be called intrabodies, that are produced in the cell, and bind an antigen (e.g. FMRP protein, an mRNA encoding the FMR, etc. . . . ) within the same cell.

The present invention also contemplates a gene delivery vector, preferably in the form of a plasmid or a vector, that comprises one or more nucleic acid(s) encoding the miRNA, siRNA, piRNA, hnRNA, snRNA, sgRNA, esiRNA, shRNA, the peptide or analog thereof, the antibody or antigen-binding fragment of said antibody, or a similar intracellular antibody mimetic, and/or antisense oligonucleotide of the invention. As used herein, a "vector" is capable of transferring nucleic acid sequences to target cells (e.g., viral vectors, non-viral vectors, particulate carriers, and liposomes).

Suitable vectors include derivatives of SV40 and known bacterial plasmids, e. g., E. coli plasmids col El, pCR1, pBR322, pMB9 and their derivatives, plasmids such as RP4; phage DNAs, e.g., the numerous derivatives of phage X, e. g., NM989, and other phage DNA, e.g., M1 3 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Various viral vectors are used for delivering nucleic acid to cells in vitro or in vivo. Non-limiting examples are vectors based on Herpes Viruses, Pox-viruses, Adeno-associated virus, Lentivirus, and others. In principle, all of them are suited to deliver the expression cassette comprising an expressible nucleic acid molecule that codes for an miRNA, a siRNA, a piRNA, a hnRNA, a snRNA, an sgRNA, a esiRNA, a shRNA, and an antisense oligonucleotide of the invention.

Alternatively, the gene delivery vector of the invention, preferably the viral vector is issued for delivering a CRISPR-based loss-of-function system comprising i) at least one sgRNA, or crRNA and tracrRNA, targeting a regulatory sequence of FMR1 gene or a genomic DNA sequence encoding the FMRP mRNA, and ii) and a structure-guided endonuclease such as an RNA-guided endonuclease. Any suitable naturally occurring, or engineered, RNA-guided endonuclease can be employed as long as it is effective for specifically binding a target DNA of the invention and it may be selected from the non-limiting group comprising Cas9, Cpf1, and FEN-1. Preferably, the RNA-guided endonuclease is Cas9.

In a preferred aspect, said viral vector is an adenoviral vector, preferably a lenti- or baculo- or most preferably adeno-viral/adeno-associated viral (AAV) vectors but other means of delivery or vehicles are known (such as yeast systems, microvesicles, gene guns/means of attaching vectors to gold nanoparticles) and are provided, in some aspects, one or more of the viral or plasmid vectors may be delivered via liposomes, nanoparticles, exosomes, microvesicles, or a gene-gun. More preferably, the viral vector is selected from the group comprising an adeno-associated virus (AAV) and a lentivirus. Lentivirus of 1st, 2nd, and 3rd generation.

Also contemplated in the present invention is a host cell comprising a plasmid or vector of the invention or one or more nucleic acid(s) encoding the miRNA, siRNA, piRNA, hnRNA, snRNA, sgRNA, esiRNA, shRNA, a CRISPR-based loss-of-function system and/or antisense oligonucleotide of the invention. The host cell can be any prokaryotic or eukaryotic cell, preferably the host cell is a eukaryotic cell, most preferably the host cell is a mammalian cell. The host cell of the invention can deliver the plasmid or vector of the invention to the cancer cell(s) using a number of techniques known to those of skill in the art, such as e.g. exosomes and microvesicles.

Also provide herein is a pharmaceutical composition comprising:
i) a therapeutically effective amount of an agent modulating the expression and/or activity of the FMRP protein, an mRNA encoding the FMRP and/or the FMR1 gene as described herein, or
ii) a plasmid or a vector of the invention, or iii) a host cell of the invention, and a pharmaceutically acceptable carrier or diluent.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. Techniques for formulation and administration of the compounds of the instant application may be found in "Remington's Pharmaceutical Sciences," Mack Publishing Co., Easton, Pa., latest edition.

Any agent of the invention can be administered to an animal, including a human patient, by itself, or in pharmaceutical compositions where it is mixed with suitable carriers or excipient(s) at doses therapeutically effective to treat or ameliorate a variety of disorders, including those characterized by insufficient, aberrant, or excessive FMRP activity.

In some embodiments, the pharmaceutical composition of the invention is useful in the treatment and/or prevention of cancer and/or cancer metastasis in a subject in need thereof.

The term "therapeutically effective amount" as used herein means an amount of an agent modulating the expression and/or activity of the FMRP protein, an mRNA encoding the FMRP and/or the FMR1 gene high enough to significantly positively modify the symptoms and/or condition to be treated, but low enough to avoid serious side effects (at a reasonable risk/benefit ratio), within the scope of sound medical judgment.

The therapeutically effective amount of the agent modulating the expression and/or activity of the FMRP protein, an mRNA encoding the FMRP and/or the FMR1 gene is selected in accordance with a variety of factors including type, species, age, weight, sex and medical condition of the patient; the severity of the condition to be treated; the route of administration; the renal and hepatic function of the patient. A physician of ordinary skill in the art can readily determine and prescribe the effective amount of the drug required to prevent, counter or arrest the progress of cancer and/or cancer metastasis.

"Pharmaceutically acceptable carrier or diluent" means a carrier or diluent that is useful in preparing a pharmaceutical composition that is generally safe, non-toxic, and desirable, and includes carriers or diluents that are acceptable for human pharmaceutical use.

Such pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Pharmaceutically acceptable excipients include starch, glucose, lactose, sucrose, sodium stearate, glycerol monostearate, talc, sodium chloride, dried skim milk, glycerol, propylene glycol, water, ethanol and the like.

The pharmaceutical compositions may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include macrocrystalline cellulose, carboxymethyf cellulose sodium, polysorbate 80, phenyletbyl alcohol, chiorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In some embodiments, the invention relates to the identification, production, and use of agents which modulate FMRP gene expression or the activity of the FMRP gene product including but not limited to nucleic acid encoding FMRP and homologues, analogues, and deletions thereof, as well as a chemical compound, a peptide or analog thereof, an antibody or an antigen-binding fragment of said antibody, antibody mimetic, or a nucleic acid; and pharmaceutical formulations and routes of administration for such compounds.

An assay employing FMRP transfectants can be used to successfully identify agents which modulate the expression of the FMRP gene. Assays for the activity of the FMRP gene product are also described.

The present invention also comprises antisense oligonucleotides specific for the FMRP transcript; antibodies (fragments and mimetics) to the gene product; cell lines engineered to stably express FMRP; assays for screening compounds, including peptides, polynucleotides, and small organic molecules, to identify those that inhibit the expression or activity of the FMRP gene product; and methods of treating diseases characterized by FMRP activity using such compounds.

Human FMRP protein would be useful for in vitro studies on the mechanism of action of the human FMRP and particularly for further studies on the mechanism of action of any inhibitors that are selective for FMRP that are identified by drug screening, or for investigating the mechanism of action of existing drugs or of inhibitors that may be identified by other means. The purified human FMRP protein would also be useful for the production of crystals suitable for X-ray crystallography. Such crystals would be extremely beneficial for the rational design of drugs based on molecular structure.

The present invention provides an in vitro system for the screening of agents that modulate FMRP stability and/or activity. Assays can be performed on living mammalian cells, which more closely approximate the effects of a particular serum level of agent in the body, or on microsomal extracts prepared from the cultured cell lines. Studies using microsomal extracts offer the possibility of a more rigorous determination of direct interactions.

Thus, the present invention also provides a method to evaluate the relative inhibitory activity of an agent to selectively inhibit FMRP. This assay comprises, for example, contacting a FMRP-expressing transgenic cell line or a microsomal extract thereof with a preselected amount of an agent in a suitable culture medium or buffer, adding arachidonic acid to the mixture, and measuring the level of synthesis of a FMRP or activity of FMRP protein, by said cell line, or said microsomal extract, as compared to a control cell line or portion of microsomal extract in the absence of said agent.

In some embodiments, the present invention provides a method of determining the ability of an agent to inhibit FMRP activity in cells comprising:
 (1) adding a first preselected amount of said agent to a cell in culture medium, which cell contains a DNA sequence which expresses FMRP;
 (2) measuring the level of a FMRP activity by said cell; and
 (3) comparing said level with the level of FMRP activity by cell line in the absence of said agent.

In some embodiments, the cell is a transgenic cell. In some embodiments, the cell is a transgenic cell line. In some embodiments, the transgenic cell or transgenic cell line comprises cells which contains a chromosomally integrated, recombinant DNA sequence, which expresses FMRP. In some embodiments, the cell is a mammalian cell. In some embodiments, the cell does not express autologous FMRP activity.

In some embodiments, the cell is a human or mouse cancer cell that has in the course of tumorigenesis and malignant progression markedly upregulated expression of FMRP so as to acquire resistance to immune attack.

In some embodiments, the FMRP is mammalian FMRP, preferably human FMPR.

In some embodiments, the level of expression of and/or activity of FMRP is determined by the agent disrupting the binding of by FMRP to its target RNA.

In some embodiments, the present invention provides a method of identifying an agent that modulates the expression and/or activity of i) the FMRP protein, ii) an mRNA encoding the FMRP and/or iii) the FMR1 gene, the method comprising:
 (1) providing a sample expressing FMRP;
 (2) contacting the biological sample with a test agent;
 (3) determining the level of expression of and/or activity of FMRP;
 (4) comparing the level of expression and/or activity with a control sample not contacted by the test agent; and
 (5) selecting a test agent that decreases the level of expression of and/or activity of FMRP.

In some embodiments, the sample is a cell that naturally expresses high levels of endogenous FMRP. In some embodiments, the sample is a cell that is engineered to express FMRP.

In some embodiments, the cell is a transgenic cell. In some embodiments, the cell is a transgenic cell line. In some embodiments, the transgenic cell or transgenic cell line comprises cells which contains a chromosomally integrated, recombinant DNA sequence, which expresses FMRP. In some embodiments, the cell is a mammalian cell. In some embodiments, the cell does not express autologous FMRP activity.

In some embodiments, the cell is a human or mouse cancer cell that has in the course of tumorigenesis and malignant progression markedly upregulated expression of FMRP so as to acquire resistance to immune attack.

In some embodiments, the FMRP is mammalian FMRP, preferably human FMPR.

In some embodiments, the level of expression of and/or activity of FMRP is determined by the agent disrupting the binding of by FMRP to its target RNA.

The agents identified in a screen will demonstrate the ability to selectively modulate the expression and/or activity of FMRP. These agents include but are not limited to nucleic acid encoding FMRP and homologues, analogues, and deletions thereof, as well as a chemical compound, a peptide or analog thereof, an antibody or an antigen-binding fragment of said antibody, antibody mimetic, or a nucleic acid.

The DNA of the invention encoding the FMRP gene or homologues, analogues, or fragments thereof may be used in accordance with the invention to diagnose disease states which are phenotypic of an FMRP genotype or of FMRP expression.

Alternatively, the pharmaceutical composition of the invention further comprises one of several components of an anti-cancer therapy. Preferably, the anti-cancer therapy comprises a therapeutically effective amount of an immune checkpoint inhibitor. Preferably, the immune checkpoint inhibitor is selected from the group comprising a PD-1 inhibitor, a PD-L1 inhibitor, and a CTLA-4 inhibitor, or a combination thereof. Alternatively, or additionally, the one or more anti-cancer therapy is a chemotherapeutic agent or cocktail of multiple different chemotherapeutic agents as described herein.

As used herein, a "PD-1 inhibitor" means any agent that interferes or blocks the binding of PD-1 receptor on T cells with its ligands, PD-L1 and PD-L2, which are present on tumor cells. The PD-1 inhibitor may be an antibody or a fragment thereof, which interferes with, inhibits, or blocks the PD-1 binding to its ligands. A PD-1 inhibitor may also be a small molecule or any other agent. Non-limiting examples of PD-1 inhibitor comprise nivolumab, pembrolizumab, pidilizumab, BMS 936559, MPDL3280A, MSB0010718C BGB-108 and mDX-400 and MEDI4736.

Non-limiting examples of PD-L1 inhibitors are selected from the group comprising MEDI-0680, RG-7446, durvalumab, KY-1003, KD-033, MSB-0010718C, TSR-042, ALN-PDL, STI-A1014 and BMS-936559.

As used herein, a "CTLA-4 inhibitor" means any agent that interferes or blocks CTLA-4 such as anti-CTLA-4 mAb or blocker, e.g., ipilimumab, tremelimumab and abatacept.

In another aspect, the anti-cancer therapy directed at FMRP is included in combination with a therapeutically effective amount of an anti-tumor-vaccine, including personalized neo-antigen cocktails, or other immune-stimulatory agents that bolster anti-tumor immune responses.

The present invention further provides a method of treatment and/or prevention of cancer and/or cancer metastasis in a subject in need thereof, comprising administering to said subject a pharmaceutical composition of the invention, alone or in combination with one or more anti-cancer therapy. Most preferably, the anti-cancer therapy comprises a therapeutically effective amount of an immune checkpoint inhibitor. Preferably, the immune checkpoint inhibitor is selected from the group comprising a PD-1 inhibitor, a PD-L1 inhibitor, and a CTLA-4 inhibitor, or a combination thereof. Alternatively, or additionally, the anti-cancer therapy is a chemotherapeutic agent or cocktail of multiple different chemotherapeutic agents as described herein.

It will be appreciated that the combination of a pharmaceutical composition of the invention and the PD-1/PD-L1/CTLA-4 inhibitor may be administered in any order or concurrently. In selected aspects, the pharmaceutical composition and PD-1/PD-L1/CTLA-4 will be administered to patients that have previously undergone treatment with other anti-cancer agents. In certain other aspects, the pharmaceutical composition and the PD-1/PD-L1/CTLA-4 inhibitor will be administered substantially simultaneously or concurrently. For example, a subject may be given a pharmaceutical composition of the invention while undergoing a course of treatment with the PD-1/PD-L1/CTLA-4 inhibitor. In addition, it is contemplated that the subject has already or may be concurrently receiving other forms of cancer therapy, e.g., chemotherapy. In certain aspects, the pharmaceutical composition of the invention will be administered within 1 year of the treatment with the PD-1/PD-L1/CTLA-4 inhibitor. In certain alternative aspects, the pharmaceutical composition of the invention will be administered within 10, 8, 6, 4, or 2 months of any treatment with the PD-1/PD-L1/CTLA-4 inhibitor and/or additional anti-cancer therapy. In certain other aspects, the pharmaceutical composition of the invention will be administered within 4, 3, 2, or 1 week of any treatment with the PD-1/PD-L 1/CTLA-4 inhibitor and/or additional anti-cancer agent or therapy. In some aspects, the pharmaceutical composition of the invention will be administered within 5, 4, 3, 2, or 1 days of any treatment with the PD-1/PD-L1/CTLA-4 inhibitor and/or additional anti-cancer therapy or agent. It will further be appreciated that the pharmaceutical composition of the invention and the PD-1/PD-L1/CTLA-4 inhibitor and/or additional anti-cancer agent or therapy may be administered to the subject within a matter of hours or minutes (i.e., substantially simultaneously).

In embodiments, the agent of the invention could be combined with other immunomodulator agents that either sustain the killing activity and abundance of T cell (and NK cells), or disrupt other barriers, such as myeloid derive suppressor cells (MDSC) and immuno-suppressive macrophages in so far as their activities are complementary to the effects of inhibiting FMRP.

In some embodiments, the agent of the invention could be combined an ADAR1 inhibitor. Knockout (i.e. genetic inhibition) of ADAR1, an immunosuppressive RNA editing enzyme, has combinatorial benefit in extending overall survival in double-KO tumors also carrying a knockout of FMRP.

Anticancer agents that may be administered in combination with the pharmaceutical composition of the invention and PD-1/PD-L1/CTLA-4 inhibition include chemotherapeutic agents. Thus, in some aspects, the method or treatment involves the combined administration of a pharmaceutical composition of the invention and PD-1/PD-L1/CTLA-4 inhibitor and a chemotherapeutic agent or cocktail of multiple different chemotherapeutic agents. Treatment with a pharmaceutical composition of the invention can occur prior to, concurrently with, or subsequent to administration of these other therapies. Chemotherapies contemplated by the invention include chemical substances or drugs which are known in the art and are commercially available, such as gemcitabine, irinotecan, doxorubicin, 5-fluorouracil, cytosine arabinoside ("Ara-C"), cyclophosphamide, thiotepa, busulfan, cytoxin, TAXOL, methotrexate, cisplatin, melphalan, vinblastine and carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner.

Chemotherapeutic agents useful in the instant invention also include, but are not limited to, alkylating agents such as thiotepa and cyclophosphamide (CYTOXAN); alkyl sulfonates such as busulfan, improsulfan, and piposulfan;

aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL, Bristol-Myers Squibb Oncology, Princeton, N.J.) and doxetaxel (TAXOTERE, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (OMFO); retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, L Y117018, onapristone, and toremifene (Fareston); and antiandrogens such as flutamide, nilutamide, bicalutamide, leuprolide, and goserelin; and pharmaceutically acceptable salts, acids or derivatives of any of the above.

In certain aspects, the therapeutic agent is a kinase inhibitor. In certain aspects, the kinase inhibitor is a multi-targeted receptor tyrosine kinase inhibitor. Kinase inhibitors include, but are not limited to, sunitinib, pazopanib, crizotinib, dasatinib. In certain aspects, the second anticancer agent is sunitinib.

In certain aspects, the therapeutic agent is an inhibitor of mammalian target of rapamycin (mTOR). mTOR inhibitors include, but are not limited to, temsirolimus, sirolimus, deforolimus and everolimus. In certain aspects, the second anticancer agent is everolimus.

In certain aspects, therapeutic agent is a somatostatin analog. Somatostatin analogs act through interaction with specific, high affinity membrane receptors for somatostatin. Somatostatin analogs include, but are not limited to, octreotide, somatuline, and RC 160 (octastatin). In certain aspects, the second anticancer agent is octreotide.

In certain aspects, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin 0, etoposide, Topotecan HCl, teniposide (VM-26), and irinotecan. In certain aspects, the second anticancer agent is irinotecan.

In certain aspects, the chemotherapeutic agent is an alkylating agent. In certain aspects, the chemotherapeutic agent is temozolomide.

In certain aspects, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, THIOGUANINE (GlaxoSmithKline), 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain aspects, the second anticancer agent is gemcitabine. In certain aspects, the tumor to be treated is a pancreatic neuroendocrine tumor and the second anticancer agent is an anti-metabolite (e.g., gemcitabine).

In certain aspects, the chemotherapeutic agent is an antimitotic agent, including, but not limited to, agents that bind tubulin. By way of non-limiting example, the agent comprises a taxane. In certain aspects, the agent comprises paclitaxel or docetaxel, or a pharmaceutically acceptable salt, acid, or derivative of paclitaxel or docetaxel. In certain aspects, the agent is paclitaxel (TAXOL), docetaxel (TAXOTERE), albumin-bound paclitaxel (e.g., ABRAXANE), DHA-paclitaxel, or PG-paclitaxel. In certain alternative aspects, the antimitotic agent comprises a vinca alkaloid, such as vincristine, vinblastine, vinorelbine, or vindesine, or pharmaceutically acceptable salts, acids, or derivatives thereof. In some aspects, the antimitotic agent is an inhibitor of Eg5 kinesin or an inhibitor of a mitotic kinase such as Aurora A or Plk1.

In certain aspects, the treatment involves the combined administration of a pharmaceutical composition of the invention and a PD-1/PD-L1/CTLA-4 inhibitor described herein and radiation therapy. Treatment with the pharmaceutical composition of the invention can occur prior to, concurrently with, or subsequent to administration of radiation therapy. Any dosing schedule for such radiation therapy can be used as determined by the skilled practitioner.

In other aspects of the invention, the pharmaceutical compositions of the invention is a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

In other aspects of the invention, the pharmaceutical compositions of the invention is administered prior to, during and/or after said patient was subjected to a radiation therapy.

"Radiation therapy" refers to the use of high-energy radiation to shrink tumors and kill cancer cells. Examples of radiation therapy include, without limitation, external radiation therapy and internal radiation therapy (also called brachytherapy).

External radiation therapy is most common and typically involves directing a beam of direct or indirect ionizing radiation to a tumor or cancer site. While the beams of radiation, the photons, the Cobalt or the particule therapy are focused to the tumor or cancer site, it is nearly impossible to avoid exposure of normal, healthy tissue. Energy source for external radiation therapy is selected from the group comprising direct or indirect ionizing radiation (for example: x-rays, gamma rays and particle beams or combination thereof).

Internal radiation therapy involves implanting a radiation-emitting source, such as beads, wires, pellets, capsules, etc., inside the body, at, or near to the tumor site. Energy source for internal radiation therapy is selected from the group of radioactive isotopes comprising: iodine (iodine125 or iodine131), strontium89, radioisotopes of phosphorous, palladium, cesium, indium, phosphate, or cobalt, and combination thereof. Such implants can be removed following treatment, or left in the body inactive. Types of internal radiation therapy include, but are not limited to, interstitial, and intracavity brachytherapy (high dose rate, low dose rate, pulsed dose rate).

A currently less common form of internal radiation therapy involves biological carriers of radioisotopes, such as with radio-immunotherapy wherein tumor-specific antibodies bound to radioactive material are administered to a patient. The antibodies bind tumor antigens, thereby effectively administering a dose of radiation to the relevant tissue.

Methods of administering radiation therapy are well known to those of skill in the art.

The pharmaceutical compositions of the present invention may be administered to a subject by different routes including, but not limited to, orally, parenterally, sublingually, transdermally, rectally, transmucosally, topically, via inhalation, via buccal administration, intrapleurally, intravenous, intraarterial, intraperitoneal, subcutaneous, intramuscular, intranasal, intratumoral, intrathecal, and intraarticular or combinations thereof. For human use, the composition may be administered as a suitably acceptable formulation in accordance with normal human practice. The skilled artisan will readily determine the dosing regimen and route of administration that is most appropriate for a particular patient. The compositions of the invention may be administered by traditional syringes, needleless injection devices, "microprojectile bombardment gone guns", or other physical methods such as electroporation ("EP"), "hydrodynamic method", or ultrasound.

The pharmaceutical compositions of the present invention may also be delivered to the patient, by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus sa described herein. The compositions may be injected intra veniously or locally injected in the brain or muscle or electroporated in the tissue of interest such as, e.g., muscle, brain, liver, prostate, breast, kidney(s), and hematopoietic system.

The agent and/or pharmaceutical compositions of the present invention may be used in any method where modulating the expression and/or the immuno-suppressive activity of i) the FMRP protein, ii) an mRNA encoding the FMRP protein, and/or iii) the FMR1 gene that encodes FMRP would be beneficial.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein. Various references are cited throughout this Specification, each of which is incorporated herein by reference in its entirety. The foregoing description will be more fully understood with reference to the following Examples.

EXAMPLES

Example 1

Material and Methods
Generation of Crisper-Edited Tumor Cell Line

Mouse PDAC 4361.12 cells were cultured in DMEM with 10% FBS. The FMR1 gene was knocked out in cells using the CRISPR/Cas9 system. Cells were transiently transfected with two Cas9 and single-guide RNAs (sgRNA) expression plasmids and selected by blasticidin for five days. This transient CRISPR strategy for the knockout of FMRP prevents any potential unspecific effects mediated by stable tntegration of Cas9/sgRNA into the genome. The guide sequences used for FMR1 are 5'-GTG-GAAGTGCGGGGCTCCAA-3' (SEQ ID NO: 12) or 5'-GAGCTGGTGGTGGAAGTGCG-3' (SEQ ID NO: 13). Cells were single-cell plated into 96-well plate without blasticidin. Knockout clones were selected by immunoblot blotting for the lack of FMRP proteins. Obtained FMRP KO cells kept sensitive to blasticidin, indicating the CRISPR/Cas9 system was only transiently expressed in those cells. Two independent KO clones and WT clones (transfected with a Cas9 abd an empty SgRNA vectors) were analyzed as indicated.

Animal Studies

All experiments using animals were performed in accordance with protocols approved by the local animal experimentation committee of the Canton de Vaud (license number 3214). FVBn, Balb/c or C57B/6, NSG or SCID/beige mice were used at 8 weeks of age. For the lung metastasis assay, $2\times10^5$ mouse PDAC WT or FMRP KO cells suspended in 200 μl PBS were injected into were injected into the lateral tail vein of the mice. For the primary tumor growth assay, $5\times10^5$ cells suspended in 100 μl PBS were injected subcutaneously into the mice.

Analysis of Tumor-Infiltrating Lymphocytes by Flow Cytometry

Flow cytometry was performed using a BD LSRII Fortessa and results were analyzed using FlowJo software (Treestar). Primary tumor cell suspensions were blocked by mouse Fc block (anti CD16/CD32; Biolegend, #101312) prior to staining. Fluorochrome conjugated anti-mouse CD45 (clone 30F-11), CD3e (clone 145-2C11), CD8a (clone 53-6.7), Granzyme B (clone NGZB), TNFa (MP6-XT22) and IFNg (clone XMG1.2) antibodies were used following the manufacturers protocol. Blue UV was used to stain dead cells. To analyze intracellular cytokine expression, mice bearing s.c. tumors were I.P. injected with 250 μg protein transport inhibitor Brefaldin A (BD biosciences, #555029) 6 hrs before the sacrifice. Intracellular cytokine staining was then performed using Fixation/Permeabilization Solution Kit (Sigma, B6542-25MG).

Immunohistochemical and Immunofluorecent Staining

Harvested mouse tissues were fixed in 4% paraformaldehyde overnight, embedded in paraffin, and sectioned by microtome (Leica). Antigen retrieval was performed in a citrate buffer (pH=6.0) in a water bath at 95° C. for 20 min, or in a tris-EDTA buffer (pH=8.0) in water bath at 95° C. for 10 min. Primary antibodies were incubated at 4° C. overnight. For Immunohistochemical (IHC) staining, 2nd antibodies (ImmPRESS HRP reagent kit, anti-rabbit MP-7401 and anti-rat MP-7444) were incubated at room temperature for 45 min, and finally visualized with the peroxidase substrate DAB (Sigma-Aldrich, D5637-1G) for the same amount of time (maximum 10 min) at room temperature. The stained tissue sections were counterstained with Meyer's hematoxylin. For Immunofluorencent (IF) staining, 2nd antibodies (Alexa Fluor 488, 568, 647, Thermo Fisher Scientific) were incubated at room temperature for 45 min. Images were acquired with Leica DM5500B and Zeiss LSM 700 upright confocal microscopes, and analyzed with Image J. Antibodies used are as follows, FMRP, Abcam, ab191411; mouse CD8, Thermo Fisher Scientific, 14-0808-82.

Statistical Analysis

Statisticsl analysis was performed with Prism 7 (GraphPad Software). Unless stated otherwise, the Student's t test was used for non-paired experiments (two-tailed). Wilcoxon matched pairs test (two-tailed) was performed for paired experiments that did not follow a Gaussian distribution. $P<0.05$ was considered statistically significant. Values are mean±SEM.

Results

A recent study revealed that FMRP acts as a downstream effector of NMDAR signaling in promoting the invasive growth of pancreatic cancer.[16] We further comfirmed the elevated FMRP expression is found in human (data not shown) and murine PDAC tissues (FIG. 1A).

Figure 1B:
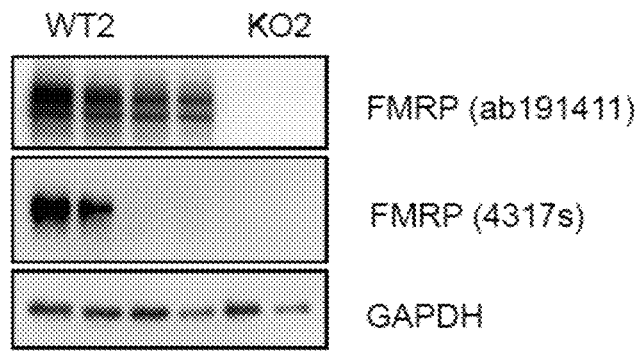

To further explore the role of FMRP in tumor progression, we used the Crisper/Cas9 system[10] to knock-out FMRP in murine pancreatic adenocarcinoma (PDAC) cell line 4361.12 (FIG. 1B), which is a single cell-derived cell line from the P48-cre; LSL-Kras$^{G12D}$; P53$^{R172H/+}$ PDAC mouse model in the FvBn background. Importantly, a transient Crisper strategy for the knock-out of FMRP was performed to avoid any potential unspecific effects and immunogenicity mediated the stable Cas9/sgRNA genome integration.

Figure 1C:
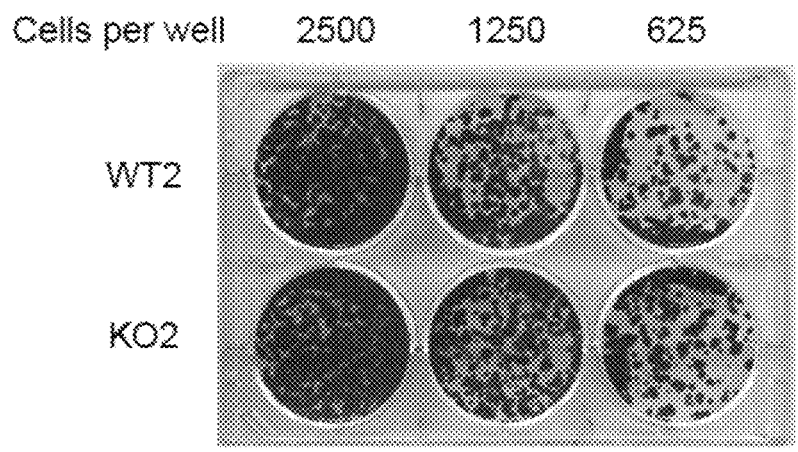
Figure 1D:
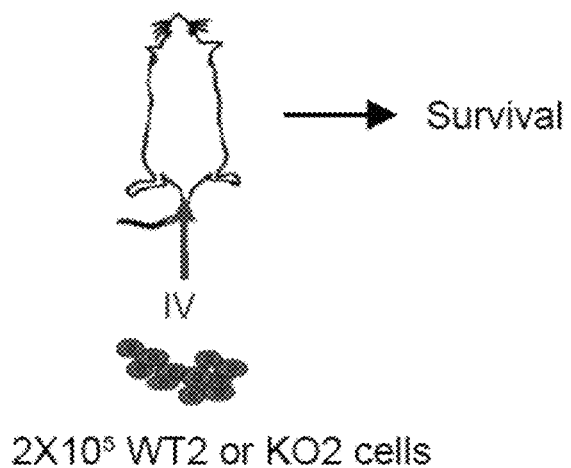
Figure 1E:
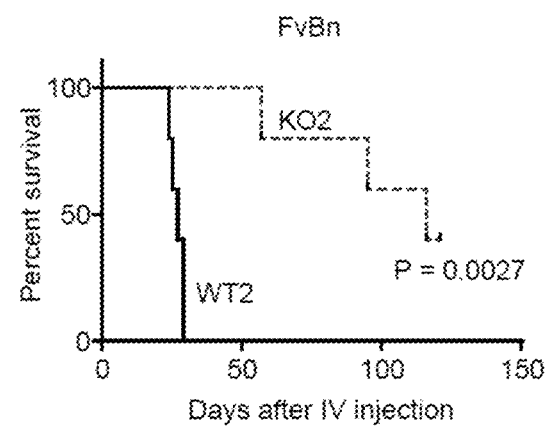
Figure 1F:
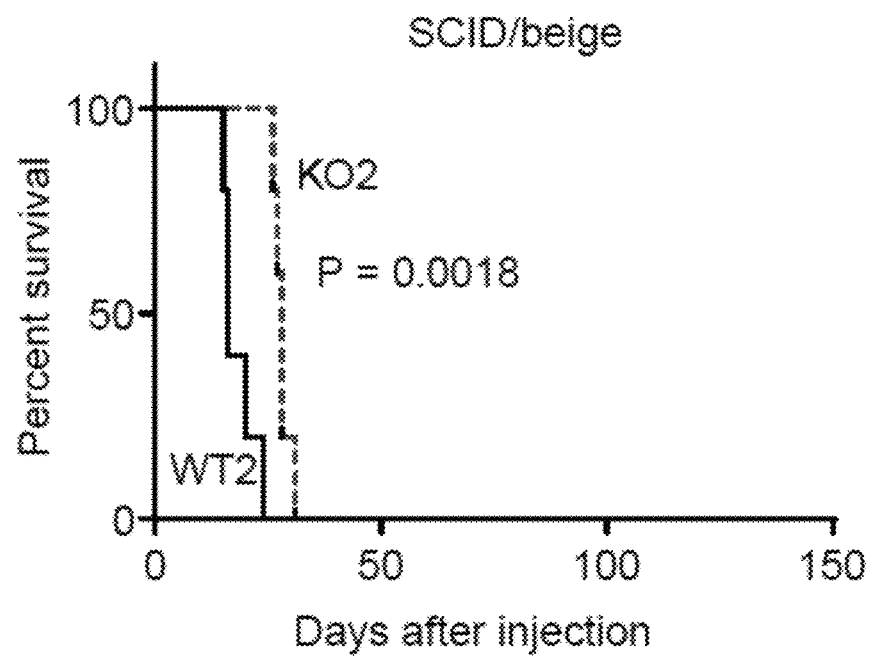
Figure 1G:
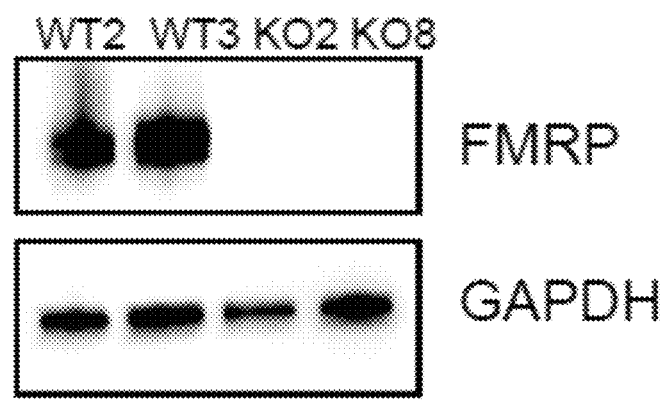
Figure 1H:
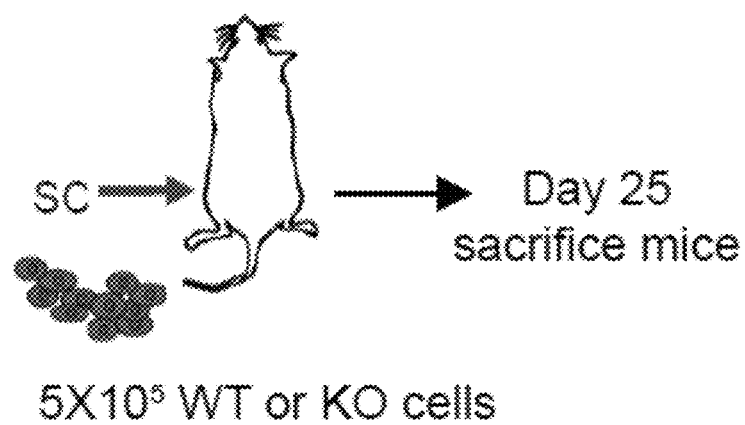
Figure 1I:
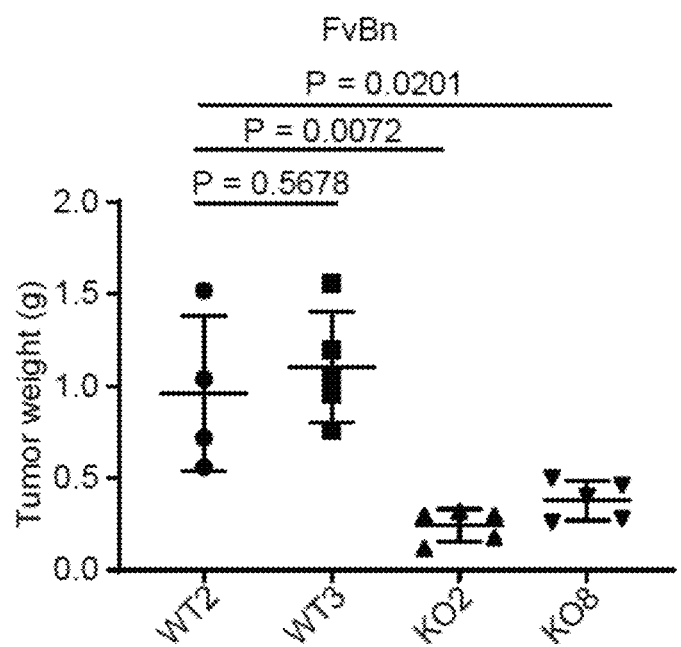
Figure 1J:
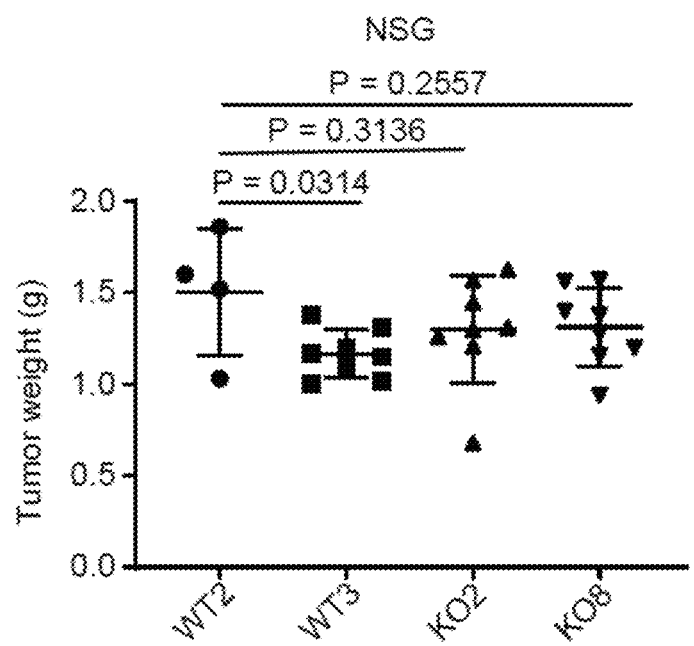

In vitro functional assay shows that there are no significant differences in colony formation capabilities between WT and FMRP KO PDAC cells (FIG. 1C). Considering the possible role of FMRP in metastasis, we first injected WT and FMRP KO cells into the tail vein of the immunocompetent FVBn mice, a standard in vivo lung metastasis assay (FIG. 1D). Strikingly, two out of the five mice injected with the FMRP-KO2 cells survived for 120 days after the injection, while all the five mice injected with the FMRP-WT cells died before 25 days after the injection (FIG. 1E). When a similar in vivo lung metastasis assay was performed in immunodeficient SCID/beige mice, there was not such a profound difference in overall survival between these two groups (FIG. 1F), implicating the adaptive immune system in the survival benefit observed in mice bearling FMRP-KO tumors. We then turned to use a primary tumor model formed by subcutaneous injection of cancer cells (FIG. 1H). Tumor growth of FMRP-KO cells was seriously impaired compared with FMRP-WT cells when they were subcutaneously injected into FVBn mice, while no significant change in tumor weight between these two groups was observed when the cells were subcutaneously injected into immunodeficient NSG mice (FIG. 1I and 1J), further implicating a possible role of FMRP in modulating anti-tumor immunity in vivo.

Figure 2A:
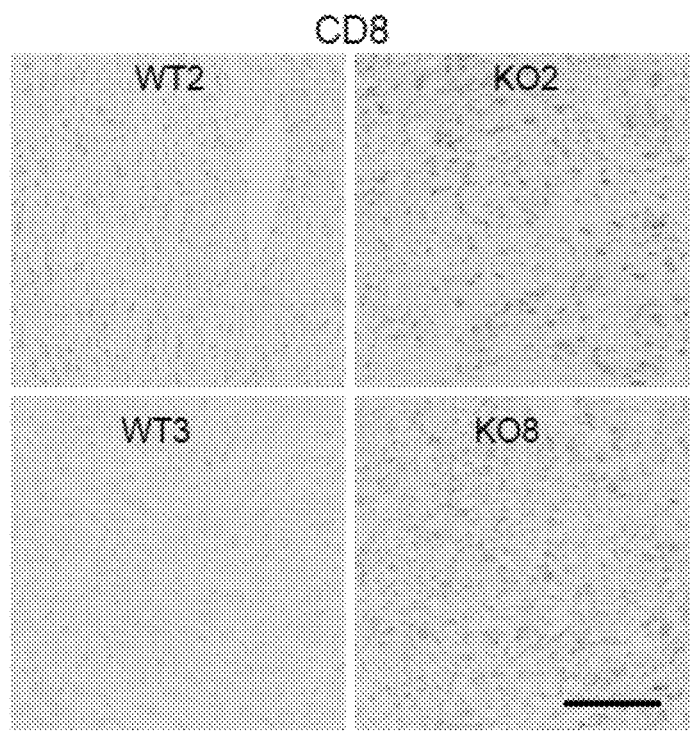
FIG. 2A-2H. Deletion of FMRP in mouse PDAC cancer cells elicits an intense anti-tumor immune response in the form of infiltrating CD8+ (cytotoxic) T lymphocytes. (A) Immunochemical staining and quantification of CD8+ (cytotoxic) T lymphocytes in primary tumors formed by mouse PDAC WT and KO cells, scale bar, 100 μm, n=3 mice for each group; (B) IF staining and quantification of CD45+ immune cells in primary tumors formed by mouse PDAC WT2 and KO2 cells, scale bar, 100 μm, n=3 mice for each group; (C-G) FACS analysis was used to determine the frequency of CD45+ immune cells, of CD3+CD8+ T cells, and of activated GRZb+, IFNγ+ and TNFα+, CD8 T cells, in PDAC WT and FMRP KO tumors growing in immunocompetent mice. n=4~5 mice per group, two independent experiments. The unpaired T-test was used. (H) Representative double immunostaining images of FMRP and CD8 expression in the center and in the edge of mouse PDAC tissues from P48-cre; LSL-KrasG12D; P53R172H/+ PDAC mouse model in the FVBN background. n=8 mouse PDAC samples. Paired T-test was used. Scale bar, 100 μm. The data support the interpretation that FMRP is preventing the influx of CD8 T cells that is seen in the KO tumors (Panel A). Immunostaining of human PDAC tissue-microarrays for CD8 and FMRP (not shown) shows an inverse correlation between density of infiltrating CD8 T cells and expression of FMRP, concordant with the results in mouse PDAC.
Figure 2A:
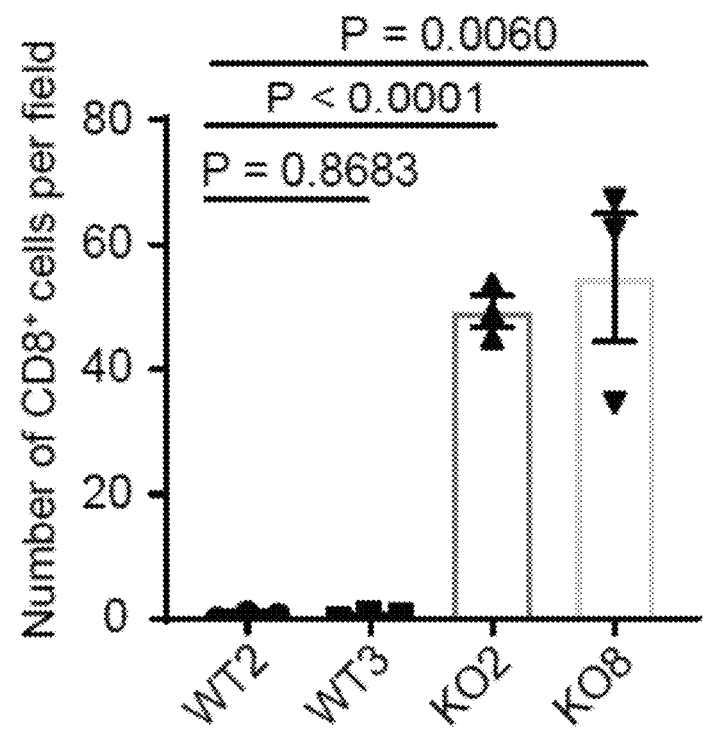
Figure 2B:
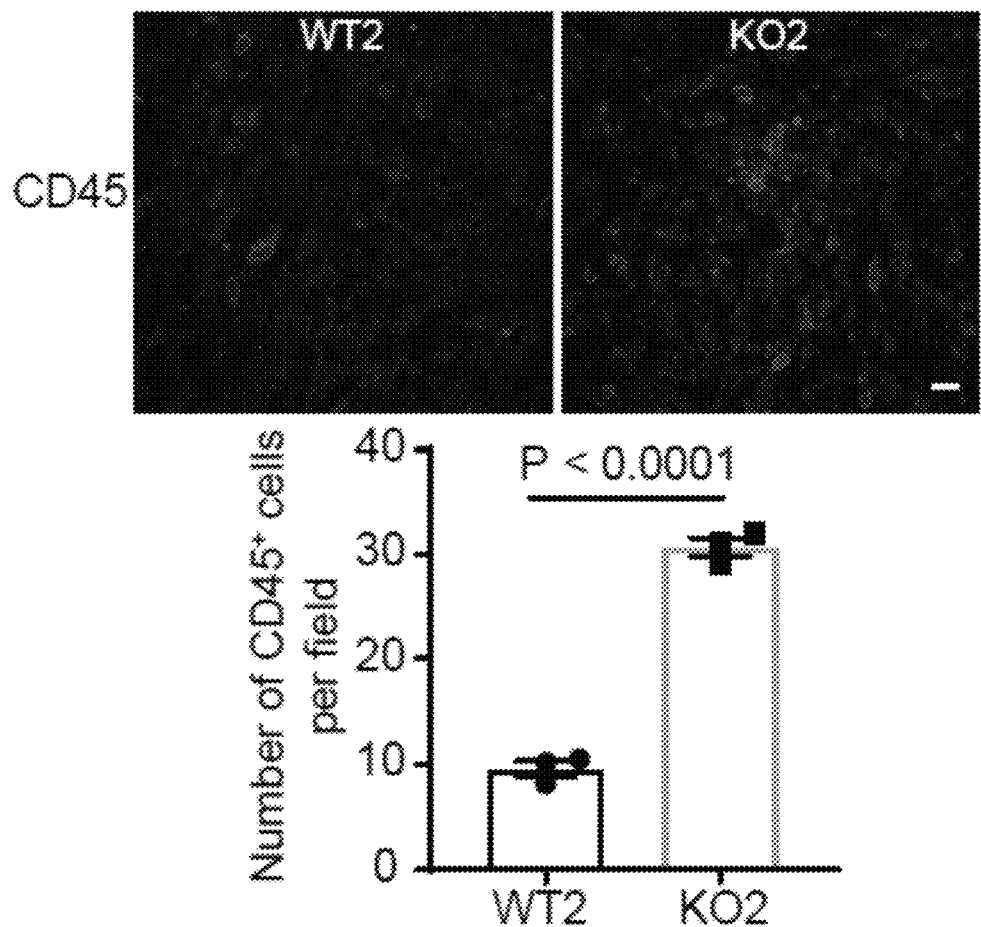
Figure 2C:
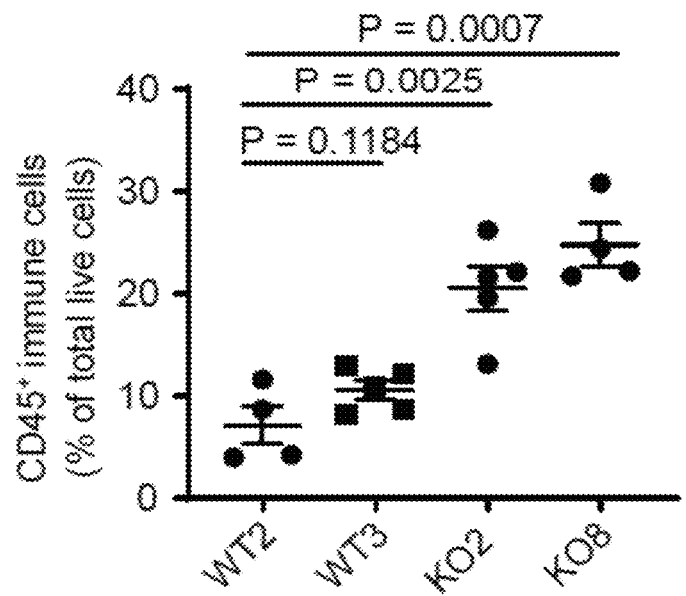
Figure 2D:
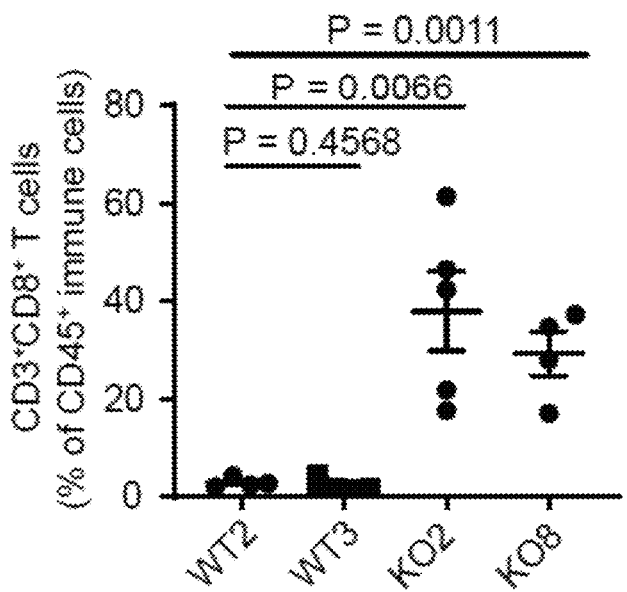
Figure 2E:
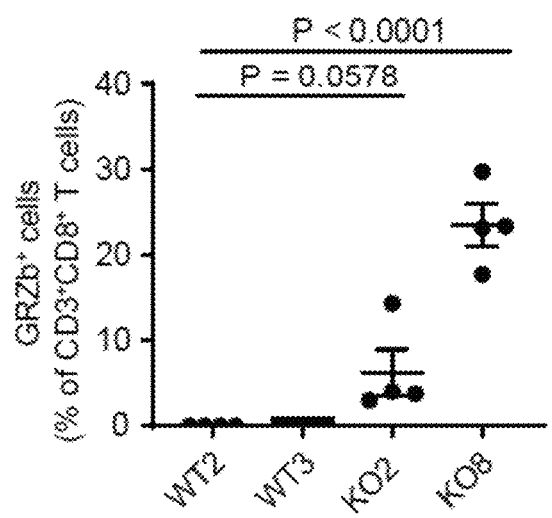
Figure 2F:
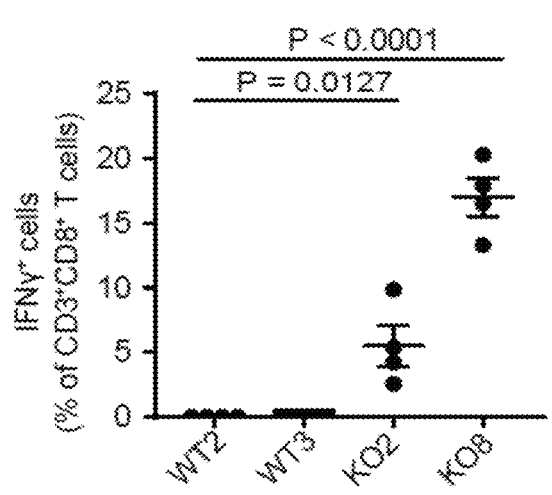
Figure 2G:
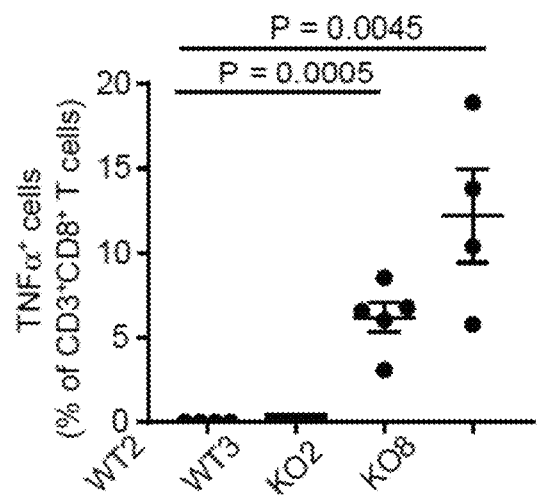
Figure 2H:
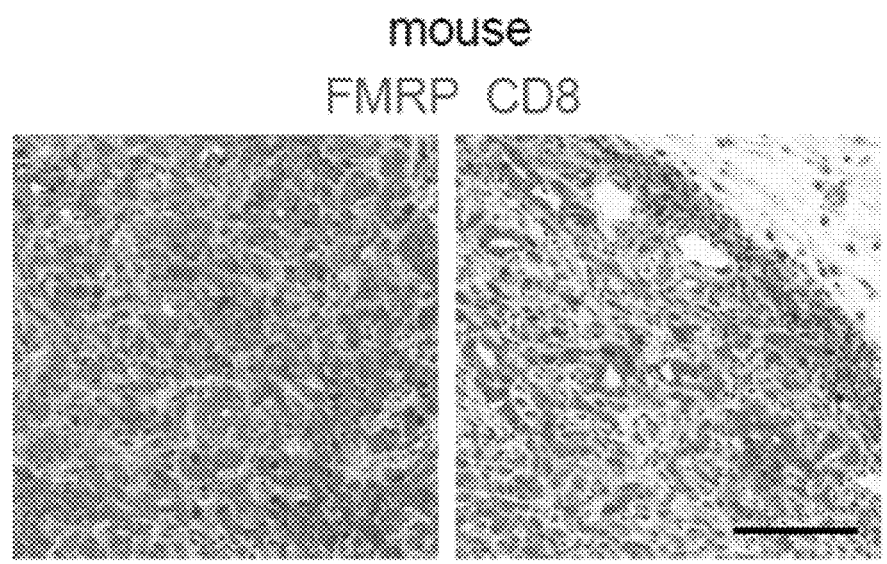
Figure 2H:
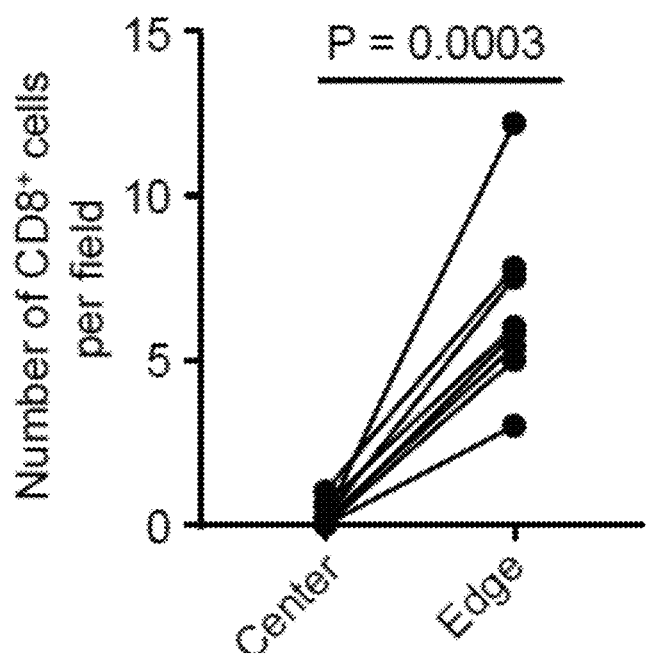

Importantly, IHC staining of tumors formed from WT and FMRP-KO cancer cells revealed a large number of infiltrated CD8+ cytotoxic T cells in the KO tumors; in sharp contrast, there were almost no CD8+T cells in WT tumors (FIG. 2A). FMRP KO tumors also have increased numbers of CD45+ immune cells compared with WT tumors (FIG. 2B). Consistently, FACS analysis of primary cell suspensions from WT and FMRP-KO tumors further demonstrated the dramatically increased number of CD45+ immune cells, CD3+CD8+ T cells, and GRZb+, IFNγ+ and TNF+ T cells in KO tumors compared with WT tumors (FIG. 2C-2G), further supporting the role of FMRP in suppressing anti-tumor immunity in vivo. Double IHC staining of FMRP and CD8 in mouse PDAC tissues was further performed, and found that CD8 T cells were be barely detectable in the center of FMRP-expressing tumors (FIG. 2H). Significant reverse association between FMRP expression and CD8 T cell infiltration in human PDAC samples was also determined.

Figure 3A:
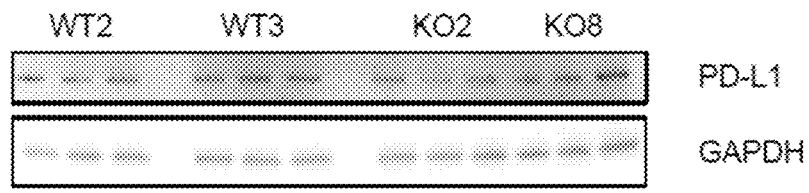
FIG. 3A-3D. The FMRP KO in cancer cells sensitizes otherwise resistant PDAC tumors to immunotherapy involving anti-PD1 antibody treatment. (A,B) FMRP deletion does not suppress PD-L1 expression in mouse PDAC cells in vitro or in vivo. (A) WB analysis of PD-L1 expression in mouse PDAC WT and FMRP KO cells, three independent experiments. (B) Immunostaining to detect PD-L1 expression in tumors formed by murine PDAC WT and FMRP KO cells, scale bar, 100 μm, n=3 mice for each group. (C, D) PDAC WT2 and KO2 tumor growth curves without or with anti-PD-1 antibody therapy (I.P., 200 ug per mice, twice per week), all in FVBn mice. n=7~11 mice per group, the unpaired T-test was used. (C)This result indicates that PDAC tumors arsising from this mouse PDAC cancer cell line are insensitive to anti-PD-1 treatment. (D) In notable contrast, the FMRP KO severely impairs PDAC tumor growth assoicated with an increased influx of CD8 T cells (as show in FIG. 1G-I, 2A, and 4D), suggesting that FMRP inhibitors could have therapeutic efficacy in tumors resistant to anti-PD1/PD-L1 therapies.
Figure 3B:
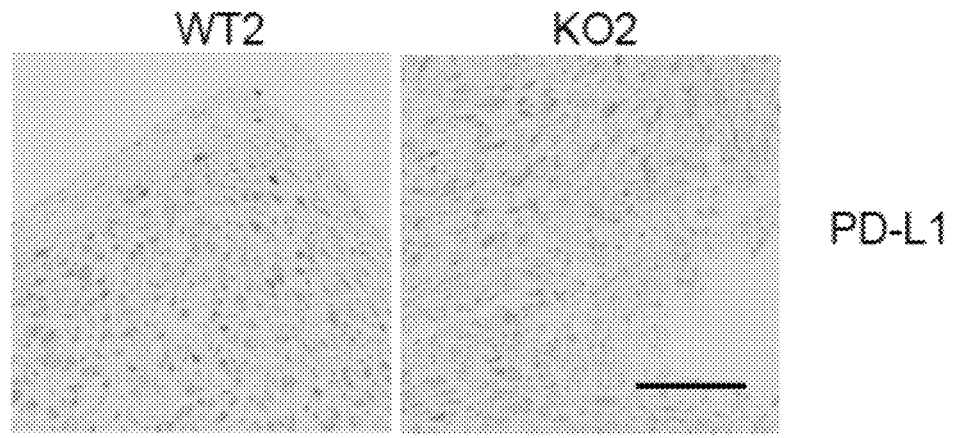

Whether the deletion of FMRP in cancer cells changed the expression of immune checkpoint proteins so as to trigger the anti-tumor immune responses was explored. If FMRP-suppressed anti-tumor immunity depended on the well-established T cell co-inhibitory PD-1 or CTLA-4 signaling, downregulation in FMRP-KO tumor cells of PD-1 ligands PD-L1/CD274 and PD-L2/PDCD1LG2, or perhaps the CTLA-4 ligands B7/B7-1/CD80 and CD86 would be expected. However, WB analysis and IHC staining shows unchanged PD-L1 expression comparing WT and FMRP KO cells in vitro and in vivo (FIG. 3A-B), while PDL2, CD86, and CD80 were barely detected in either (data not shown), indicating that the underlying mechanism of FMRP-mediated immune resistance in this PDAC cancer cell line does not involve suppression of PD-1 or CTLA-4 immune checkpoint ligands.

Figures 3C, 3D:
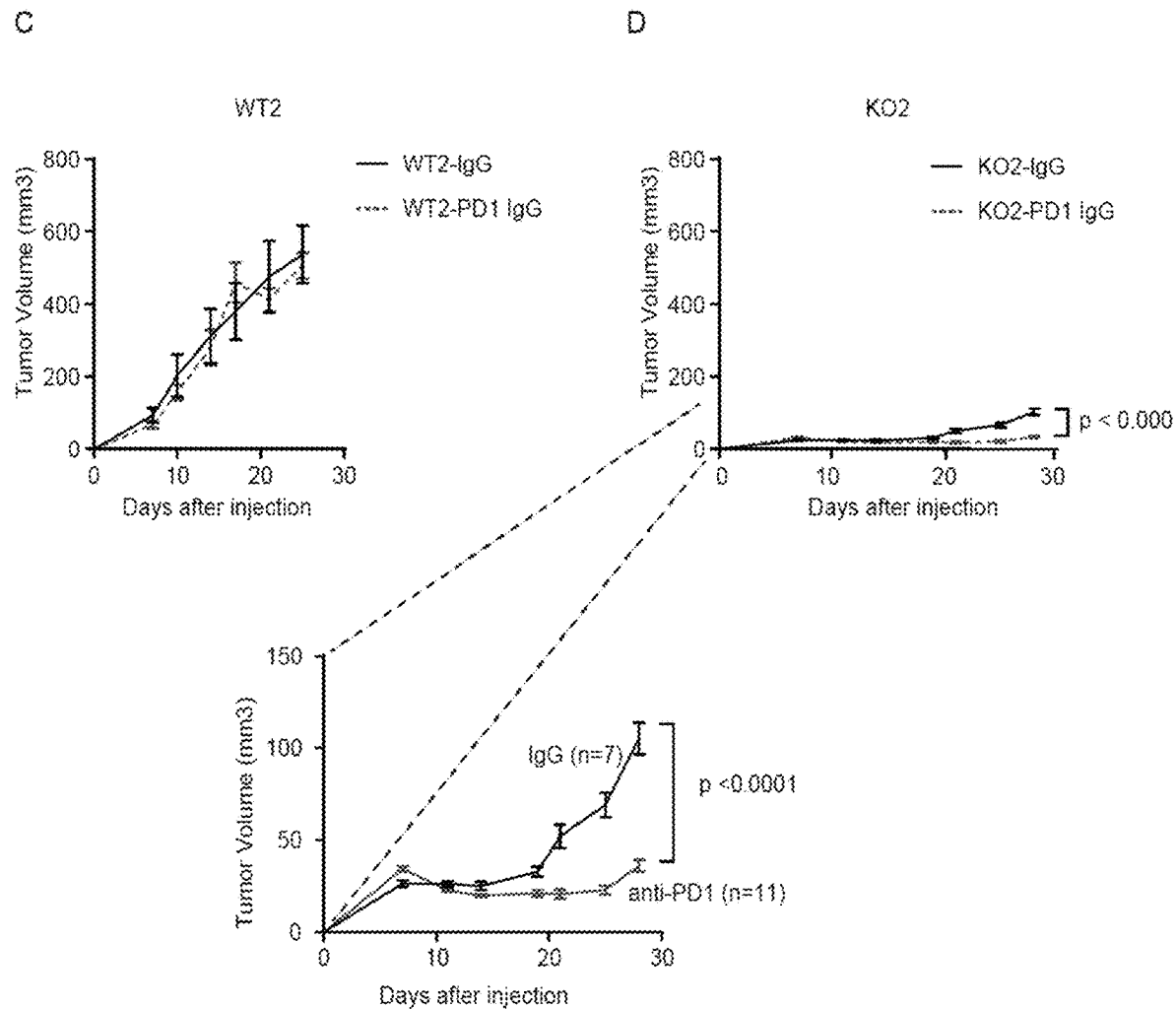

Additionally, we also performed a pre-clinical trial using anti-PD1 antibody on the WT tumors formed in immunocompetent FVBn mice, which revealed that WT PDAC tumors are non-responsive to anti-PD-1 therapy, recapitulating the unresponsiveness to anti-PD1 therapy in human PDAC patients (FIG. 3C). Despite this therapeutic resistance to anti-PD1 checkpoint immunotherapy, the derivative PDAC tumor cells with a KO of FMRP have strikingly impaires tumor growth in vivo (FIG. 1), which is associated with an influx of CD8 T cells (FIG. 2). The results suggest that FMRP inhibitors could be used as a novel immunotherapy strategy in the treatment of PDAC and other tumors that fail to respond to checkpoint inhibitors. Intringingly, PD1 antibody treatment in FMRP KO tumors further suppresses the tumor growth, indicating that the combination of anti-PD1 antibody with the FMRP knockout has combinatorial benefit in extending survival (FIG. 3D).

Figure 4A:
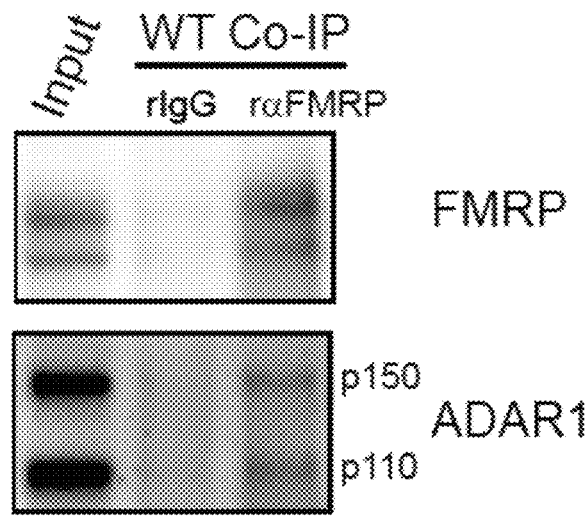
FIG. 4A-4D. Combined deletion of the genes encoding FMRP and the RNA A to I editing protein ADAR1 in mouse PDAC further prolongs survival. (A) FMRP and ADAR1 interact in PDAC cancer cells, as determined by co-immunoprecipitation experiments in mouse PDAC 4361.12 WT2 cells. FMRP and ADAR1 were visualized in a western blot on total cell lysate prior to and after immunoprecipitation with rabbit anti FMRP antibody (Abcam, ab191411). Normal rIgG antibody was used as control. Three independents experiments. (B) The FMRP-ADAR1 interaction was also vadified by a reverse co-immunoprecipitation experiment, wherein FMRP and ADAR1 were revealed by immunostaining western blots of total cell lysate prior to and after immunoprecipitation with mouse anti ADAR1 antibody (Santa Cruz, sc73408). Normal mIgG antibody was used as control. Three independents experiments. (C) Western blotting validation of FMRP and ADAR1 expression in WT2, FMRP KO, ADAR1 KO, and FMRP/ADAR1 double KO cells, which were generated by transient transfection with Cas9/SgRNA vectors targeting the mouse FMR1 and ADAR1 genes. Three independents experiments. (D) Overall survival of FVBn mice injected with WT2, FMRP KO, ADAR1 KO, and FMRP/ADAR1 double KO cells; the Kaplan-Meier test was used. In brief, $5\times10^5$ cells were s.c. injected into the flanks of FVBN mice. The mice were monitored twice per week, and sarcrified when tumor volumes reached 1000 mm^3.
Figure 4B:
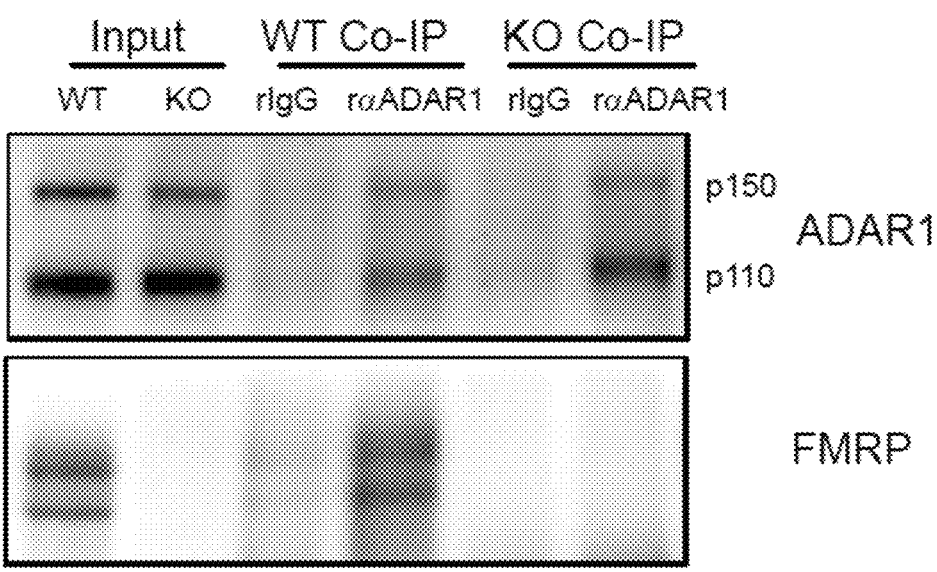
Figure 4C:
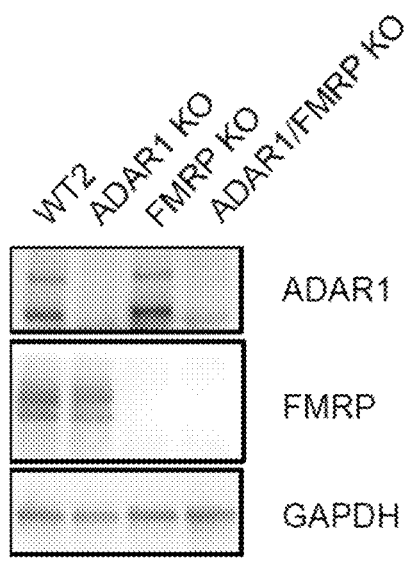
Figure 4D:
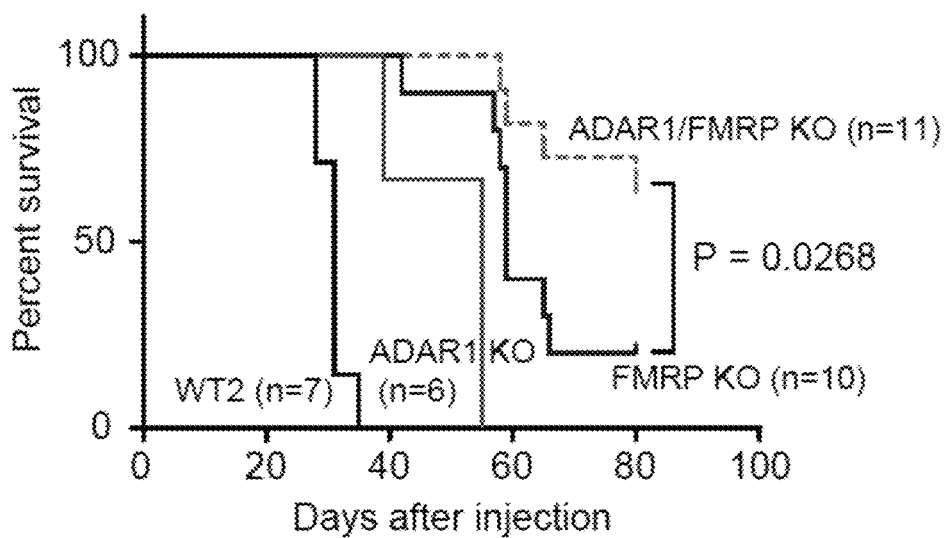

As a recent study shows ADAR1, an RNA-binding protein that mediates A-to-I RNA super-editing, promotes resistance to immune checkponit blockade.[23] Interestingly, another study shows that FMRP also regulates RNA surperdeiting in neurons by physically interacting with ADAR1. Strong interaction between FMRP and ADAR1 in mouse PDAC cells was confirmed by co-Immunoprecipitation (co-IP) and reverse co-IP (FIG. 4A-B). To determine whether the combination of FMRP and ADAR1 double KO would triggers much stronger anti-tumoral immune responses, ADAR1 single KO, and FMRP/ADAR1 double KO PDAC cells were genereated using transient transfection of Cas9/sgRNA vectors targeting FMR1 and ADAR1 gene (FIG. 4C), and were injected into the sygenenic mice. Intringingly, the combination of the FMRP and ADAR1 KO signifantly prolonged overall survival compared with the FMRP single KO and ADAR1 single KO groups (FIG. 4D), supporting the clinical application of the combination of targeting FMRP and ADAR1 in cancer immunotherapy.

Figure 5A:
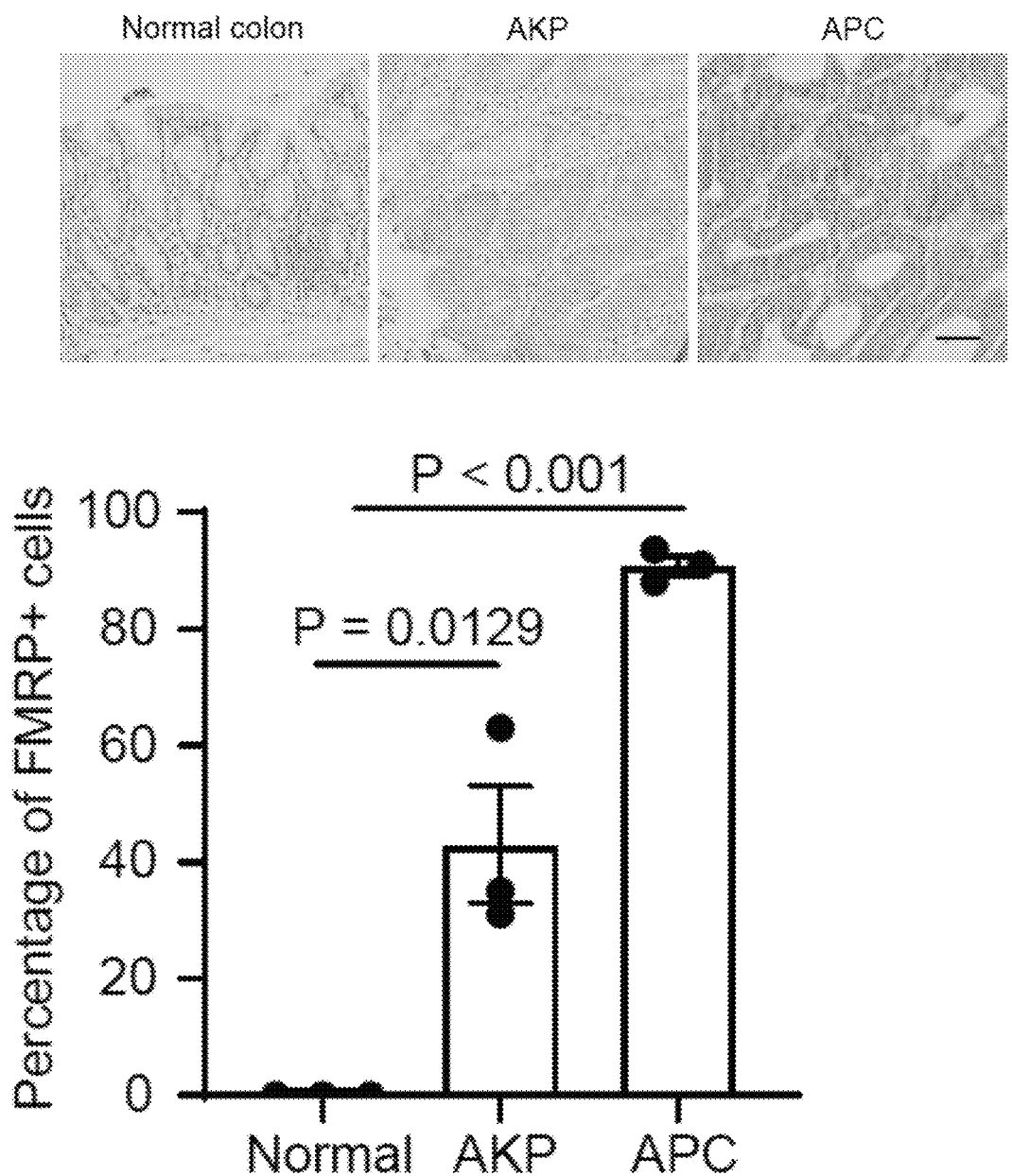
FIG. 5A-5I. Deletion of FMRP in cancer cells of a second tumor type, colon cancer, similarly impairs tumor growth in immunocompetent but not immunodeficient mice. (A) Representative images of immunohistochemistry staining and quantification of FMRP expression in mouse normal colon and adenomas tissues of AKP (ApcΔ/Δ;Kras$^{G12D/+}$;Trp53Δ/Δ; CDX2 Cre ERT2) or APC (ApcΔ/Δ; CDX2 Cre ERT2) mouse model. n=3 mice for each group. Student T-test was used. Scale bar, 100 μm. Immunostaining of human colon cancer tissue-microarrays (not shown) corroborates the mouse data. (B) Western blotting validation of FMRP expression in CT26 WT and FMRP KO subclones that were generated by transient transfection with Cas9/SgRNA vectors targeting the mouse FMR1 gene. The deletion of FMRP in CT26 cells were verified by two independent antibodies (Abcam, ab191411; Cell Signaling Technology, CST, #4317), which recognize different epitopes of FMRP protein. Three independents experiments. (C) Colony formation assay of CT26 WT17# and K012# cells. 1250 cancer cells were seeded in one well of a six-well plate. 10 days later, cells were fixed and stained using crystal violet; three independents experiments. (D) Schematic of the in vivo subcutaneous (s.c.) primary tumor growth model. In brief, $5\times10^5$ cells were injected s.c. into immunocompetent Balb/c or immunodeficient NSG mice. Mice were monitored twice per week, and sarcrified day 25 or 18 after the injection, when WT tumor volumes reachd 1000 mm^3. (E) Tumor growth curlve of Balb/c mice injected with CT26 WT17# or FMRP KO12# cells until day 25 after s.c. injection, n=10 mice per group, the unpaired T-test was used. (F) Representative images and tumor weight from Balb/c mice injected with CT26 WT17# or FMRP KO12# cells at day 25, n=10 mice per group, the unpaired T-test was used. (G) Immunochemical staining of CD8 and FMRP in primary tumors formed by CT26 WT17# or FMRP KO12# cells, scale bar, 100 μm, n=3 mice for each group (left panel); Quantification of CD8+ T cells in primary tumors formed by CT26 WT17# or FMRP KO12# cells (right panel); n=3 mice for each group. Student T-test was used. Scale bar, 100 μm. (H) Tumor growth curve of NSG mice injected with CT26 WT12# or FMRP KO12# cells until day 14 after s.c. injection, n=5 mice per group, the unpaired T-test was used. (I) Representative images and tumor weight from NSG mice injected with CT26 WT17# or FMRP KO12# cells at day 14, n=5 mice per group, the unpaired T-test was used.
Figure 5B:
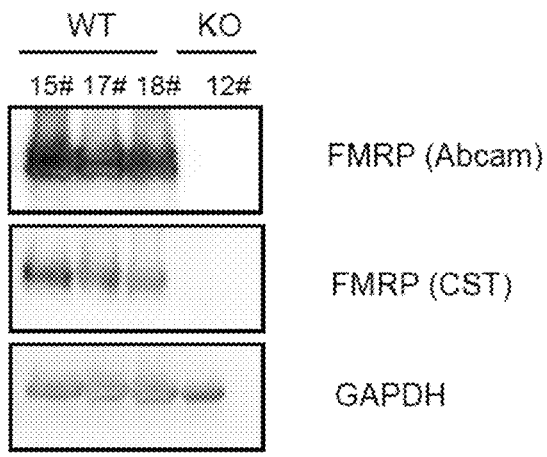
Figure 5C:
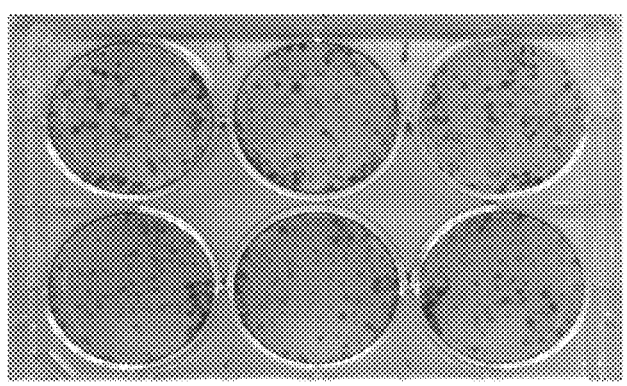
Figure 5D:
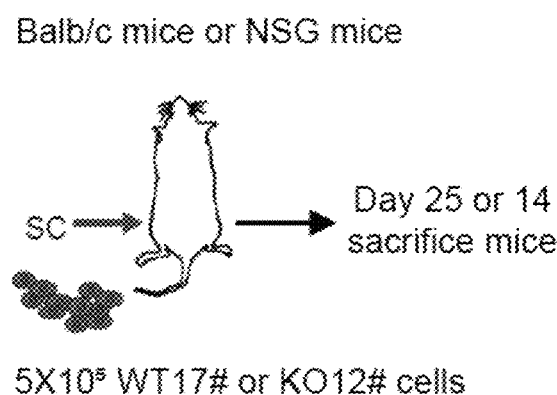
Figure 5E:
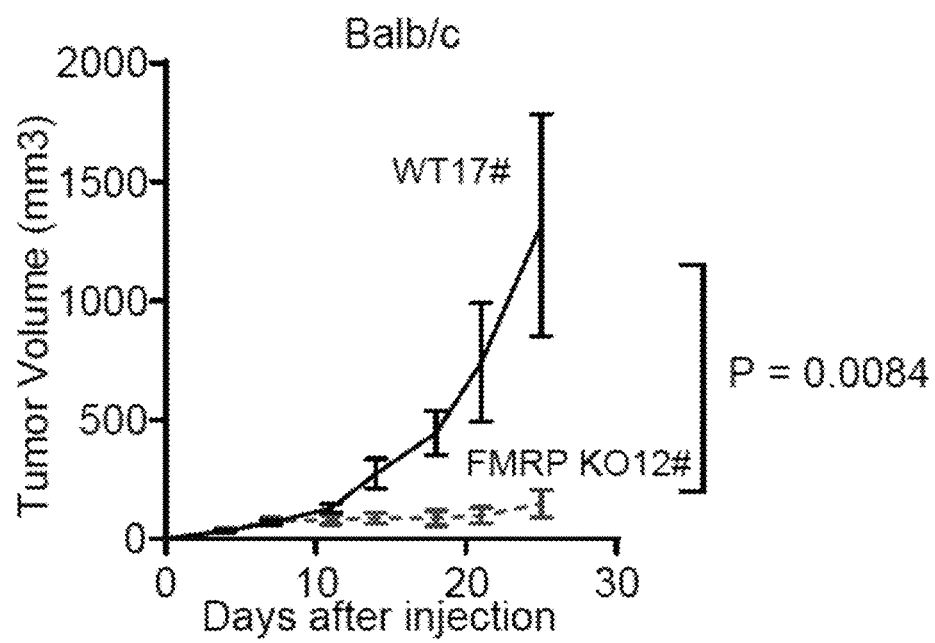
Figure 5F:
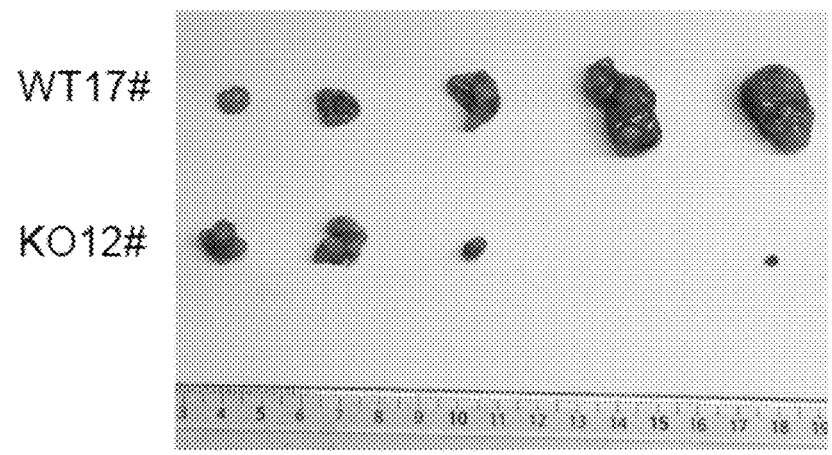
Figure 5F:
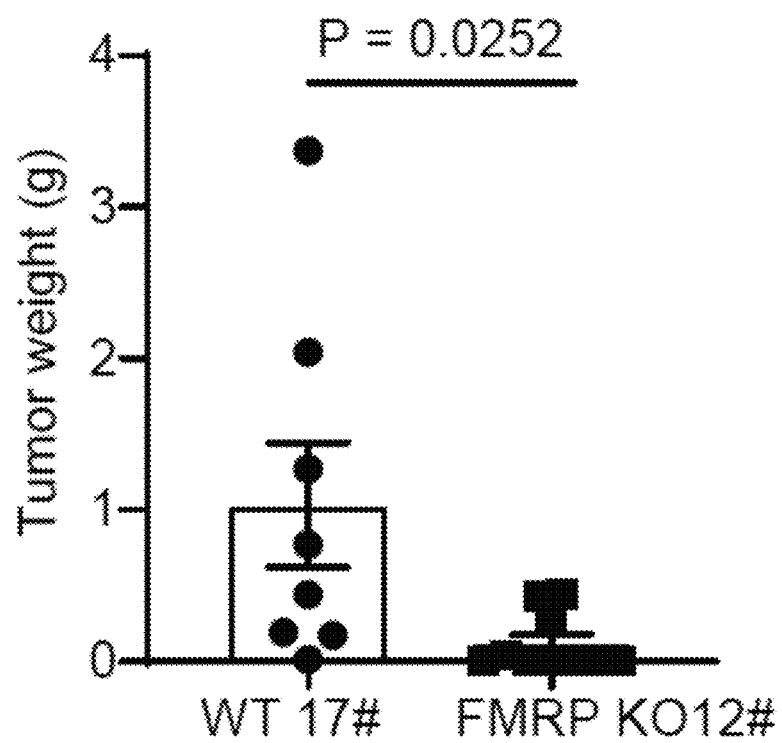
Figure 5G:
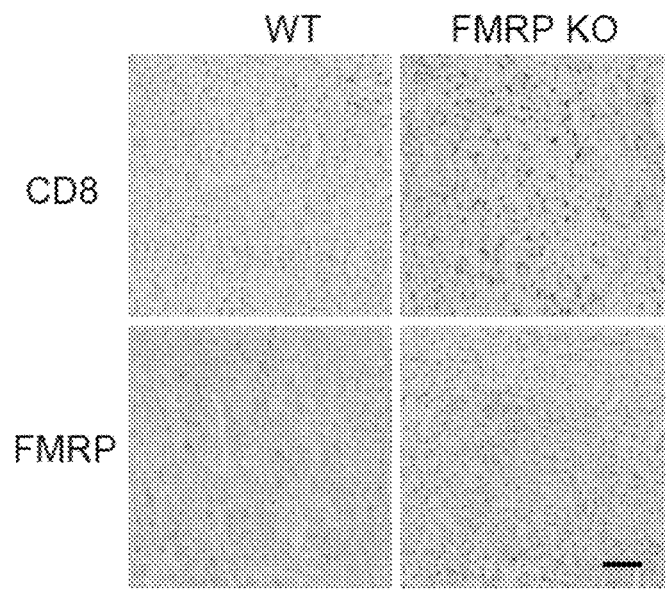
Figure 5G:
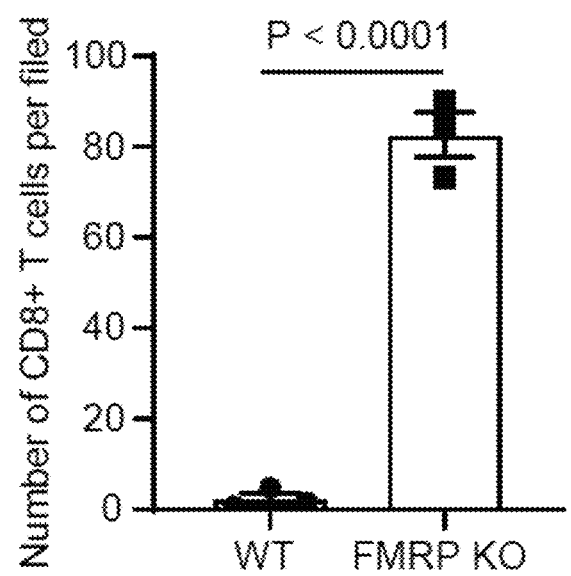
Figure 5H:
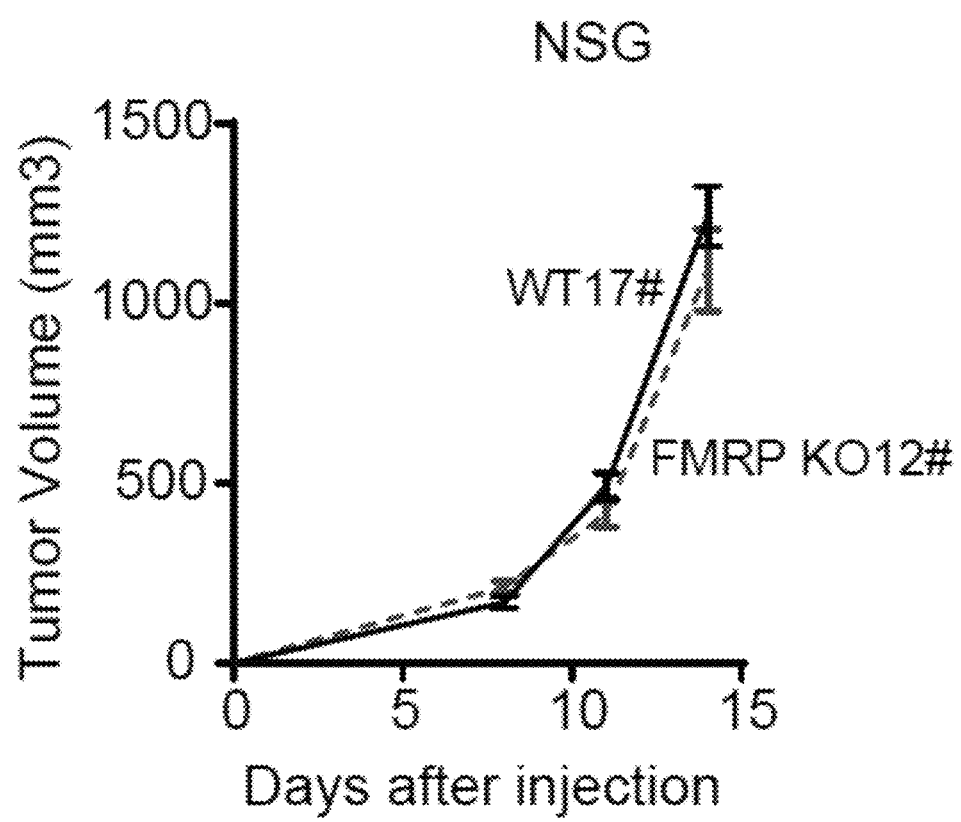
Figure 5I:
Figure 5I:
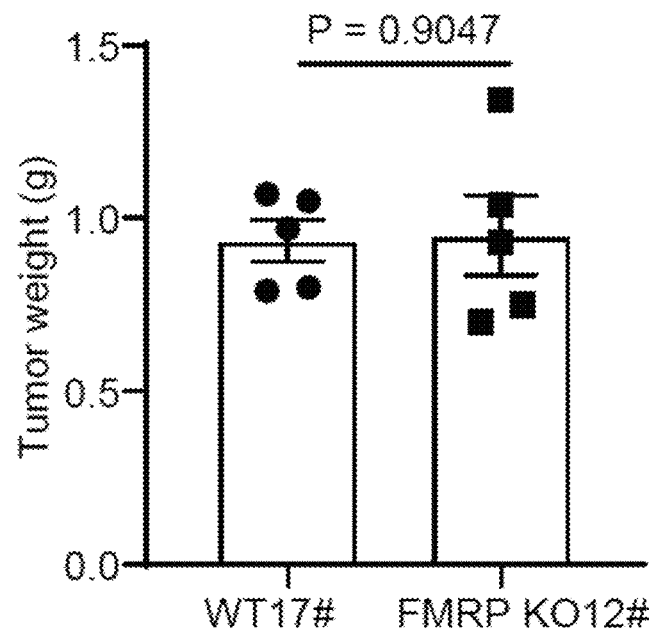
Figure 6A:
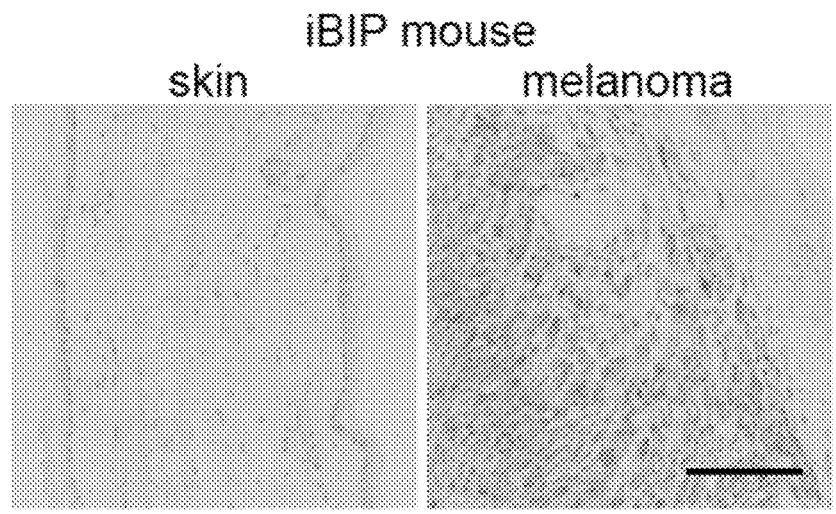
FIG. 6A-6E. Deletion of FMRP in mouse melanoma cells significantly impairs tumor growth in immunocompetent mice. (A) Representative images of immunohistochemistry staining and quantification of FMRP expression in mouse normal skin and melanoma tissues of the iBIP2 (inducible BRAF INK/ARF PTEN) melanoma mouse model in the FVBN background. n=2 mice for normal skin group and 4 mice for the iBIP2 melanoma group. Student T-test was used. Scale bar, 100 μm. (B) Western blotting validation of FMRP expression in B16-OVA WT and FMRP KO subclones that were generated by transient transfection with Cas9/SgRNA vectors targeting the mouse FMR1 gene. Three independents experiments. (C) Colony formation assay of B16-OVA WT and FMRP KO cells. 1250 cancer cells were seeded in one well of a six-well plate. 10 days later, cells were fixed and stained using crystal violet; three independents experiments. (D) Tumor growth curlve of C57B/6 mice injected with B16-OVA WT or FMRP KO cells until day 18 after s.c. injection, n=5~10 mice per group, the unpaired T-test was used. In brief, 5×10^5 cells were s.c. injected into the flanks of C57B/6 mice. Mice were monitored twice per week, and sarcrified on day 18 after the injection, when WT tumor volume reached 1000 mm^3. (E) Representative images and tumor weight from immunocompetent mice injected with B16-OVA WT or FMRP KO cells, collected at day 18, n=5~10 mice per group; the unpaired T-test was used.
Figure 6B:
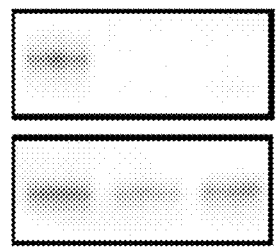
Figure 6C:
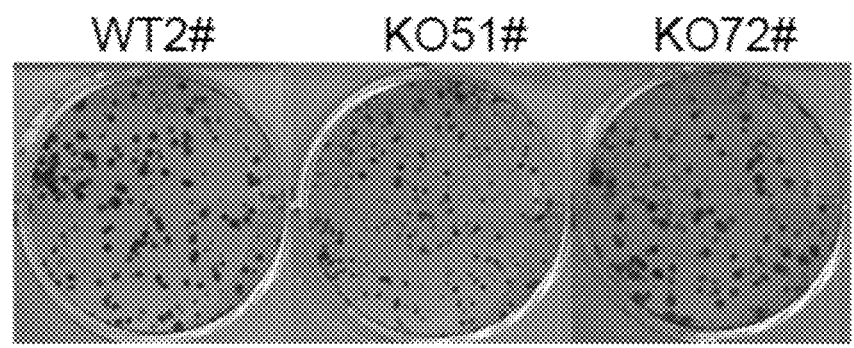
Figure 6C:
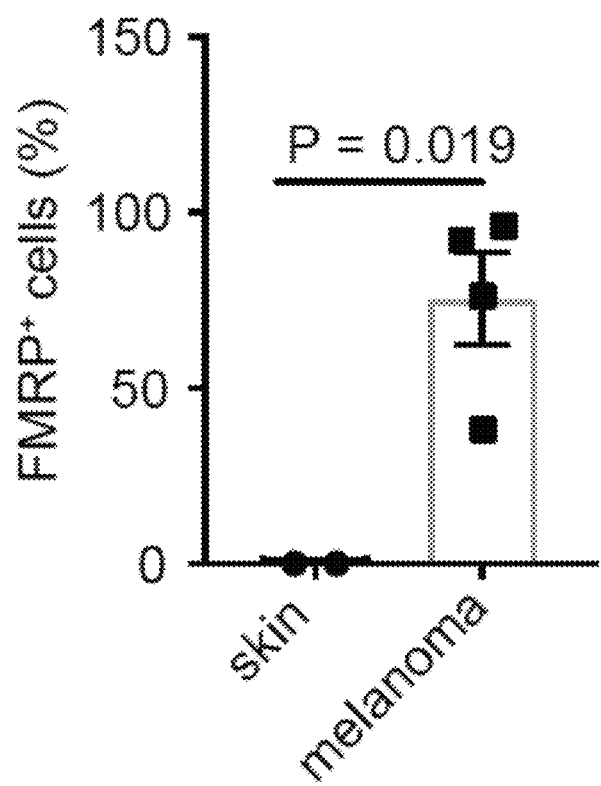
Figure 6D:
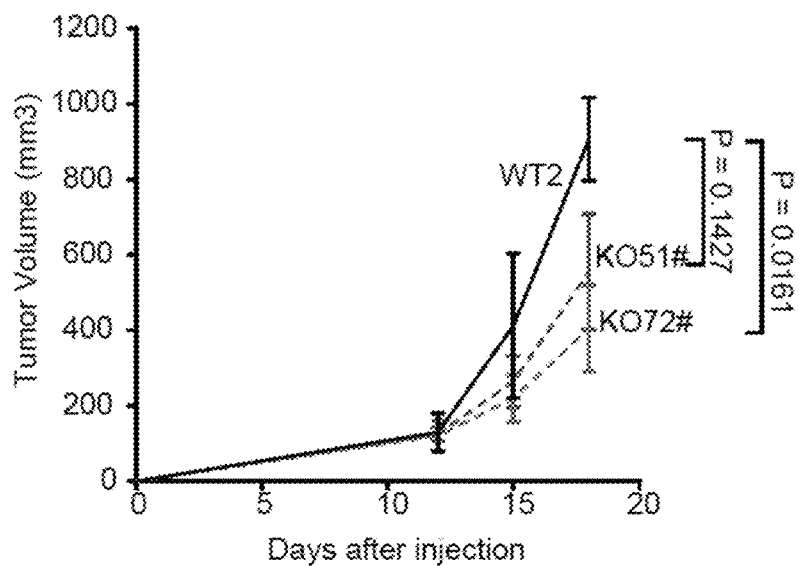
Figure 6E:
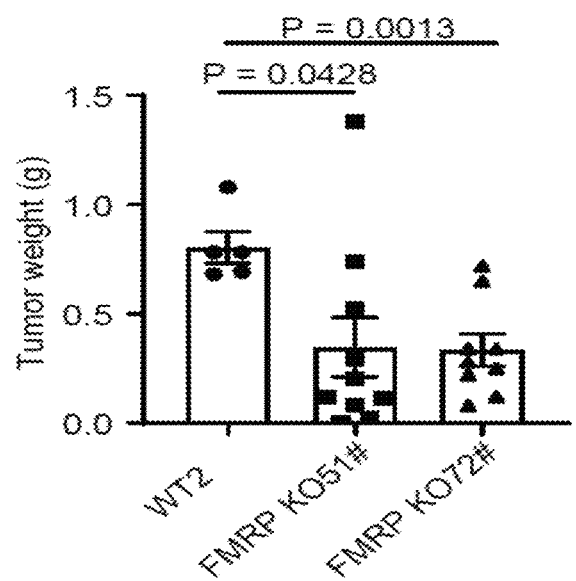
Figure 7A:
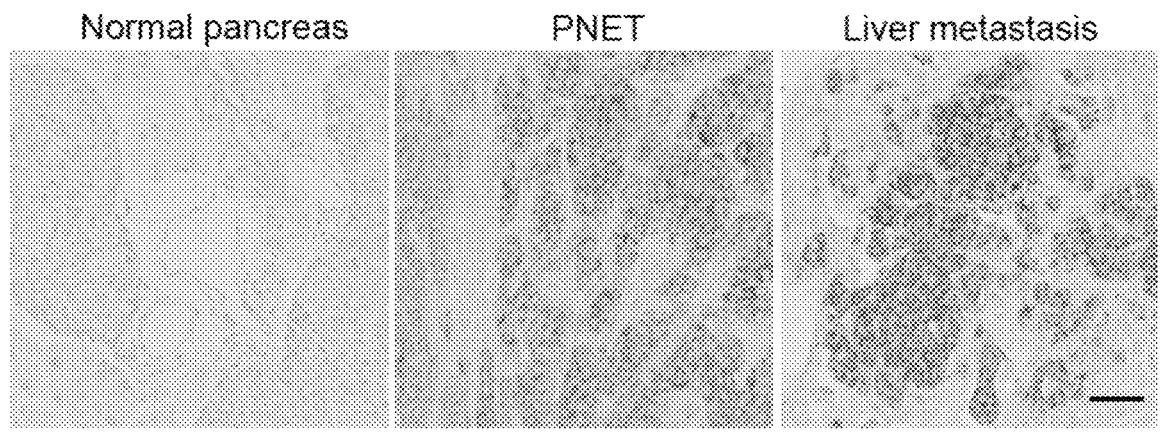
FIG. 7A and 7B. Specific deletion of FMRP in incipient cancer cells in the genetically engineered RIP1-Tag2 (RT2) mouse model of multistep pancreatic neuroendocrine tumorigenesis (PanNET) significantly prolongs survival. (A) Representative images of immunohistochemical staining of FMRP expression in mouse normal pancreas, PanNET tumors and liver metastasis; n=3 mice for each group. Scale bar, 100 μm. (B) Overall survival of male RT2 and FMRP KO RT2 mice, Kaplan-Meier test was used. Male FMRP KO RT2 mice, in which the FMR1 gene encoding FMRP was specially deleted in the pancreric islet β cells cells that express the oncogene SV40 driving PanNET tumorigenesis, were generated by crossing FMR1 foxed mice with Ripl-Tag 2 (RT2) and RIP7-Cre mice; n=17 for the FMRP KO RT2 group, and n=12 for the RT2 group. All the mice were monitored twice per week, and were sacrificed upon reacing a veterinary endpoint.
Figure 7B:
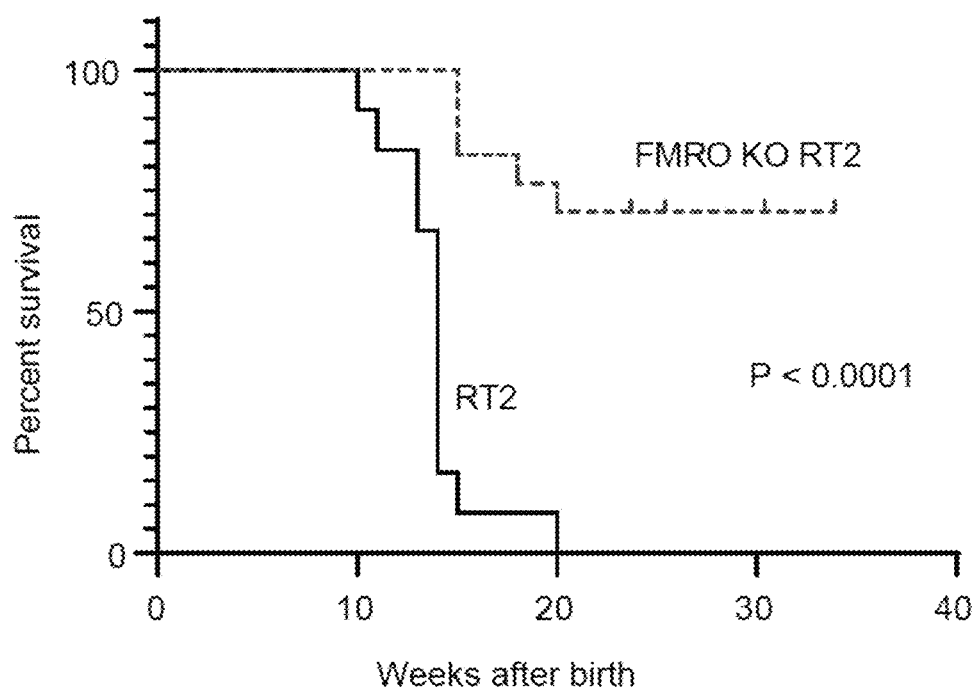
Figure 8A:
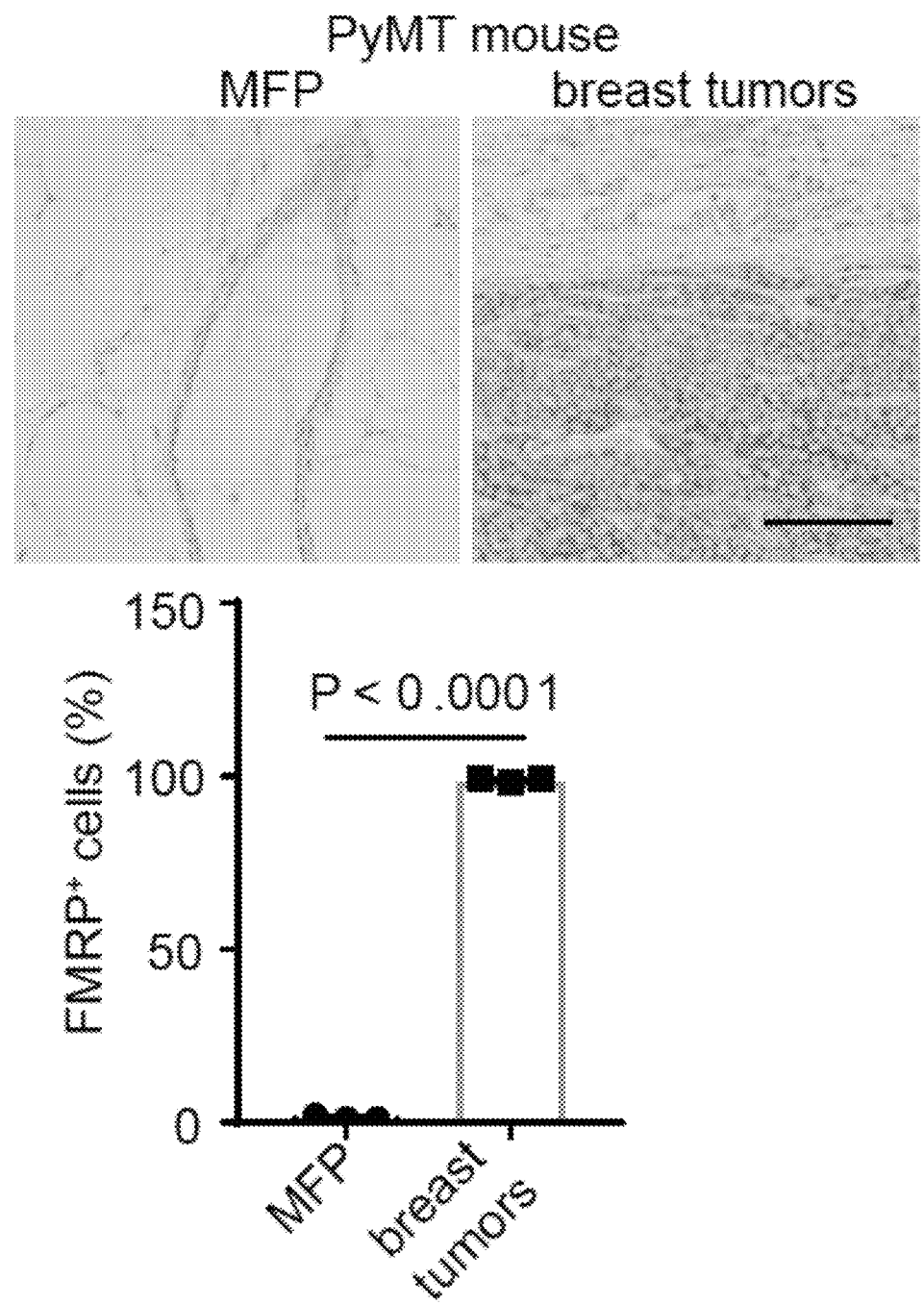
FIG. 8A and 8B. Elevated FMRP expression in mouse breast cancer tissues. (A) Representative images and quantification of FMRP expression in mouse normal mammary fat pat (MFP) and de novo breast tumors of the genetically engineered MMTV-PymT breast cancer mouse model. n=3 mice per group. Student T-test was used. Scale bar, 100 μm. (B) Representative images and quantification of FMRP expression in mouse normal mammary fat pat (MFP) and de novo breast tumors of the genetically engineered C3Tag triple-negative breast cancer (TNBC) mouse model. n=3 mice for normal MFP group and 3 mice for C3Tag breast cancer group. Student T-test was used. Scale bar, 100 μm. Immunostaining of human triple negative breast cancer (TNBC) tissue-microarrays (not shown) corroborates the results in mouse breast cancer.
Figure 8B:
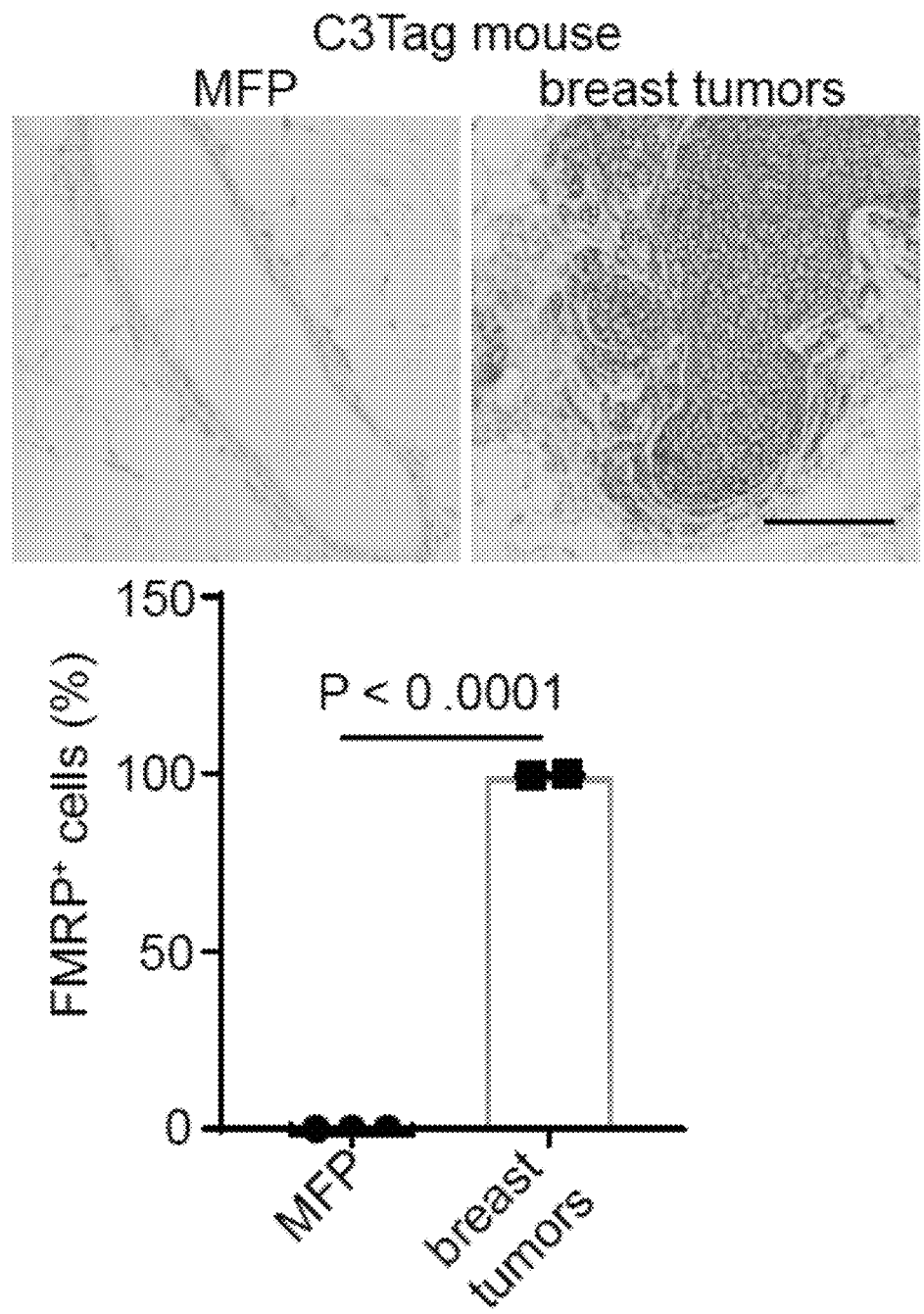

To more broadly explore the potential role of FMRP in suppression of anti-tumoral immunity in other types of cancer, dramatically increased FMRP expression in mouse colon tissue (FIG. 5A), melonoma tissues (FIG. 6A), pancreatic neuronendoccrine tumors (PNET) and liver metastasis (FIG. 7A), breast cancer tissues (FIG. 8A) compared with corresponding normal tissues was detected. Human data are consitent with the mouse data (not shown). Similarily, the FMRP KO in mouse colon cancer cells (FIG. 6B) and melanoma cells (FIG. 7B) does not significanity impair colony formation—reflecting proliferative and survival capabilitiues—in vitro. However, the FMRP KO severely impaired colon tumor growth in sygenic mice, but not in immunodeficient mice (FIG. 6D-I, FIG. 7D-E). Increased number of CD8 T cells were only found in FMRP KO colon tumors but not in WT tumors (FIG. 6G). FMRP was also knocked-out in PanNET tumors developing in the RIP1-Tag2 (RT2) PanNET mouse model by crossing RIP-7 cre mice with RT2 mice and FMR1-floxed mice. Importantly, FMRP KO RT2 mice have a significantly prolonged survial compared with WT RT2 mice, strongly suporting a role of FMRP in promoting PNET tumor progression.

Figure 11:
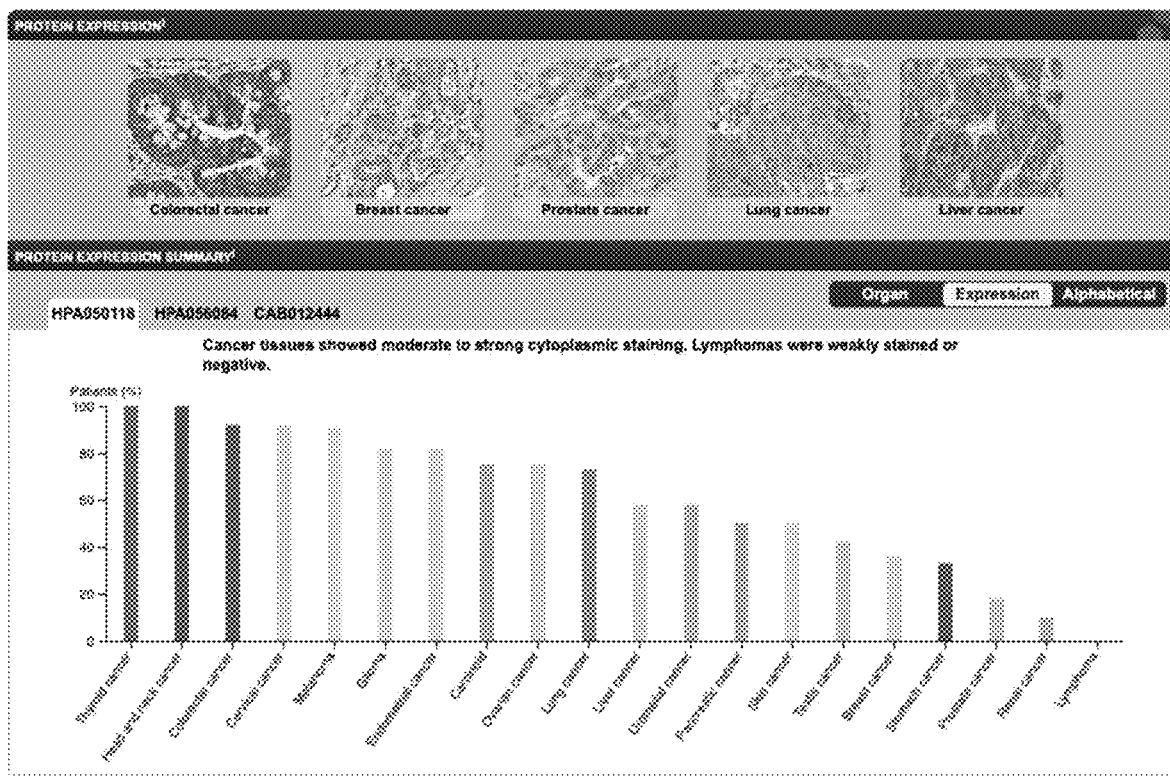
FIG. 11 demonstrates the widespread and highly prevalent expression of FMRP across the spectrum of human cancer types (reproduced from The Human Protein Atlas; proteinatlas.org/ENSG00000102081-FMR1/pathology).

Additional surveys of FMRP expression in human tumors revealed significant upragulation in 30-100% of patients with a broad spectrum of cancer types, including all of the major forms of lethal solid tumors (see e.g., FIG. 11).

Example 2

Direct Targeting of the RNA Binding Sites in FMRP using Oligonucleotides and Peptides to Disrupt Interactions Implicated in FMRP's Effector Function.

Figure 9A:
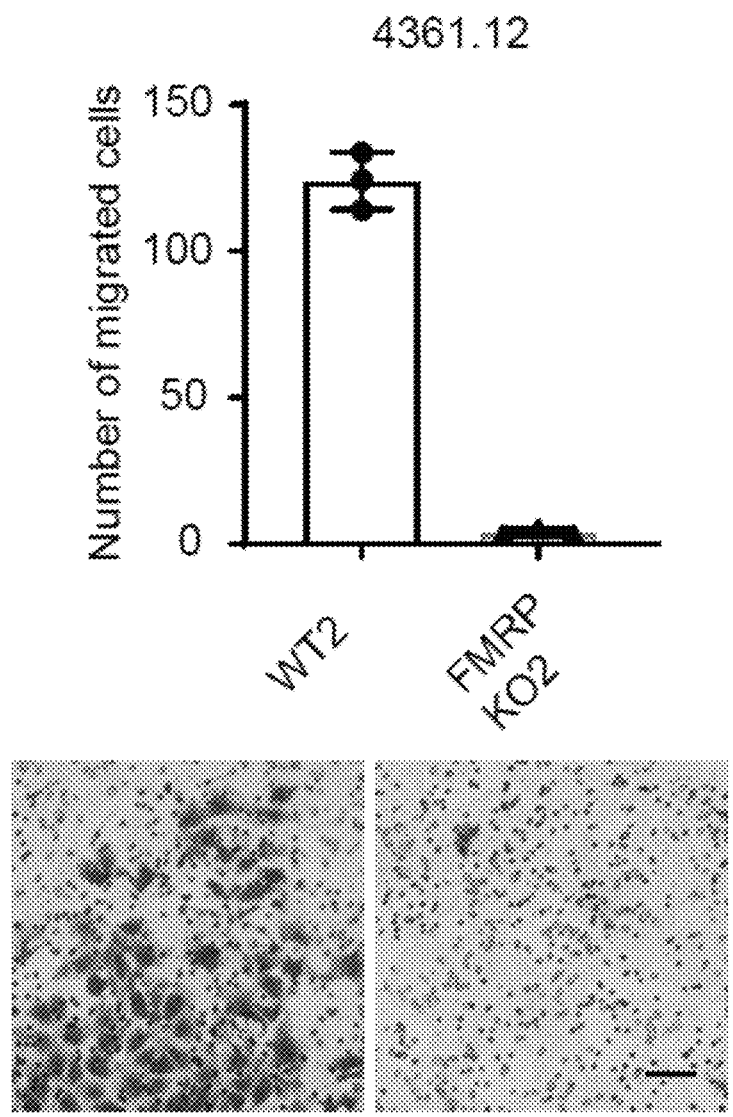
FIG. 9A-9C. Inhibition of FMRP in mouse PDAC cells via siRNAs. (A) Migration assay of mouse PDAC 4361.12 WT2 cells and FMRP KO2 cells. In brief, 5000 cells in 50 μl of serum-free DMEM medium were seeded in the top well of a Boyden chamber (pore size of the membrane, 8 μm), 200 μl DMEM medium with FBS were placed in the bottom chamber. 18 hours later, cancer cells remaining in the well were removed using cotton swabs with 70% EtOH. Those cells that migrated through the membrane via the 8-μm pores were fixed, and then stained with crystal violet. The number of migrated cells were counted. Data were collected from 3 independent wells. the unpaired T-test was used. Three independents experiments. (B) Western blotting validation of FMRP expression in mouse PDAC 4361.12 WT2 cells transfected with control siRNA (i.e., siCtrl: UAAGG CUAUG AAGAG AUAC (SEQ ID NO: 9)), and siRNAs targeting FMRP (siFMRP#1: AUAAG AGACA ACUUG GUGC (SEQ ID NO: 10); and siFMRP#2: UAACUUCG-GAAUUAUGUAG (SEQ ID NO: 11)). Three independents experiments. (C) Migration assay of mouse PDAC 4361.12 WT2 cells transfected with control siRNA, and siRNAs targeting FMRP; 5000 cells per well for 18 hr. Data were collected from 3 independent wells. the unpaired T-test was used. Three independents experiments.
Figure 9B:
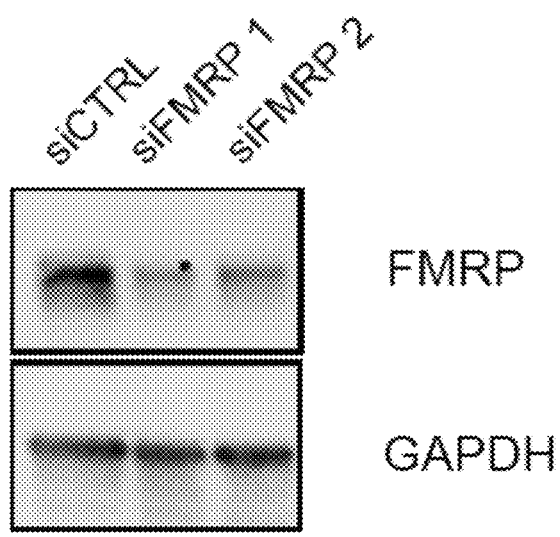
Figure 9C:
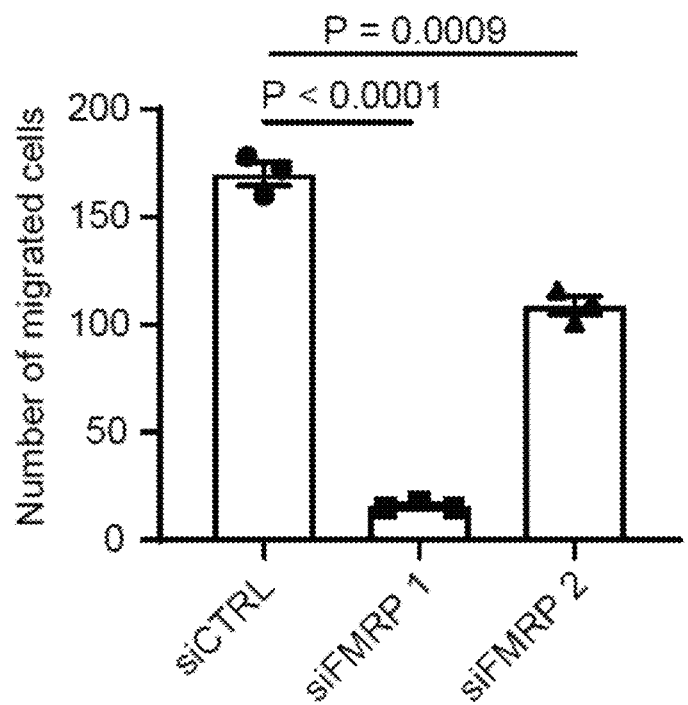

The RGG and KH2 RNA binding domains of FMRP have been implicated in its functional activities in multiple studies (e.g., Vasilyev, 2015; Darnell 2005), and disrupting FMRA-RNA interactions by delivery of an abundance of competitive molecules based on structural knowledge about these interactions. In one variation of the method, DNA or RNA oligonucleotides representing the core sequences from sc1/kc RNAs that bind to RGG/KH2 domains, respectively, would be synthesized. In some embodiments, locked nucleic acid (LNA) technology could be included in the synthesis, aiming to increase both half-life of the oligonucleotides and their binding affinity. In a second variation, polypeptides spanning the RGG and KH2 domains of FMRP would be synthesized and tested. In some embodiments, the polypeptides are combined by a polypeptide linker. In both variations, the candidates would be tested first by delivery into cultured cancer cells that express FMRP, scoring for impaired invasiveness in a Boyden chamber assay as previously described (Li & Hanahan 2013; Li, Zeng, et al 2018) and illustrated in FIG. 9. Candidate compounds would be inoculated into tumors composed on cancer cells expressing FMRP, such as those described in this application, assessing consequent infiltration of CD8 T cells, which are otherwise excluded by expression of FMRP. Variations on the method would employ transfection enhancers to increase uptake in tumors of the candidate oligonucleotides.

Example 3

Therapeutic Suppression of FMRP by siRNAs

An increasingly well validated therapeutic strategy involves the delivery of siRNAs that bind to and destabilize or block translation of mRNAs into tissue of, so as to suppress production of proteins implicated in disease (Selvam 2017). In this method, siRNAs are designed to bind to and disrupt FMR1 mRNA (encoding FMRP) and assayed by delivery into FMRP tumors devoid of CD8 T cells. scoring for infiltration of such cells, using the gene knockout tumors described elsewhere in this application as a benchmark. Prior to such in vivo testing, candidate siRNAs (i.e., siCtrl: UAAGG CUAUG AAGAG AUAC (SEQ ID NO: 9; siFMRP#1: AUAAG AGACA ACUUG GUGC (SEQ ID NO: 10); and siFMRP#2: UAACUUCGGAAUUAUGUAG (SEQ ID NO: 11)) were tested in the cancer cell invasion assay, where the inhibitory capability of a prototypical siRNA to FMR1 mRNAare illustrated in FIG. 9. In some embodiments, siRNAs to FMR1 could include additional refinements by, for example, chemical modifications to enhance stability and activity (Hassler 2018) and/or the use of 'transfection' reagents for enhancing the delivery of nucleic acids into cancer cells in tumors.

Example 4

Illustration of a High Throughput Biochemical Screening Method for Identifying Small Molecules that Bind to a Key Interaction site on FMRP.

One well-described mode of interaction of FMRP involves its regulation of a select set of mRNAs that contain a G-quadruplex motif that binds to a domain called RGG on the FMRP protein. Binding of the G-quadruplex motif result is alterations in translation of the targeted mRNA. An RNA called sc1 binds tightly to the RGD domain of FMRP and is widely used as a prototype for FMRP's binding to target mRNAs. As such, compounds that disrupt the binding of scl RNA to FMRP could represent a) inhibitors of translational control mechanisms involving FMRP binding to mRNAs, and b) tight binders to the RGG site that do not necessarily inhibit all FMRP functions, in the case that other mechanisms of action of FMRP beyond the RGG domain are involved in its newly discovered immuno-suppressive activity.

A second mode of FMRP interaction involves its binding to high affinity RNA targets through its KH2 RNA binding domain (Darnell et al., 2005). Studies have identified a series of RNAs that had structural and sequence-specific features termed "kissing complex (kc) RNAs. For example, kc2 RNA is able to compete FMRP off of polyribosomes at half maximal concentration of ~100 nM. Human and mouse studies have shown that single missense mutations in KH2 abrogate FMRP polysome association and cause severe forms of the Fragile-X syndrome. Compounds that disrupt binding of kcRNA to FMRP could disrupt FMRP polysome association and abrogate function. Such compounds could be an agent as disclosed herein. In some embodiments, the agent is a synthetic nucleic acids that disrupts binding of kcRNA to FMRP. In some embodiments, a synthetic nucleic acid could be used as benchmarks to screen for and identify other kinds of small molecule inhibitors that act to disrupt FMRP function.

Figure 10A:
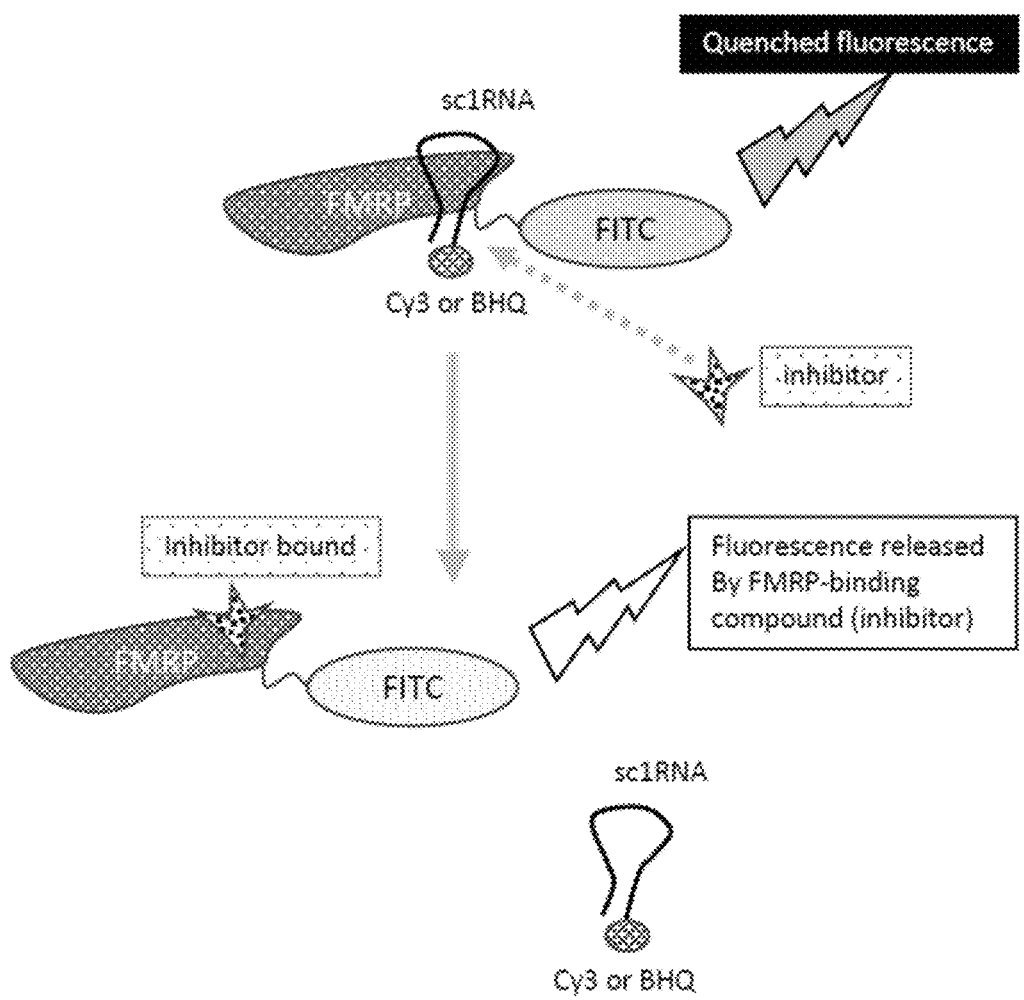
FIG. 10A and 10B. FRET-based high-though screen (HTS) for FMRP inhibitors A. Schematic of FRET-based high-though screen (HTS) for FMRP inhibitors. Human FMRP protein is produced in human HEK 293 cells, purified, and biochemically labeled with the fluorescent reporter fluorescein. 2) The sc1 RNA1 is labeled with a fluorescence quencher molecule, either Cy3 or BHQ, such that when sc1 is bound to FMRP, the excitable fluorescence emission of FITC is quenched. 3) Compounds that elicit the release of the quenched fluorescence are subjected to further characterization to validate their capability to disrupt the interaction of FMRP and sc1. B. Mammalian expressed FMRP-His protein purification profile. Human FMRP protein is produced in human HEK 293 cells, purified and validated. Left panel, Coomassie blue staining showing 2 ug total protein in each lane. Right panel, Western blot of FMRP-His protein expression by using anti-His Tag antibody. M. Molecular weight marker. Me. Culture medium. FT. Flow through. W. Washes. E. Eluted fractions. Eluted fractions were pooled, buffer exchanged and concentrated.
Figure 10B:
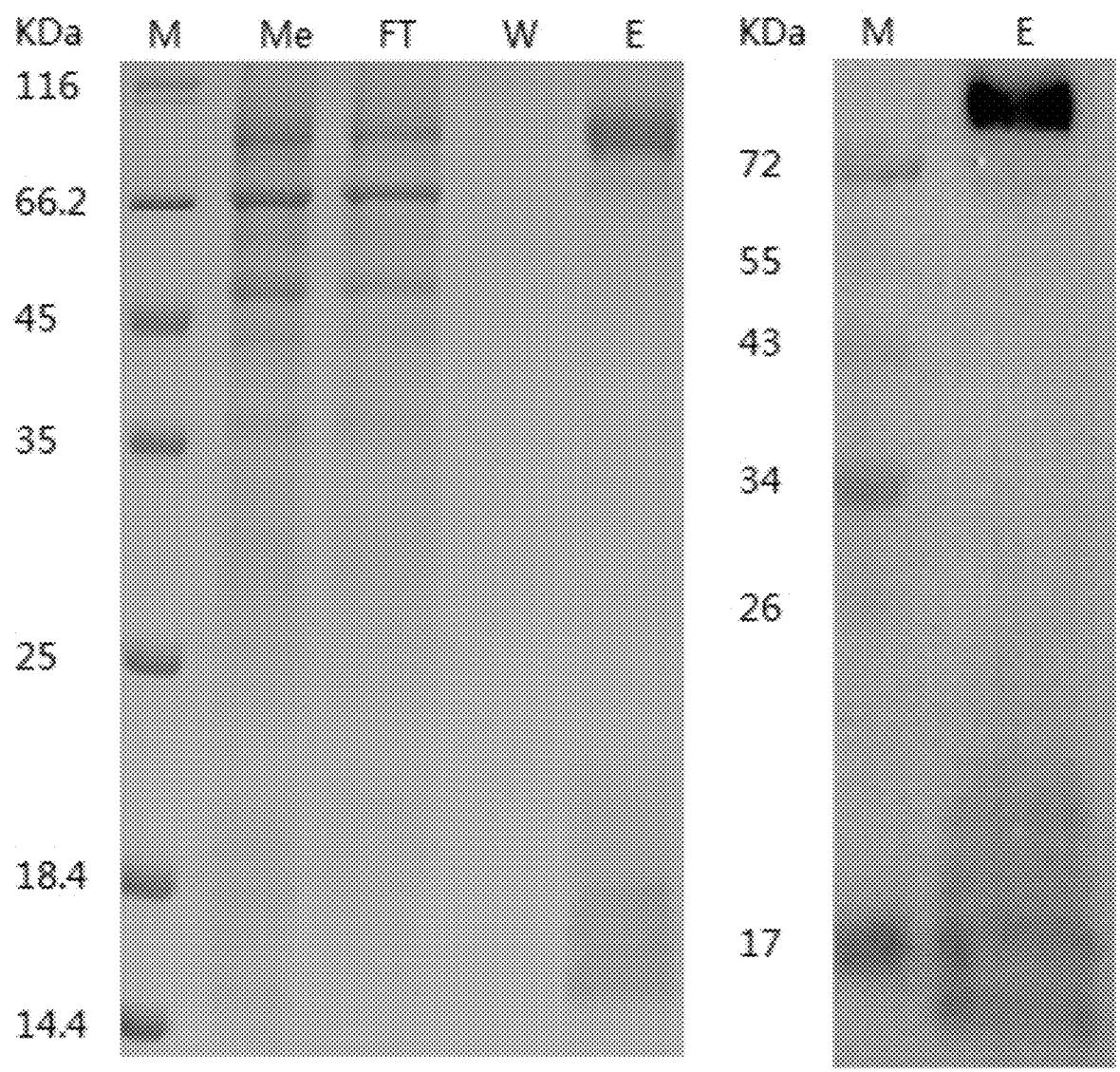

Any suitable assay known in the art to identify inhibitors of RNA-binding proteins can be used to screen compound libraries for small molecules that interfered with binding of FMRP to its distinctive target mRNAs (see e.g., Roos et al 2016). The readout involved identification of compounds that, upon binding, release fluorescent quenching of a fluorophore covalently attached to the protein, whose emission is otherwise blocked by the bound target RNA molecule that is modified to carry a fluorescence quencher. As applied to FMRP, the method would be performed as follows, and schematically illustrated in FIG. 10.

For example, 1) human FMRP protein is produced in human HEK 293 cells, purified, and biochemically labeled with the fluorescent reporter fluorescein. 2) The sc1 RNA would be labeled with a fluorescence quencher molecule, for example Cy3 or BHQ, such that when sc1 is bound to FMRP, the excitable fluorescence emission of FITC is quenched. 3) FITC-FMRP and sc1-Cy3/BCG would be combined and aliquoted into 384 well microwells, after which chemical compounds from large compound libraries would be added to each well. The assay would best be performed in an HTP screen facility, where robots would prepare the micro-wells containing the protein/RNA complex, add coded compounds to each well, and then read out fluorescence emissions. 4) Compounds that elicited the release of the quenched fluorescence would be subjected to further characterization to validate their capability to disrupt the interaction of FMRP and sc1. 5) Such 'leads' would then be further characterized, to reveal binding affinity and kinetic parameters using microscale thermophoresis (MST) measurements and biolayer Interferometry (BLI by ForteBio-Octet). The newly identified compounds will be further characterized by biochemical, structural and cell-based assays, and in tumor models, to ascertain whether the compounds inhibit FMRP's functions and/or binds tightly to FMRP protein irrespective of functional inhibition. Tight binders could become components of protein degradation molecules designed to selectively degrade FMRP protein, irrespective of whether the compound proved to be a functional inhibitor itself.

Example 5

Identifying Compounds that Inhibit Expression of FMRP/FMR1.

Cancer cells expressing high levels of endogenous FMRP protein and mRNA would be engineered with an FMRP promoter driving GFP, along with a ubiquitous promoter driving RFP. Cell based HTP screens would be performed, scoring for compounds that suppress green fluorescence (FMRP transcription) but not red fluorescence (cell viability). Initial hits would be filtered by immuno-staining for endogenously expressed FMRP since bona fide inhibitors of FMR1 transcription should suppress not only the reporter gene but FMR1 itself. A variation would be to engineer the cell line with a FMRP Promoter driving a fusion gene composed of FMRP and GFP, which could also score for translational and protein stability inhibitors. Methodology for HTP cell-based screens to identify transcriptional inhibitors are increasing being successfully applied (see e.g., Zhang, 2018; Vuong, 2016).

REFERENCES

1. Hargadon et a., Immune checkpoint blockade therapy for cancer: An overview of FDAapproved immune checkpoint inhibitors. International Immunopharmacology 62: 29-39 (2018).
2. Schoenfeld and Hellman, Acquired Resistance to Immune Checkpoint Inhibitors. Cancer Cell 37: 443-455 (Apr.13, 2020).
3. Royal, R. E. et al. Phase 2 trial of single agent Ipilimumab (anti-CTLA-4) for locally advanced or metastatic pancreatic adenocarcinoma. *J Immunother.* 33, 828-833 (2010).
4. Brahmer, J. R. et al. Safety and Activity of Anti-PD-L1 Antibody in Patients with Advanced Cancer. *New England Journal of Medicine* 366, 2455-2465 (2012).
5. Li, L. et al. GKAP Acts as a Genetic Modulator of NMDAR Signaling to Govern Invasive Tumor Growth. *Cancer Cell* 0, (2018).
6. Bassell, G. J. & Warren, S. T. Fragile X Syndrome: Loss of Local mRNA Regulation Alters Synaptic Development and Function. *Neuron* 60, 201-214 (2008).
7. Santoro, M. R., Bray, S. M. & Warren, S. T. Molecular Mechanisms of Fragile X Syndrome: A Twenty-Year Perspective. *Annu. Rev. Pathol. Mech. Dis.* 7, 219-245 (2012).
8. Lucá, R. et al. The Fragile X Protein binds mRNAs involved in cancer progression and modulates metastasis formation. *EMBO Molecular Medicine* 5, 1523-1536 (2013).
9. Jeon, S. J. et al. Cellular stress-induced up-regulation of FMRP promotes cell survival by modulating PI3K-Akt phosphorylation cascades. *Journal of Biomedical Science* 18, 17 (2011).
10. Mali, P. et al. RNA-Guided Human Genome Engineering via Cas9. *Science* 339, 823-826 (2013).
11. Vasilyev, N. et al. Crystal structure reveals specific recognition of a G-quadruplex RNA by a β-turn in the RGG motif of FMRP. Proc. Natl. Acad. Sci. 112, E5391-E5400 (2015).
12. Roos, M. et al. A Small-Molecule Inhibitor of Lin28. ACS Chem. Biol. 11, 2773-2781 (2016).
13. Darnell J C, Fraser C E, Mostovetsky O, Stevani G, Jones T A, Eddy S R and Darnell R B. (2005) Kissing complex RNAs mediate interaction between the Fragile-X mental retardation protein KH2 domain and brain polyribosomes. Genes Dev 19:903-918.
14. Vasilyev N, Polonskaia A, Darnell J C, Darnell R B, Patel D J, Serganov A. (2015). Crystal structure reveals specific recognition of a G-quadruplex RNA by a β-turn in the RGG motif of FMRP. Proc Natl Acad Sci USA. 112(39): E5391-400. doi: 10.1073/pnas.1515737112.
15 Li, L., & Hanahan, D. (2013). Hijacking the neuronal NMDAR signaling circuit to promote tumor growth and invasion. Cell. 153: 86-100.
16. Li, L., Zeng, Q., Bhutkar, A., Galvan, J., Karamitopoulou, E., Noordermeer, D., Peng, M. W., Piersgilli, A., Perren, A., Zlobec, I., Robinson, H., Iruela-Arispe, M. L., & Hanahan D. (2018) GKAP acts as a genetic modulator of NMDAR signaling to govern invasive tumor growth. Cancer Cell, 33: 736-751.
17. Roos M, Pradère U, Ngondo R P, Behera A, Allegrini S, Civenni G, Zagalak J A, Marchand J R, Menzi M, Towbin H, Scheuermann J, Neri D, Caflisch A, Catapano C V, Ciaudo C, Hall J. (2016) A Small-Molecule Inhibitor of Lin28. ACS Chem Biol. 11(10): 2773-2781. doi: 10.1021/acschembio.6b00232.
18. Darnell J C, Fraser C E, Mostovetsky O, Stevani G, Jones T A, Eddy S R and Darnell R B. (2005) Kissing complex RNAs mediate interaction between the Fragile-X mental retardation protein KH2 domain and brain polyribosomes. Genes Dev 19:903-918.
19. Hassler M R, Turanov A A, Alterman J F, Haraszti R A, Coles A H, Osborn M F, Echeverria D, Nikan M, Salomon W E, Roux L, Godinho B M D C, Davis S M, Morrissey D V, Zamore P D, Karumanchi S A, Moore M J, Aronin N, Khvorova A. (2018). Comparison of partially and fully chemically-modified siRNA in conjugate-mediated delivery in vivo. Nucleic Acids Res.; 46(5):2185-2196. doi: 10.1093/nar/gky037. PMID: 29432571.
20. Selvam C, Mutisya D, Prakash S, Ranganna K, Thilagavathi R. (2017) Therapeutic potential of chemically modified siRNA: Recent trends. Chem Biol Drug Des. 2017 November; 90(5):665-678. doi: 10.1111/cbdd.12993. Epub 2017 May 16. PMID: 28378934.
21. Zhang H, et al, Issa J J. 2018 Targeting CDK9 Reactivates Epigenetically Silenced Genes in Cancer. Cell 175 (5):1244-1258.e26. doi: 10.1016/j.cell.2018.09.051. PMID: 30454645.
22. Vuong W, Tew B Y, Little G H, Frenkel B, Jones J O. (2016). High-Throughput Screen for Inhibitors of Androgen Receptor-RUNX2 Transcriptional Regulation in Prostate Cancer. J Pharmacol Exp Ther. 359(2):256-261. doi: 10.1124/jpet.116.234567. PMID: 27554677.
23. Ishizuka et al., Loss of ADAR1 in tumours overcomes resistance to immune checkpoint blockade. Nature. 2019 January; 565(7737):43-48. doi: 10.1038/s41586-018-0768-9. Epub 2018 Dec. 17. PMID: 30559380.
24. Tran et al., Widespread RNA editing dysregulation in brains from autistic individuals. Nat Neurosci. 2019 January; 22(1):25-36. doi: 10.1038/s41593-018-0287-x. Epub 2018 Dec. 17. PMID: 30559470.

What is claimed:

1. A method for the treatment of cancer and/or the treatment and/or prevention of cancer metastasis in a subject in need thereof, the method comprising administering to said subject a nucleic acid that decreases the expression of an mRNA encoding fragile X mental retardation protein (FMRP) or fragile X mental retardation 1 (FMR1) gene, wherein the cancer and/or cancer metastasis is intrinsically resistant to or has acquired adaptive resistance to immunotherapy; wherein the nucleic acid is selected from the group consisting of an siRNA, an sgRNA, CRISPR-based loss-of-function system, an esiRNA, an shRNA, and an antisense oligonucleotide, or a combination thereof.

2. The method of claim 1, wherein said nucleic acid inhibits the translation of an RNA encoding FMRP.

3. The method of claim 1, wherein the nucleic acid inhibits the transcription of the FMR1 gene encoding FMRP.

4. The method of claim 1, wherein the nucleic acid inhibits or impairs the binding of the FMRP to a target mRNA.

5. The method of claim 1, wherein a plasmid or a vector comprises the nucleic acid.

6. The method of claim 5, wherein a host cell comprises the plasmid or vector.

7. The method of claim 1, wherein the decrease of the expression of the mRNA encoding FMRP or the FMR1 gene reduces FMRP suppression of anti-tumor immunity.

8. The method of claim 1, wherein a host cell comprises the nucleic acid.

9. A method for the treatment of cancer and/or the treatment and/or prevention of cancer metastasis in a subject in need thereof, wherein the cancer and/or cancer metastasis is intrinsically resistant to or has acquired adaptive resistance to immunotherapy, the method comprising administering to said subject a pharmaceutical composition comprising:

i) a therapeutically effective amount of a nucleic acid that decreases the expression of an mRNA encoding fragile X mental retardation protein (FMRP) or fragile X mental retardation 1 (FMR1) gene, wherein the nucleic acid is selected from the group consisting of an siRNA, an sgRNA, CRISPR-based loss-of-function system, an esiRNA, an shRNA, and an antisense oligonucleotide, or a combination thereof; or ii) a plasmid or a vector comprising one or more nucleic acid(s) encoding a siRNA, sgRNA, CRISPR-based loss-of-function system, esiRNA, shRNA, and/or antisense oligonucleotide, or a combination thereof; or iii) a host cell comprising the plasmid or vector or one or more nucleic acid(s) encoding the siRNA, sgRNA, CRISPR-based loss-of-function system, esiRNA, shRNA, and/or antisense oligonucleotide, or a combination thereof;

and a pharmaceutically acceptable carrier or diluent.

10. The method of claim 9, wherein the pharmaceutical composition further comprises one or more anti-cancer therapy.

11. The method of claim 10, wherein the one or more anti-cancer therapy comprises a therapeutically effective amount of an immune checkpoint inhibitor.

12. The method of claim 11, wherein the immune checkpoint inhibitor is selected from the group comprising a PD-1 inhibitor, a PD-L1 inhibitor, and a CTLA-4 inhibitor, or a combination thereof.

13. The method of claim 10, wherein the one or more anti-cancer therapy directed at FMRP is included in combination with a therapeutically effective amount of an anti-tumor-vaccine, including personalized neo-antigen cocktails, or other immune-stimulatory agents that bolster anti-tumor immune responses.

* * * * *

SEQUENCE LISTING

```
<160> NUMBER OF SEQ ID NOS: 17

<210> SEQ ID NO 1
<211> LENGTH: 4140
<212> TYPE: DNA
<213> ORGANISM: Artificial Sequence
<220> FEATURE:
<223> OTHER INFORMATION: Synthetic nucleotide

<400> SEQUENCE: 1
acttccggtg gagggccgcc tctgagcggg cggcgggccg acggcgagcg cgggcggcgg      60
cggtgacgga ggcgccgctg ccaggggcg tgcggcagcg cggcggcggc ggcggcggcg     120
gcggcggcgg aggcggcggc ggcggcggcg gcggcggcgg ctgggcctcg agcgcccgca     180
gcccacctct cggggcggg ctcccggcgc tagcagggct gaagagaaga tggaggagct     240
ggtggtggaa gtgcggggct ccaatggcgc tttctacaag gcatttgtaa aggatgttca     300
tgaagattca ataacagttg catttgaaaa caactggcag cctgataggc agattccatt     360
tcatgatgtc agattcccac ctcctgtagg ttataataaa gatataaatg aaagtgatga     420
agttgaggtg tattccagag caaatgaaaa agagccttgc tgttggtggt tagctaaagt     480
gaggatgata aagggtgagt tttatgtgat agaatatgca gcatgtgatg caacttacaa     540
tgaaattgtc acaattgaac gtctaagatc tgttaatccc aacaaacctg ccacaaaaga     600
tactttccat aagatcaagc tggatgtgcc agaagactta cggcaaatgt gtgccaaaga     660
ggcggcacat aaggatttta aaaaggcagt tggtgccttt tctgtaactt atgatccaga     720
aaattatcag cttgtcattt tgtccatcaa tgaagtcacc tcaaagcgag cacatatgct     780
gattgacatg cactttcgga gtctgcgcac taagttgtct ctgataatga aaatgaaga     840 agctagtaag cagctggaga gttcaaggca gcttgcctcg agatttcatg aacagtttat     900
cgtaagagaa gatctgatgg gtctagctat tggtactcat ggtgctaata ttcagcaagc     960
tagaaaagta cctgggtca ctgctattga tctagatgaa gatacctgca catttcatat    1020
ttatggagag gatcaggatg cagtgaaaaa agctagaagc tttctcgaat tgctgaaga    1080 tgtaatacaa gttccaagga acttagtagg caaagtaata ggaaaaaatg gaaagctgat    1140
tcaggagatt gtgacaagt caggagttgt gagggtgagg attgaggctg aaaatgagaa    1200
aaatgttcca caagaagagg aaattatgcc accaaattcc cttccttcca ataattcaag    1260
```

-continued

```
ggttggacct aatgccccag aagaaaaaaa acatttagat ataaaggaaa acagcaccca   1320
tttttctcaa cctaacagta caaaagtcca gagggtgtta gtggcttcat cagttgtagc   1380
aggggaatcc cagaaacctg aactcaaggc ttggcagggt atggtaccat ttgtttttgt   1440
gggaacaaag gacagcatcg ctaatgccac tgttctttg gattatcacc tgaactattt    1500
aaagctccaa cagaggaaga gagggagagc ttcctgcgca gaggagacgg acggcggcgt   1560
ggaggggag gaagaggaca aggaggaaga ggacgtggag gaggcttcaa aggaaacgac    1620
gatcactccc gaacagataa tcgtccacgt aatccaagag aggctaaagg aagaacaaca   1680
gatggatccc ttcagatcag agttgactgc aataatgaaa ggagtgtcca cactaaaaca   1740
ttacagaata cctccagtga aggtagtcgg ctgcgcacgg gtaaagatcg taaccagaag   1800
aaagagaagc cagacagcgt ggatggtcag caaccactcg tgaatggagt accctaaact   1860
gcataattct gaagttatat ttcctatacc atttccgtaa ttcttattcc atattagaaa   1920
actttgttag gccaaagaca aatagtaggc aagatggcac agggcatgaa atgaacacaa   1980
attatgctaa gaattttta tttttggta ttggccataa gcaacaattt tcagatttgc     2040
acaaaaagat accttaaaat ttgaaacatt gcttttaaaa ctacttagca cttcagggca   2100
gattttagtt ttattttcta aagtactgag cagtgatatt ctttgttaat ttggaccatt   2160
ttcctgcatt gggtgatcat tcaccagtac attctcagtt tttcttaata tatagcatt    2220
atggtaatca tattagactt ctgttttcaa tctcgtatag aagtcttcat gaaatgctat   2280
gtcatttcat gtcctgtgtc agtttatgtt tggtccact tttccagtat tttagtggac    2340
cctgaaatgt gtgtgatgtg acatttgtca ttttcattag caaaaaagt tgtatgatct    2400
gtgcctttt tatatcttgg caggtaggaa tattatattt ggatgcagag ttcagggaag    2460
ataagttgga aacactaaat gttaaagatg tagcaaaccc tgtcaaacat tagtacttta   2520
tagaagaatg catgctttcc atattttttt ccttacataa acatcaggtt aggcagtata   2580
aagaatagga cttgttttg ttttgtttt gttgcactga agtttgataa atagtgttat     2640
tgagagagat gtgtaatttt tctgtataga caggagaaga aagaactatc ttcatctgag   2700
agaggctaaa atgttttcag ctaggaacaa atcttcctgg tcgaaagtta gtaggatatg   2760
cctgctcttt ggcctgatga ccaatttta cttagagctt ttttttttta attttgtctg    2820
ccccaagttt tgtgaaattt ttcatatttt aatttcaagc ttattttgga gagataggaa   2880
ggtcatttcc atgtatgcat aataatcctg caaagtacag gtactttgtc taagaaacat   2940
tggaagcagg ttaaatgttt tgtaaacttt gaaatatatg gtctaatgtt taagcagaat   3000
tggaaaagac taagatcggt taacaaataa caactttttt ttctttttt cttttgtttt    3060
ttgaagtgtt ggggtttggt tttgttttt gagtcttttt tttttaagtg aaatttattg    3120
aggaaaaata tgtgaaggac cttcactcta agatgttata ttttcttaa aaagtaactc    3180
ctagtagggg taccactgaa tctgtacaga gccgtaaaaa ctgaagttct gcctctgatg   3240
tattttgtga gtttgtttct ttgaattttc attttacagt tactttcct tgcatacaaa    3300
caagcatata aaatggcaac aaactgcaca tgatttcaca aatattaaaa agtcttttaa   3360
aaagtattgc caaacattaa tgttgatttc tagttattta ttctgggaat gtatagtatt   3420
tgaaaacaga aattggtacc ttgcacacat catctgtaag ctgtttggtt ttaaaatact   3480
gtagataatt aaccaaggta gaatgacctt gtaatgtaac tgctcttggg caatattctc   3540
tgtacatatt agcgacaaca gattggattt tatgttgaca tttgtttggt tatagtgcaa   3600
```

| | |
|---|---:|
| tatattttgt atgcaagcag tttcaataaa gtttgatctt cctctgctaa attgatgttg | 3660 |
| atgcaatcct tacaaatgat tgcttttaaa attttaagct aggaaaagaa atctatagaa | 3720 |
| agtgttctgt tacaaaatgt aactgttacc attggaaatt tcacgtcata ggaagttagc | 3780 |
| ctttatctac caactttcaa gaacttgttt aataaagcga aaactcaac caaatggtac | 3840 |
| aaaaccacag tgtaccatta aaatatgcac taagtctctt ttttacaaag gctgtattca | 3900 |
| gcaaggcgct aacttgctta aatgtgaatt actaacttct aaaactgtac tttgattcac | 3960 |
| atgttttcaa atggagttgg agttcattca tattacaata tttgtgtgct aaacgtgtat | 4020 |
| gtttttcagt tcaaagtcat gatgttttta aaatcttatt aaagtttcaa aaatctgaag | 4080 |
| attgtttatc tagatgtaaa tttttattaa aaagttgcac ttatgaaaaa gcaaaaaatt | 4140 |

<210> SEQ ID NO 2
<211> LENGTH: 4348
<212> TYPE: DNA
<213> ORGANISM: Artificial Sequence
<220> FEATURE:
<223> OTHER INFORMATION: Synthetic nucleotide

<400> SEQUENCE: 2

| | |
|---|---:|
| acttccggtg gagggccgcc tctgagcggg cggcgggccg acggcgagcg cgggcggcgg | 60 |
| cggtgacgga ggcgccgctg ccaggggggcg tgcggcagcg cggcggcggc ggcggcggcg | 120 |
| gcggcggcgc aggcggcggc ggcggcggcg gcggcggcg ctgggcctcg agcgcccgca | 180 |
| gcccacctct cggggggcggg ctccggggcgc tagcagggct gaagagaaga tggaggagct | 240 |
| ggtggtggaa gtgcggggct ccaatggcgc tttctacaag gcatttgtaa aggatgttca | 300 |
| tgaagattca ataacagttg catttgaaaa caactggcag cctgataggc agattccatt | 360 |
| tcatgatgtc agattcccac ctcctgtagg ttataataaa gatataaatg aaagtgatga | 420 |
| agttgaggtg tattccagag caaatgaaaa agagccttgc tgttggtggt tagctaaagt | 480 |
| gaggatgata aagggtgagt tttatgtgat agaaatgca gcatgtgatg caacttacaa | 540 |
| tgaaattgtc acaattgaac gtctaagatc tgttaatccc aacaaacctg ccacaaaaga | 600 |
| tactttccat aagatcaagc tggatgtgcc agaagactta cggcaaatgt gtgccaaaga | 660 |
| ggcggcacat aaggatttta aaaaggcagt tggtgccttt tctgtaactt atgatccaga | 720 |
| aaattatcag cttgtcattt tgtccatcaa tgaagtcacc tcaaagcgag cacatatgct | 780 |
| gattgacatg cactttcgga gtctgcgcac taagttgtct ctgataatga aaatgaaga | 840 |
| agctagtaag cagctggaga gttcaaggca gcttgcctcg agatttcatg aacagtttat | 900 |
| cgtaagagaa gatctgatgg gtctagctat tggtactcat ggtgctaata ttcagcaagc | 960 |
| tagaaaagta cctggggtca ctgctattga tctagatgaa gatacctgca catttcatat | 1020 |
| ttatggagag gatcaggatg cagtgaaaaa agctagaagc tttctcgaat tgctgaaga | 1080 |
| tgtaatacaa gttccaagga acttagtagg caaagtaata ggaaaaaatg aaagctgat | 1140 |
| tcaggagatt gtggacaagt caggagttgt gagggtgagg attgaggctg aaatgaga | 1200 |
| aaatgttcca caagaagagg aaattatgcc accaaattcc cttccttcca ataattcaag | 1260 |
| ggttggacct aatgccccag aagaaaaaaa acatttagat ataaaggaaa acagcaccca | 1320 |
| ttttctcaa cctaacagta caaaagtcca gaggggtatg gtaccatttg ttttgtggg | 1380 |
| aacaaaggac agcatcgcta atgccactgt tcttttggat tatcacctga actatttaaa | 1440 |
| ggaagtagac cagttgcgtt tggagagatt acaaattgat gagcagttgc gacagattgg | 1500 |
| agctagttct agaccaccac caaatcgtac agataaggaa aaaagctatg tgactgatga | 1560 |

-continued

```
tggtcaagga atgggtcgag gtagtagacc ttacagaaat aggggggcacg gcagacgcgg      1620 tcctggatat acttcaggaa ctaattctga agcatcaaat gcttctgaaa cagaatctga      1680
ccacagagac gaactcagtg attggtcatt agctccaaca gaggaagaga gggagagctt      1740
cctgcgcaga ggagacggac ggcggcgtgg aggggggagga agaggacaag gaggaagagg      1800
acgtggagga ggcttcaaag gaaacgacga tcactcccga acagataatc gtccacgtaa      1860
tccaagagag gctaaggaa gaacaacaga tggatccctt cagatcagag ttgactgcaa       1920
taatgaaagg agtgtccaca ctaaaacatt acagaatacc tccagtgaag gtagtcggct      1980
gcgcacgggt aaagatcgta accagaagaa agagaagcca gacagcgtgg atggtcagca      2040
accactcgtg aatggagtac cctaaactgc ataattctga agttatattt cctataccat      2100
ttccgtaatt cttattccat attagaaaac tttgttaggc caaagacaaa tagtaggcaa      2160
gatggcacag ggcatgaaat gaacacaaat tatgctaaga attttttatt ttttggtatt      2220
ggccataagc aacaatttc agatttgcac aaaaagatac cttaaaattt gaaacattgc       2280
ttttaaaact acttagcact tcagggcaga ttttagtttt attttctaaa gtactgagca      2340
gtgatattct ttgttaattt ggaccatttt cctgcattgg gtgatcattc accagtacat      2400
tctcagtttt tcttaatata tagcatttat ggtaatcata ttagacttct gttttcaatc      2460
tcgtatagaa gtcttcatga aatgctatgt catttcatgt cctgtgtcag tttatgtttt      2520
ggtccacttt tccagtattt tagtggaccc tgaaatgtgt gtgatgtgac atttgtcatt      2580
ttcattagca aaaaagttg tatgatctgt gccttttta tatcttggca ggtaggaata       2640
ttatatttgg atgcagagtt cagggaagat aagttggaaa cactaaatgt taaagatgta     2700
gcaaaccctg tcaaacatta gtactttata gaagaatgca tgctttccat atttttttcc     2760
ttacataaac atcaggttag gcagtataaa gaataggact tgttttttgt tttgttttgt    2820
tgcactgaag tttgataaat agtgttattg agagagatgt gtaattttc tgtatagaca     2880 ggagaagaaa gaactatctt catctgagag aggctaaaat gttttcagct aggaacaaat    2940
cttcctggtc gaaagttagt aggatatgcc tgctctttgg cctgatgacc aattttaact    3000
tagagctttt tttttttaat tttgtctgcc ccaagttttg tgaaattttt catattttaa    3060
tttcaagctt attttggaga gataggaagg tcatttccat gtatgcataa taatcctgca    3120
aagtacaggt acttttgtcta agaaacattg gaagcaggtt aaatgttttg taaacttga    3180 aatatatggt ctaatgttta agcagaattg gaaaagacta agatcggtta acaaataaca    3240 acttttttt cttttttct tttgttttt gaagtgttgg ggtttggttt tgttttttga     3300 gtctttttt tttaagtgaa atttattgag gaaaaatatg tgaaggacct tcactctaag    3360
atgttatatt tttcttaaaa agtaactcct agtaggggta ccactgaatc tgtacagagc    3420
cgtaaaaact gaagttctgc ctctgatgta ttttgtgagt ttgtttcttt gaattttcat    3480
tttacagtta cttttccttg catacaaaca agcatataaa atggcaacaa actgcacatg    3540
atttcacaaa tattaaaaag tcttttaaaa agtattgcca acattaatg ttgatttcta    3600 gttatttatt ctgggaatgt atagtatttg aaaacagaaa ttggtacctt gcacacatca    3660
tctgtaagct gtttggtttt aaaatactgt agataattaa ccaaggtaga atgaccttgt    3720
aatgtaactg ctcttgggca atattctctg tacatattag cgacaacaga ttggatttta    3780
tgttgacatt tgtttggtta tagtgcaata tattttgtat gcaagcagtt tcaataaagt    3840
ttgatcttcc tctgctaaat tgatgttgat gcaatcctta caaatgattg cttttaaaat    3900
```

| | |
|---|---|
| tttaagctag gaaaagaaat ctatagaaag tgttctgtta caaaatgtaa ctgttaccat | 3960 |
| tggaaatttc acgtcatagg aagttagcct ttatctacca actttcaaga acttgtttaa | 4020 |
| taaagcgaaa aactcaacca aatggtacaa aaccacagtg taccattaaa atatgcacta | 4080 |
| agtctctttt ttacaaaggc tgtattcagc aaggcgctaa cttgcttaaa tgtgaattac | 4140 |
| taacttctaa aactgtactt tgattcacat gttttcaaat ggagttggag ttcattcata | 4200 |
| ttacaatatt tgtgtgctaa acgtgtatgt ttttcagttc aaagtcatga tgtttttaaa | 4260 |
| atcttattaa agtttcaaaa atctgaagat tgtttatcta gatgtaaatt tttattaaaa | 4320 |
| agttgcactt atgaaaaagc aaaaaatt | 4348 |

<210> SEQ ID NO 3
<211> LENGTH: 4107
<212> TYPE: DNA
<213> ORGANISM: Artificial Sequence
<220> FEATURE:
<223> OTHER INFORMATION: Synthetic nucleotide

<400> SEQUENCE: 3

| | |
|---|---|
| ctcagtcagg cgctcagctc cgtttcggtt tcacttccgg tggagggccg cctctgagcg | 60 |
| ggcggcgggc cgacggcgag cgcgggcggc ggcggtgacg gaggcgccgc tgccaggggg | 120 |
| cgtgcggcag cgcggcggcg gcggcggcgg cggcggcggc ggaggcggcg gcggcggcgg | 180 |
| cggcggcggc ggctgggcct cgagcgcccg cagcccacct ctcggggggcg ggctcccggc | 240 |
| gctagcaggg ctgaagagaa gatggaggag ctggtggtgg aagtgcgggg ctccaatggc | 300 |
| gctttctaca aggcatttgt aaaggatgtt catgaagatt caataacagt tgcatttgaa | 360 |
| aacaactggc agcctgatag gcagattcca tttcatgatg tcagattccc acctcctgta | 420 |
| ggttataata agatataaa tgaaagtgat gaagttgagg tgtattccag agcaaatgaa | 480 |
| aaagagcctt gctgttggtg gttagctaaa gtgaggatga taaagggtga gttttatgtg | 540 |
| atagaatatg cagcatgtga tgcaacttac aatgaaattg tcacaattga acgtctaaga | 600 |
| tctgttaatc ccaacaaacc tgccacaaaa gatactttcc ataagatcaa gctggatgtg | 660 |
| ccagaagact acggcaaat gtgtgccaaa gaggcggcac ataaggattt taaaaaggca | 720 |
| gttggtgcct tttctgtaac ttatgatcca gaaaattatc agcttgtcat tttgtccatc | 780 |
| aatgaagtca cctcaaagcg agcacatatg ctgattgaca tgcactttcg gagtctgcgc | 840 |
| actaagttgt ctctgataat gagaaatgaa gaagctagta agcagctgga gagttcaagg | 900 |
| cagcttgcct cgagatttca tgaacagttt atcgtaagag aagatctgat gggtctagct | 960 |
| attggtactc atggtgctaa tattcagcaa gctagaaaag tacctggggt cactgctatt | 1020 |
| gatctagatg aagatacctg cacatttcat atttatggag aggatcagga tgcagtgaaa | 1080 |
| aaagctagaa gctttctcga atttgctgaa gatgtaatac aagttccaag gaacttagta | 1140 |
| ggcaaagtaa taggaaaaaa tggaaagctg attcaggaga ttgtggacaa gtcaggagtt | 1200 |
| gtgagggtga ggattgaggc tgaaaatgag aaaaatgttc acaagaaga ggaaattatg | 1260 |
| ccaccaaatt cccttccttc caataattca agggttggac ctaatgcccc agaagaaaaa | 1320 |
| aaacatttag atataaagga aaacagcacc catttttctc aacctaacag tacaaaagtc | 1380 |
| cagagggta tggtaccatt tgttttgtg gaacaaagg acagcatcgc taatgccact | 1440 |
| gttcttttgg attatcacct gaactattta aagctccaac agaggaagag agggagagct | 1500 |
| tcctgcgcag aggagacgga cggcggcgtg gaggggagg aagaggacaa ggaggaagag | 1560 |
| gacgtggagg aggcttcaaa ggaaacgacg atcactcccg aacagataat cgtccacgta | 1620 |

```
atccaagaga ggctaaagga agaacaacag atggatccct tcagatcaga gttgactgca   1680
ataatgaaag gagtgtccac actaaaacat tacagaatac ctccagtgaa ggtagtcggc   1740
tgcgcacggg taaagatcgt aaccagaaga aagagaagcc agacagcgtg gatggtcagc   1800
aaccactcgt gaatggagta ccctaaactg cataattctg aagttatatt tcctatacca   1860
tttccgtaat tcttattcca tattagaaaa ctttgttagg ccaaagacaa atagtaggca   1920
agatggcaca gggcatgaaa tgaacacaaa ttatgctaag aattttttat ttttggtat    1980 tggccataag caacaatttt cagatttgca caaaagata ccttaaaatt tgaaacattg    2040 ctttaaaac tacttagcac ttcagggcag attttagttt tatttctaa agtactgagc     2100 agtgatattc tttgttaatt tggaccattt cctgcattg ggtgatcatt caccagtaca    2160
ttctcagttt ttcttaatat atagcattta tggtaatcat attagacttc tgttttcaat   2220
ctcgtataga agtcttcatg aaatgctatg tcatttcatg tcctgtgtca gtttatgttt   2280
tggtccactt ttccagtatt ttagtggacc ctgaaatgtg tgtgatgtga catttgtcat   2340
tttcattagc aaaaaagtt gtatgatctg tgcctttttt atatcttggc aggtaggaat    2400
attatatttg gatgcagagt tcagggaaga taagttggaa acactaaatg ttaaagatgt    2460
agcaaaccct gtcaaacatt agtactttat agaagaatgc atgctttcca tattttttc    2520 cttacataaa catcaggtta ggcagtataa agaataggac ttgttttgt tttgttttg     2580 ttgcactgaa gtttgataaa tagtgttatt gagagagatg tgtaattttt ctgtatagac   2640
aggagaagaa agaactatct tcatctgaga gaggctaaaa tgttttcagc taggaacaaa   2700
tcttcctggt cgaaagttag taggatatgc ctgctctttg gcctgatgac caatttttaac  2760 ttagagcttt ttttttttaa ttttgtctgc cccaagtttt gtgaaattt tcatatttta    2820 atttcaagct tattttggag agataggaag gtcatttcca tgtatgcata ataatcctgc   2880
aaagtacagg tactttgtct aagaaacatt ggaagcaggt taaatgtttt gtaaactttg   2940
aaatatatgg tctaatgttt aagcagaatt ggaaaagact aagatcggtt aacaaataac   3000 aactttttt tctttttttc ttttgttttt tgaagtgttg gggttggtt ttgttttttg     3060 agtctttttt ttttaagtga aatttattga ggaaaaatat gtgaaggacc ttcactctaa   3120
gatgttatat ttttcttaaa aagtaactcc tagtaggggt accactgaat ctgtacagag    3180
ccgtaaaaac tgaagttctg cctctgatgt atttgtgag tttgtttctt tgaattttca    3240
ttttacagtt acttttcctt gcatacaaac aagcatataa aatggcaaca aactgcacat   3300
gatttcacaa atattaaaaa gtcttttaaa agtattgcc aaacattaat gttgatttct    3360
agttatttat tctgggaatg tatagtattt gaaaacagaa attggtacct tgcacacatc   3420
atctgtaagc tgtttggttt taaaatactg tagataatta accaaggtag aatgaccttg   3480
taatgtaact gctcttgggc aatattctct gtacatatta gcgacaacag attggatttt   3540
atgttgacat ttgtttggtt atagtgcaat atatttgta tgcaagcagt ttcaataaag    3600
tttgatcttc ctctgctaaa ttgatgttga tgcaatcctt acaaatgatt gcttttaaaa   3660
ttttaagcta ggaaaagaaa tctatagaaa gtgttctgtt acaaaatgta actgttacca   3720
ttggaaattt cacgtcatag gaagttagcc tttatctacc aactttcaag aacttgttta   3780
ataaagcgaa aaactcaacc aaatggtaca aaaccacagt gtaccattaa aatatgcact   3840
aagtctcttt tttacaaagg ctgtattcag caaggcgcta acttgcttaa atgtgaatta   3900
ctaacttcta aaactgtact ttgattcaca tgttttcaaa tggagttgga gttcattcat   3960
```

| attacaatat ttgtgtgcta aacgtgtatg tttttcagtt caaagtcatg atgttttaa | 4020 |
| aatcttatta aagtttcaaa aatctgaaga ttgtttatct agatgtaaat ttttattaaa | 4080 |
| aagttgcact tatgaaaaag caaaaaa | 4107 |

<210> SEQ ID NO 4
<211> LENGTH: 4303
<212> TYPE: DNA
<213> ORGANISM: Artificial Sequence
<220> FEATURE:
<223> OTHER INFORMATION: Synthetic nucleotide

<400> SEQUENCE: 4

| ctcagtcagg cgctcagctc cgtttcggtt tcacttccgg tggagggccg cctctgagcg | 60 |
| ggcggcgggc cgacggcgag cgcgggcggc ggcggtgacg gaggcgccgc tgccaggggg | 120 |
| cgtgcggcag cgcggcggcg gcggcggcgg cggcggcggc ggaggcggcg gcggcggcgg | 180 |
| cggcggcggc ggctgggcct cgagcgcccg cagcccacct ctcggggggcg ggctcccggc | 240 |
| gctagcaggg ctgaagagaa gatggaggag ctggtggtgg aagtgcgggg ctccaatggc | 300 |
| gctttctaca aggcatttgt aaaggatgtt catgaagatt caataacagt tgcatttgaa | 360 |
| aacaactggc agcctgatag gcagattcca tttcatgatg tcagattccc acctcctgta | 420 |
| ggttataata agatataaa tgaaagtgat gaagttgagg tgtattccag agcaaatgaa | 480 |
| aaagagcctt gctgttggtg gttagctaaa gtgaggatga taagggtga gttttatgtg | 540 |
| atagaatatg cagcatgtga tgcaacttac aatgaaattg tcacaattga acgtctaaga | 600 |
| tctgttaatc ccaacaaacc tgccacaaaa gatactttcc ataagatcaa gctggatgtg | 660 |
| ccagaagact acggcaaat gtgtgccaaa gaggcggcac ataaggattt taaaaaggca | 720 |
| gttggtgcct tttctgtaac ttatgatcca gaaaattatc agcttgtcat tttgtccatc | 780 |
| aatgaagtca cctcaaagcg agcacatatg ctgattacaa tgcactttcg gagtctgcgc | 840 |
| actaagttgt ctctgataat gagaaatgaa gaagctagta agcagctgga gagttcaagg | 900 |
| cagcttgcct cgagatttca tgaacagttt atcgtaagag aagatctgat gggtctagct | 960 |
| attggtactc atggtgctaa tattcagcaa gctagaaaag tacctgggt cactgctatt | 1020 |
| gatctagatg aagatacctg cacatttcat atttatggag aggatcagga tgcagtgaaa | 1080 |
| aaagctagaa gctttctcga atttgctgaa gatgtaatac aagttccaag gaacttagta | 1140 |
| ggcaaagtaa taggaaaaaa tggaaagctg attcaggaga ttgtggacaa gtcaggagtt | 1200 |
| gtgagggtga ggattgaggc tgaaaatgag aaaaatgttc acaagaaga ggaaattatg | 1260 |
| ccaccaaatt cccttccttc caataattca agggttggac ctaatgcccc agaagaaaaa | 1320 |
| aaacatttag atataaagga aaacagcacc catttttctc aacctaacag tacaaaagtc | 1380 |
| cagagggggta tggtaccatt tgttttttgtg ggaacaaagg acagcatcgc taatgccact | 1440 |
| gttcttttgg attatcacct gaactattta aggaagtag accagttgcg tttggagaga | 1500 |
| ttacaaattg atgagcagtt gcgacagatt ggagctagtt ctagaccacc accaaatcgt | 1560 |
| acagataagg aaaaaagcta tgtgactgat gatggtcaag aatgggtcg aggtagtaga | 1620 |
| ccttacagaa ataggggca cggcagacgc ggtcctggat atacttcagc tccaacagag | 1680 |
| gaagagaggg agagcttcct gcgcagagga gacggacggc ggcgtggagg gggaggaaga | 1740 |
| ggacaaggag gaagaggacg tggaggaggc ttcaaaggaa acgacgatca ctcccgaaca | 1800 |
| gataatcgtc cacgtaatcc aagagaggct aaaggaagaa caacagatgg atcccttcag | 1860 |
| atcagagttg actgcaataa tgaaaggagt gtccacacta aaacattaca gaatacctcc | 1920 |

```
agtgaaggta gtcggctgcg cacgggtaaa gatcgtaacc agaagaaaga gaagccagac    1980
agcgtggatg gtcagcaacc actcgtgaat ggagtaccct aaactgcata attctgaagt    2040
tatatttcct ataccatttc cgtaattctt attccatatt agaaactttt gttaggccaa    2100
agacaaatag taggcaagat ggcacagggc atgaaatgaa cacaaattat gctaagaatt    2160
ttttattttt tggtattggc cataagcaac aattttcaga tttgcacaaa aagataccct    2220
aaaatttgaa acattgcttt taaaactact tagcacttca gggcagattt tagttttatt    2280
ttctaaagta ctgagcagtg atattctttg ttaatttgga ccattttcct gcattgggtg    2340
atcattcacc agtacattct cagttttttct taatatatag catttatggt aatcatatta    2400
gacttctgtt ttcaatctcg tatagaagtc ttcatgaaat gctatgtcat ttcatgtcct    2460
gtgtcagttt atgttttggt ccacttttcc agtattttag tggaccctga atgtgtgtg    2520 atgtgacatt tgtcatttc attagcaaaa aaagttgtat gatctgtgcc ttttttatat    2580
cttggcaggt aggaatatta tatttggatg cagagttcag ggaagataag ttggaaacac    2640
taaatgttaa agatgtagca aaccctgtca acattagta ctttatagaa gaatgcatgc    2700
tttccatatt ttttttcctta cataaacatc aggttaggca gtataaagaa taggacttgt    2760
ttttgttttt gttttgttgc actgaagttt gataaatagt gttattgaga gagatgtgta    2820 attttttctgt atagacagga gaagaaagaa ctatcttcat ctgagagagg ctaaaatgtt    2880
ttcagctagg aacaaatctt cctggtcgaa agttagtagg atatgcctgc tctttggcct    2940
gatgaccaat tttaacttag agcttttttt ttttaatttt gtctgcccca agttttgtga    3000 aattttcat attttaattt caagcttatt ttggagagat aggaaggtca tttccatgta    3060
tgcataataa tcctgcaaag tacaggtact tgtctaaga acattggaa gcaggttaaa    3120 tgttttgtaa actttgaaat atatggtcta atgtttaagc agaattggaa aagactaaga    3180
tcggttaaca ataacaact ttttttttctt ttttttcttt gttttttgaa gtgttggggt    3240
ttggttttgt ttttttgagtc tttttttttt aagtgaaatt tattgaggaa aaatatgtga    3300
aggaccttca ctctaagatg ttatattttt cttaaaagt aactcctagt aggggtacca    3360
ctgaatctgt acagagccgt aaaaactgaa gttctgcctc tgatgtattt tgtgagtttg    3420
tttctttgaa ttttcatttt acagttactt ttccttgcat acaaacaagc atataaaatg    3480
gcaacaaact gcacatgatt tcacaaatat taaaaagtct tttaaaaagt attgccaaac    3540
attaatgttg atttctagtt atttattctg ggaatgtata gtatttgaaa acagaaattg    3600
gtaccttgca cacatcatct gtaagctgtt tggttttaaa atactgtaga taattaacca    3660
aggtagaatg accttgtaat gtaactgctc ttgggcaata ttctctgtac atattagcga    3720
caacagattg gattttatgt tgacatttgt ttggtattag tgcaatatat tttgtatgca    3780
agcagtttca ataaagtttg atcttcctct gctaaattga tgttgatgca atccttacaa    3840
atgattgctt ttaaaatttt aagctaggaa aagaaatcta tagaaagtgt tctgttacaa    3900
aatgtaactg ttaccattgg aaatttcacg tcataggaag ttagccttta tctaccaact    3960
ttcaagaact tgtttaataa agcgaaaaac tcaaccaaat ggtacaaaac cacagtgtac    4020
cattaaaata tgcactaagt ctctttttta caaaggctgt attcagcaag gcgctaactt    4080
gcttaaatgt gaattactaa cttctaaaac tgtactttga ttcacatgtt ttcaaatgga    4140
gttggagttc attcatatta caatatttgt gtgctaaacg tgtatgtttt tcagttcaaa    4200
gtcatgatgt ttttaaaatc ttattaaagt ttcaaaaatc tgaagattgt ttatctagat    4260
```

```
gtaaattttt attaaaaagt tgcacttatg aaaaagcaaa aaa            4303
```

<210> SEQ ID NO 5
<211> LENGTH: 4441
<212> TYPE: DNA
<213> ORGANISM: Artificial Sequence
<220> FEATURE:
<223> OTHER INFORMATION: Synthetic nucleotide

<400> SEQUENCE: 5

```
ctcagtcagg cgctcagctc cgtttcggtt tcacttccgg tggagggccg cctctgagcg     60
ggcggcgggc cgacggcgag cgcgggcggc ggcggtgacg gaggcgccgc tgccaggggg    120
cgtgcggcag cgcggcggcg gcggcggcgg cggcggcggc ggaggcggcg gcggcggcgg    180
cggcggcggc ggctgggcct cgagcgcccg cagcccacct ctcggggggcg ggctcccggc    240
gctagcaggg ctgaagagaa gatggaggag ctggtggtgg aagtgcgggg ctccaatggc    300
gctttctaca aggcatttgt aaaggatgtt catgaagatt caataacagt tgcatttgaa    360
aacaactggc agcctgatag gcagattcca tttcatgatg tcagattccc acctcctgta    420
ggttataata agatataaa tgaaagtgat gaagttgagg tgtattccag agcaaatgaa    480
aaagagcctt gctgttggtg gttagctaaa gtgaggatga taaagggtga gttttatgtg    540
atagaatatg cagcatgtga tgcaacttac aatgaaattg tcacaattga acgtctaaga    600
tctgttaatc ccaacaaacc tgccacaaaa gatactttcc ataagatcaa gctggatgtg    660
ccagaagact acggcaaat gtgtgccaaa gaggcggcac ataaggattt taaaaaggca    720
gttggtgcct tttctgtaac ttatgatcca gaaaattatc agcttgtcat tttgtccatc    780
aatgaagtca cctcaaagcg agcacatatg ctgattgaca tgcactttcg gagtctgcgc    840
actaagttgt ctctgataat gagaaatgaa gaagctagta agcagctgga gagtcaagg    900
cagcttgcct cgagatttca tgaacagttt atcgtaagag aagatctgat gggtctagct    960
attggtactc atggtgctaa tattcagcaa gctagaaag tacctggggt cactgctatt   1020
gatctagatg aagatacctg cacatttcat atttatggag aggatcagga tgcagtgaaa   1080
aaagctagaa gctttctcga atttgctgaa gatgtaatac aagttccaag gaacttagta   1140
ggcaaagtaa taggaaaaaa tggaaagctg attcaggaga ttgtggacaa gtcaggagtt   1200
gtgagggtga ggattgaggc tgaaaatgag aaaaatgttc acaagaaga ggaaattatg   1260
ccaccaaatt cccttccttc caataattca agggttggac ctaatgcccc agaagaaaa    1320
aaacatttag atataaagga aaacagcacc cattttttctc aacctaacag tacaaaagtc   1380
cagagggtgt tagtggcttc atcagttgta gcaggggaat cccagaaacc tgaactcaag   1440
gcttggcagg gtatggtacc atttgttttt gtgggaacaa aggacagcat cgctaatgcc   1500
actgttcttt tggattatca cctgaactat ttaaaggaag tagaccagtt gcgtttggag   1560
agattacaaa ttgatgagca gttgcgacag attggagcta gttctagacc accaccaaat   1620
cgtacagata aggaaaaaag ctatgtgact gatgatggtc aaggaatggg tcgaggtagt   1680
agaccttaca gaaatagggg gcacggcaga cgcggtcctg gatatacttc aggaactaat    1740
tctgaagcat caaatgcttc tgaaacagaa tctgaccaca gagacgaact cagtgattgg   1800
tcattagctc aacagagga agagagggag agcttcctgc gcagaggaga cggacggcgg   1860
cgtggagggg gaggaagagg acaaggagga agaggacgtg gaggaggctt caaaggaaac   1920
gacgatcact cccgaacaga taatcgtcca cgtaatccaa gagaggctaa aggaagaaca   1980
acagatggat cccttcagat cagagttgac tgcaataatg aaaggagtgt ccacactaaa   2040
```

-continued

```
acattacaga ataccoccag tgaaggtagt cggctgcgca cgggtaaaga tcgtaaccag    2100
aagaaagaga agccagacag cgtggatggt cagcaaccac tcgtgaatgg agtaccctaa    2160
actgcataat tctgaagtta tatttcctat accatttccg taattcttat tccatattag    2220
aaaactttgt taggccaaag acaaatagta ggcaagatgg cacagggcat gaaatgaaca    2280 caattatgc taagaatttt ttattttttg gtattggcca taagcaacaa ttttcagatt     2340
tgcacaaaaa gataccttaa aatttgaaac attgcttta aaactactta gcacttcagg     2400
gcagatttta gttttatttt ctaaagtact gagcagtgat attctttgtt aatttggacc    2460
attttcctgc attgggtgat cattcaccag tacattctca gttttcctta atatatagca    2520
tttatggtaa tcatattaga cttctgtttt caatctcgta tagaagtctt catgaaatgc    2580
tatgtcattt catgtcctgt gtcagtttat gttttggtcc acttttccag tattttagtg    2640
gaccctgaaa tgtgtgtgat gtgacatttg tcattttcat tagcaaaaaa agttgtatga    2700
tctgtgcctt tttatatcct tggcaggtag gaatattata tttggatgca gagttcaggg    2760
aagataagtt ggaaacacta atgttaaag atgtagcaaa ccctgtcaaa cattagtact      2820
ttatagaaga atgcatgctt tccatatttt tttccttaca taaacatcag gttaggcagt    2880
ataaagaata ggacttgttt ttgttttgt tttgttgcac tgaagtttga taaatagtgt      2940
tattgagaga gatgtgtaat ttttctgtat agacaggaga agaaagaact atcttcatct    3000
gagagaggct aaaatgtttt cagctaggaa caaatcttcc tggtcgaaag ttagtaggat    3060
atgcctgctc tttggcctga tgaccaattt taacttagag cttttttttt ttaattttgt    3120
ctgccccaag ttttgtgaaa ttttttcatat tttaatttca agcttatttt ggagagatag   3180
gaaggtcatt tccatgtatg cataataatc ctgcaaagta caggtacttt gtctaagaaa    3240
cattggaagc aggttaaatg ttttgtaaac tttgaaatat atggtctaat gtttaagcag    3300
aattggaaaa gactaagatc ggttaacaaa taacaacttt tttttcttt tttcttttgt      3360 tttttgaagt gttggggttt ggttttgttt tttgagtctt ttttttttaa gtgaaattta    3420
ttgaggaaaa atatgtgaag gaccttcact ctaagatgtt atattttct taaaagtaa      3480 ctcctagtag gggtaccact gaatctgtac agagccgtaa aaactgaagt tctgcctctg    3540
atgtattttg tgagtttgtt tctttgaatt tcatttttac agttactttt ccttgcatac    3600
aaacaagcat ataaaatggc aacaaactgc acatgatttc acaaatatta aaagtctttt   3660 taaaagtat tgccaaacat taatgttgat ttctagttat ttattctggg aatgtatagt     3720
atttgaaaac agaaattggt accttgcaca catcatctgt aagctgtttg gttttaaaat    3780
actgtagata attaaccaag gtagaatgac cttgtaatgt aactgctctt gggcaatatt    3840
ctctgtacat attagcgaca acagattgga ttttatgttg acatttgttt ggttatagtg    3900
caatatattt tgtatgcaag cagtttcaat aaagtttgat cttcctctgc taaattgatg    3960
ttgatgcaat ccttacaaat gattgctttt aaaatttta gctaggaaaa gaaatctata    4020
gaaagtgttc tgttacaaaa tgtaactgtt accattggaa atttcacgtc ataggaagtt    4080
agcctttatc taccaactt caagaacttg tttaataaag cgaaaaactc aaccaaatgg     4140
tacaaaacca cagtgtacca ttaaaatatg cactaagtct cttttttaca aaggctgtat    4200
tcagcaaggc gctaacttgc ttaaatgtga attactaact tctaaaactg tactttgatt    4260
cacatgtttt caaatggagt tggagttcat tcatattaca atatttgtgt gctaaacgtg    4320 tatgttttc agttcaaagt catgatgttt ttaaaatctt attaaagttt caaaaatctg      4380
```

-continued

| | |
|---|---|
| aagattgttt atctagatgt aaattttat taaaaagttg cacttatgaa aaagcaaaaa | 4440 |
| a | 4441 |

<210> SEQ ID NO 6
<211> LENGTH: 4351
<212> TYPE: DNA
<213> ORGANISM: Artificial Sequence
<220> FEATURE:
<223> OTHER INFORMATION: Synthetic nucleotide

<400> SEQUENCE: 6

| | |
|---|---|
| gtttgactgt ttacaggagg cgcagcggag cccttggcct cagtcagtca ggcgctgggg | 60 |
| agcgtttcgg tttcacttcc ggtgaggggc cgcgcctgag agggcgggca gtgaagcaaa | 120 |
| cggacggcga gcgcgggcgg tggcagtgac ggcggcgccg ctgccggggg gcgtgcggta | 180 |
| acgcggcggc ggcggcggcg gcgacggcgg ctgggcctca agcgcctgca gcccacctcc | 240 |
| cggaggcggg ctcccggcgc gaggacggac gagaagatgg aggagctggt ggtggaagtg | 300 |
| cggggctcca atggcgcttt ctacaaggca tttgtaaaag atgtccatga agattctata | 360 |
| acagttgctt tgaaaacaa ctggcaacca gagagacaga ttccattcca tgatgtgaga | 420 |
| ttcccaccac ctgtaggtta aataaagat ataaacgaaa gtgatgaagt tgaggtttat | 480 |
| tccagagcaa atgaaaaaga gccttgctgt tggtggttag ctaaagtgag gatgataaag | 540 |
| ggtgagtttt atgtgataga atatgcagca tgtgatgcta cgtataatga aattgtcaca | 600 |
| attgagcgtc tacgatctgt taatcccaac aaacctgcta caaaagatac tttccataag | 660 |
| atcaagctgg aggtgccaga agatttacga caaatgtgtg ccaaagaatc agcacataag | 720 |
| gatttaaaa aggcagttgg tgccttctct gtaacttatg atccagaaaa ttatcagctg | 780 |
| gtaattttgt ccatcaatga agtcacctca aagcgagccc acatgttgat tgacatgcac | 840 |
| tttcgaagtc tgcgcaccaa gttgtctctt atactgagaa atgaagaagc cagtaaacaa | 900 |
| ctggagagtt caaggcagct tgcctcaaga tttcatgaac agtttatcgt acgaagagat | 960 |
| ctgatgggtt tagctattgg tactcatggt gctaatattc agcaagctag aaaagtgcct | 1020 |
| ggcgtcactg ctattgattt agatgaggat acctgcacat tcatattta tggagaggat | 1080 |
| caagatgcag tgaaaaaggc tagaagcttt ctggaatttg ctgaagatgt catacaggtt | 1140 |
| ccacgaaact agtaggcaa agtaatagga aaaatggaa agctgattca agagatcgtg | 1200 |
| gacaagtcag gagttgtgag ggtgaggatt gaggctgaaa atgagaaaag tgtcccacaa | 1260 |
| gaagaggaaa ttatgccacc aagttcccta ccttccaata attcaagggt tggacctaac | 1320 |
| tcctctgaag aaaagaaaca tttagataca aaggaaaaca cccattttc tcaacctaac | 1380 |
| agtacaaaag tccagagggt gttagtggtt tcatcaattg tagcagggg accccagaaa | 1440 |
| cctgaaccca aggcttggca gggtatggta ccatttgttt ttgtgggaac aaaagacagc | 1500 |
| atcgctaatg ccactgttct tttgattat cacctgaact attaaagga agtagaccag | 1560 |
| ttgcgtttgg agagattaca aattgatgag cagttgcgac aaattggagc tagttctaga | 1620 |
| ccaccaccaa atcgtacaga taaggaaaaa ggctatgtga ctgatgatgg tcaaggaatg | 1680 |
| ggtcgaggta gtagacctta cagaaatagg gggcacggca gacgcggtcc tggatatact | 1740 |
| tcagctccaa cagaggaaga gagggagagc ttcctgcgca gaggagacgg acggcggcgt | 1800 |
| ggaggaggag gaagaggaca aggaggaaga ggaagaggag gagcttcaa aggaaacgac | 1860 |
| gatcattccc gaacagataa tcgtccacgt aatccaagag aggctaaagg aagaacagct | 1920 |
| gatggatccc tgcagagtgc ctccagtgaa gggagccggc tgcgcacggg taaagatcgt | 1980 |

```
aaccagaaga aggaaaagcc agacagcgta gatgggctgc aaccgctggt gaatggagta    2040
ccctaaataa gctacataat tccgaagtta tatttcctct accatttccg taattcttac    2100
tccattttag aaaactttgt taggccaaag acaaatagta ggcaagatgg cacagggcat    2160
gaagtgaaca caaattctgc aaagaatttt tttgatattg gcaataatca acaatcttcc    2220
agatttgcac aaaaagatct tgaaatttga tgcataactt ttaagtacac ttaacacttc    2280
agggcaggat tttacttta tttttttaaaa atactaagca gtgatcttta ttaactagga    2340
ccattttcct gaattggact atataactca gcagtatgtt tcagtctttc ggagtaaatc    2400
acatttgtga taatcatact agatctctgt cttcagtctc atttaaagtc ttcatgaaat    2460
gctgtgccat ttcatgtcct gtgtcagttt atgttttggt ccactttttcc agtattttag    2520 tggaccctga atgtgtgtg atgtgacatt tgttattttc attagcaaaa aaaagagttg    2580
tatgatctgt gccttttta tatcttggca ggtaggaata ttatatttgg atgcagagtt    2640
cagggaagat aagttggaaa cactaaatgt taaagatgta gcaaaccctg tcaaacatta    2700
gtacttttta aagaatgca tgctttccat atttttttcc ttacataaac atcagcttag    2760
gcagtataaa aaataggact tgtttttttgt ttttgttttg ttgcactgaa gtatgacaaa    2820
tagtgttatt ggaagggatg tgtaattttt ctgtatagac aggagaagaa ataactatct    2880
tttcatttgg gagaggctaa agatgttttc agctacttgc aaatcttcct ggtcgaaagt    2940
tagtaggata tgcctgctct ttggcctgat gacgaatttc aactttgaaa cattttcttt    3000
tgtcctcccc aaattttgtc aagttttttc attcatattt tacattaaag cttatttggg    3060
ggagatatga aggtcatctt cataaataca taacaaccct caaaagtata taggtacttt    3120
gtctgagaaa cattgaaagc aggttaaatg ttttgtaact ttgaaataca aagtctaatg    3180
cataagcaga accgaaaagc agaccgacaa ttggttaaca ataattctt ttttttttctt    3240 ttttgatgtg ttgagtctta tttttgtggg gtttttttct ctcttttttt ttaaatgact    3300
gaaattcact gaagaaaaat atgtgaagga ccttcactct gagatgttat atttttttttt    3360 aaaaataact ctgagtaggg gtaccactga atctgtacag agccgtacaa accgaagttc    3420
tgcctctgat gtactttgtg aatttgtttc tttgaatttt catttttcat ttagttttcc    3480
ttgcatacaa ataagcatat aaaatggcaa caaactgcac atgatttcac aaatattaaa    3540 atgtcttta aaaagtattg ccaaacagta atgttgattt ctagttattt attctgggaa    3600
tgtatagtat ttgaaaacag aaattggtac cttgcacaca tcatctgtaa actgttcagt    3660
ttaaaatact gtagataatt aaccaaggta gaatgacctt gtaatgtaac tgctcttggg    3720
caatattctc tgtacatatt agcgacaaca gattggattt tatgttgaca tttgtttggt    3780
tatagtgcaa tatatttgt atgcaaacag tttcaataaa gtttgatctt cctctgctaa    3840
attgatgttg atgcaatcct tacaatgatt gcttttaaaa ttttaagata ggaaagaaat    3900
ctatagaaag tgttctgtta caaaatgtaa ctgttaccat tggaaatttc acatgtcaaa    3960
ggaggttagc cgttatttac caactttcaa gaacgtaatc ttgttcaata aggtgaaata    4020
tcaatgattg gtacacagtc acaatgtacc gttaaaatat gcactaagtc tcttttttttt    4080 acaaaggctg aattcagcaa ggcgctaact tgcttaaatg tgaattacta acttctaaaa    4140
ctgtaatttg attcacatct tttcaaatgg agttggagtt gattcatatt acaatatttg    4200
tgtgcaaaat gtgtatgttt ttcagtttaa agtcatgttt ttaaaatctt attaaagttt    4260
caaaaatctg aagattgttt atcttatcta gatgtaaatt tttattaaaa agttgcactt    4320
```

```
atgaaaaagc aaaaaaaaaa aaaaaaaaaa a                               4351
```

<210> SEQ ID NO 7
<211> LENGTH: 4305
<212> TYPE: DNA
<213> ORGANISM: Artificial Sequence
<220> FEATURE:
<223> OTHER INFORMATION: Synthetic nucleotide

<400> SEQUENCE: 7

```
agtcagtcag gcgctgggga gcgtttcggt ttcacttccg gtgagggggcc gcgcctgaga      60
gggcgggcag tgaagcaaac ggacggcgag cgcgggcggt ggcagtgacg gcggcgccgc     120
tgccgggggg cgtgcggtaa cgcggcggcg gcggcggcg cgacggcggc tgggcctcaa      180
gcgcctgcag cccacctccc ggaggcgggc tccggcgcg aggacggacg agaagatgga      240
ggagctggtg gtggaagtgc ggggctccaa tggcgctttc tacaaggcat ttgtaaaaga     300
tgtccatgaa gattctataa cagttgcttt tgaaaacaac tggcaaccag agagacagat     360
tccattccat gatgtgagat cccaccacc tgtaggttat aataaagata taaacgaaag      420
tgatgaagtt gaggtttatt ccagagcaaa tgaaaagag ccttgctgtt ggtggttagc      480
taaagtgagg atgataaagg gtgagttta tgtgatagaa tatgcagcat gtgatgctac      540
gtataatgaa attgtcacaa ttgagcgtct acgatctgtt aatcccaaca aacctgctac      600
aaaagatact ttccataaga tcaagctgga ggtgccagaa gatttacgac aaatgtgtgc      660
caaagaatca gcacataagg attttaaaaa ggcagttggt gccttctctg taacttatga      720
tccagaaaat tatcagctgg taattttgtc catcaatgaa gtcacctcaa agcgagccca     780
catgttgatt gacatgcact ttcgaagtct gcgcaccaag ttgtctctta tactgagaaa      840
tgaagaagcc agtaaacaac tggagagttc aaggcagctt gcctcaagat ttcatgaaca      900
gtttatcgta cgagaagatc tgatgggttt agctattggt actcatggtg ctaatattca     960
gcaagctaga aaagtgcctg gcgtcactgc tattgattta gatgaggata cctgcacatt     1020
tcatatttat ggagaggatc aagatgcagt gaaaaaggct agaagctttc tggaatttgc     1080
tgaagatgtc atacaggttc cacgaaactt agtaggcaaa gtataggaa aaaatggaaa     1140
gctgattcaa gagatcgtgg acaagtcagg agttgtgagg gtgaggattg aggctgaaaa     1200
tgagaaaagt gtcccacaag aagaggaaat tatgccacca agttccctac cttccaataa     1260
ttcaagggtt ggacctaact cctctgaaga aaagaaacat ttagatacaa aggaaaacac     1320
ccatttttct caacctaaca gtacaaaagt ccagaggggt atggtaccat ttgttttgt      1380
gggaacaaaa gacagcatcg ctaatgccac tgttcttttg gattatcacc tgaactattt     1440
aaaggaagta gaccagttgc gtttggagag attacaaatt gatgagcagt tgcgacaaat     1500
tggagctagt tctagaccac caccaaatcg tacagataag gaaaaaggct atgtgactga     1560
tgatggtcaa ggaatgggtc gaggtagtag accttacaga ataggggggc acggcagacg     1620
cggtcctgga tatacttcag gaactaattc tgaagcatca aatgcttctg aaacagaatc     1680
tgaccacaga gacgaactca gtgattggtc attagctcca acagaggaag agagggagag     1740
cttcctgcgc agaggagacg gacggcggcg tggaggagga ggaagaggac aaggaggaag     1800
aggaagagga ggaggcttca aggaaacga cgatcattcc gaacagata atcgtccacg      1860
taatccaaga gaggctaaag gaagaacagc tgatggatcc ctgcagagtg cctccagtga     1920
agggagccgg ctgcgcacgg gtaaagatcg taaccagaag aaggaaaagc cagacagcgt     1980
agatgggctg caaccgctgg tgaatggagt accctaaata agctacataa ttccgaagtt     2040
```

```
atatttcctc taccatttcc gtaattctta ctccatttta gaaaactttg ttaggccaaa    2100
gacaaatagt aggcaagatg gcacagggca tgaagtgaac acaaattctg caaagaattt    2160
ttttgatatt ggcaataatc aacaatcttc cagatttgca caaaaagatc ttgaaatttg    2220
atgcataact tttaagtaca cttaacactt cagggcagga ttttacttTT atttttTAAA    2280
aatactaagc agtgatcttt attaactagg accatttTcc tgaattggac tatataactc    2340
agcagtatgt ttcagtcttt cggagtaaat cacatttgtg ataatcatac tagatctctg    2400
tcttcagtct catttaaagt cttcatgaaa tgctgtgcca tttcatgtcc tgtgtcagtt    2460
tatgttttgg tccactTTtc cagtatttta gtggaccctg aaatgtgtgt gatgtgacat    2520
ttgttatttt cattagcaaa aaaagagtt gtatgatctg tgccttttTT atatcttggc    2580
aggtaggaat attatatttg gatgcagagt tcagggaaga taagttggaa acactaaatg    2640
ttaaagatgt agcaaaccct gtcaaacatt agtactTTTT agaagaatgc atgctttcca    2700
tatttTTTTc cttacataaa catcagctta ggcagtataa aaaataggac ttgttTTTTg    2760
ttttTgtttt gttgcactga agtatgacaa atagtgttat tggaagggat gtgtaatttt    2820
tctgtataga caggagaaga aataactatc ttttcatttg ggagaggcta aagatgtttt    2880
cagctacttg caaatcttcc tggtcgaaag ttagtaggat atgcctgctc tttggcctga    2940
tgacgaattt caactttgaa acattttctt ttgtcctccc caaattttgt caagtttttt    3000
cattcatatt ttacattaaa gcttattttg gggagatatg aaggtcatct tcataaatac    3060
ataacaaccc tcaaaagtat ataggtactt tgtctgagaa acattgaaag caggttaaat    3120
gttttgtaac tttgaaatac aaagtctaat gcataagcag aaccgaaaag cagaccgaca    3180
attggttaac aaataattct ttttttTTTct ttttTgatgt gttgagtctt attTTTgtgg    3240
ggttTTTTTc tctctTTTTT tttaaatgac tgaaattcac tgaagaaaaa tatgtgaagg    3300
accttcactc tgagatgtta tatTTTTTTT taaaaataac tctgagtagg ggtaccactg    3360
aatctgtaca gagccgtaca aaccgaagtt ctgcctctga tgtactttgt gaatttgttt    3420
ctttgaattt tcattTTTca tttagtttTc cttgcataca aataagcata taaaatggca    3480
acaaactgca catgatttca caaatattaa aatgtcttTT aaaaagtatt gccaaacagt    3540
aatgttgatt tctagttatt tattctggga atgtatagta tttgaaaaca gaaattggta    3600
ccttgcacac atcatctgta aactgttcag tttaaaatac tgtagataat taaccaaggt    3660
agaatgacct tgtaatgtaa ctgctcttgg gcaatattct ctgtacatat tagcgacaac    3720
agattggatt ttatgttgac atttgtttgg ttatagtgca atatatTTtg tatgcaaaca    3780
gtTTcaataa agtttgatct tcctctgcta aattgatgtt gatgcaatcc ttacaatgat    3840
tgcttTTaaa atTTTaagat aggaaagaaa tctatagaaa gtgttctgtt acaaaatgta    3900
actgttacca ttggaaattt cacatgtcaa aggaggttag ccgttattTa ccaactTTca    3960
agaacgtaat cttgttcaat aaggtgaaat atcaatgatt ggtacacagt cacaatgtac    4020
cgttaaaata tgcactaagt ctcttttttT tacaaaggct gaattcagca aggcgctaac    4080
ttgcttaaat gtgaattact aacttctaaa actgtaatTT gattcacatc TTTTcaaatg    4140
gagttggagt tgattcatat tacaatattt gtgtgcaaaa tgtgtatgtt tttcagttTa    4200
aagtcatgtt tttaaaatct tattaaagtt tcaaaaatct gaagattgtt tatcTTatct    4260
agatgtaaat tTTtattaaa aagttgcact tatgaaaaag caaaa                   4305
```

<210> SEQ ID NO 8

<211> LENGTH: 4426
<212> TYPE: DNA
<213> ORGANISM: Artificial Sequence
<220> FEATURE:
<223> OTHER INFORMATION: Synthetic nucleotide

<400> SEQUENCE: 8

```
gtttgactgt tacaggagg cgcagcggag cccttggcct cagtcagtca ggcgctgggg      60
agcgtttcgg tttcacttcc ggtgaggggc cgcgcctgag agggcgggca gtgaagcaaa     120
cggacggcga gcgcgggcgg tggcagtgac ggcggcgccg ctgccggggg gcgtgcggta     180
acgcggcggc ggcggcggcg cgacggcggc ctgggcctca agcgcctgca gcccacctcc     240
cggaggcggg ctcccggcgc gaggacggac gagaagatgg aggagctggt ggtggaagtg     300
cggggctcca atggcgcttt ctacaaggca tttgtaaaag atgtccatga agattctata     360
acagttgctt ttgaaaacaa ctggcaacca gagagacaga ttccattcca tgatgtgaga     420
ttcccaccac ctgtaggtta ataaaagat ataaacgaaa gtgatgaagt tgaggtttat      480
tccagagcaa atgaaaaaga gccttgctgt tggtggttag ctaaagtgag gatgataaag     540
ggtgagtttt atgtgataga atatgcagca tgtgatgcta cgtataatga aattgtcaca     600
attgagcgtc tacgatctgt taatcccaac aaacctgcta caaagatac tttccataag      660
atcaagctgg aggtgccaga agatttacga caaatgtgtg ccaaagaatc agcacataag     720
gattttaaaa aggcagttgg tgccttctct gtaacttatg atccagaaaa ttatcagctg     780
gtaattttgt ccatcaatga agtcacctca aagcgagccc acatgttgat tgacatgcac     840
tttcgaagtc tgcgcaccaa gttgtctctt atactgagaa atgaagaagc cagtaaacaa     900
ctggagagtt caaggcagct tgcctcaaga tttcatgaac agtttatcgt acgagaagat     960
ctgatgggtt tagctattgg tactcatggt gctaatattc agcaagctag aaaagtgcct    1020
ggcgtcactg ctattgattt agatgaggat acctgcacat tcatattta tggagaggat    1080
caagatgcag tgaaaaaggc tagaagcttt ctggaatttg ctgaagatgt catacaggtt    1140
ccacgaaact agtaggcaa agtaatagga aaaatggaa agctgattca agagatcgtg    1200
gacaagtcag gagttgtgag ggtgaggatt gaggctgaaa atgagaaaag tgtcccacaa     1260
gaagaggaaa ttatgccacc aagttcccta ccttccaata attcaagggt tggacctaac    1320
tcctctgaag aaaagaaaca tttagataca aaggaaaaca cccattttc tcaacctaac     1380
agtacaaaag tccagagggt gttagtggtt tcatcaattg tagcaggggg accccagaaa     1440
cctgaaccca aggcttggca gggtatggta ccatttgttt ttgtgggaac aaaagacagc     1500
atcgctaatg ccactgttct tttggattat cacctgaact atttaaagga agtagaccag    1560
ttgcgtttgg agagattaca aattgatgag cagttgcgac aaattggagc tagttctaga    1620
ccaccaccaa atcgtacaga taggaaaaa ggctatgtga ctgatgatgg tcaaggaatg     1680
ggtcgaggta gtagacctta cagaaatagg gggcacggca gacgcggtcc tggatatact    1740
tcaggaacta attctgaagc atcaaatgct tctgaaacag aatctgacca cagagacgaa    1800
ctcagtgatt ggtcattagc tccaacagag gaagagaggg gagcttcct gcgcagagga    1860
gacggacggc ggcgtggagg aggaggaaga ggacaaggag gaagaggaag aggaggaggc    1920
ttcaaaggaa acgacgatca ttcccgaaca gataatcgtc cacgtaatcc aagagaggct    1980
aaaggaagaa cagctgatgg atccctgcag agtgcctcca gtgaagggag ccggctgcgc    2040
acgggtaaag atcgtaacca aagaaggaa aagccagaca gcgtagatgg gctgcaaccg    2100
ctggtgaatg gagtacccta aataagctac ataattccga agttatattt cctctaccat    2160
```

-continued

```
ttccgtaatt cttactccat tttagaaaac tttgttaggc caaagacaaa tagtaggcaa    2220
gatggcacag ggcatgaagt gaacacaaat tctgcaaaga atttttttga tattggcaat    2280
aatcaacaat cttccagatt tgcacaaaaa gatcttgaaa tttgatgcat aacttttaag    2340
tacacttaac acttcagggc aggattttac ttttatttttt taaaaatact aagcagtgat   2400
ctttattaac taggaccatt ttcctgaatt ggactatata actcagcagt atgtttcagt    2460
ctttcggagt aaatcacatt tgtgataatc atactagatc tctgtcttca gtctcattta    2520
aagtcttcat gaaatgctgt gccatttcat gtcctgtgtc agtttatgtt ttggtccact    2580
tttccagtat tttagtggac cctgaaatgt gtgtgatgtg acatttgtta ttttcattag    2640
caaaaaaaag agttgtatga tctgtgcctt ttttatatct tggcaggtag aatattata    2700 tttgatgcaa gagttcaggg aagataagtt ggaaacacta atgttaaag atgtagcaaa     2760 ccctgtcaaa cattagtact ttttagaaga atgcatgctt tccatatttt tttccttaca    2820
taaacatcag cttaggcagt ataaaaaata ggacttgttt tttgttttttg ttttgttgca   2880 ctgaagtatg acaaatagtg ttattggaag ggatgtgtaa ttttttctgta tagacaggag   2940 aagaaataac tatcttttca tttgggagag gctaaagatg ttttcagcta cttgcaaatc    3000
ttcctggtcg aaagttagta ggatatgcct gctctttggc ctgatgacga atttcaactt    3060
tgaaacattt tcttttgtcc tccccaaatt ttgtcaagtt ttttcattca tattttacat    3120
taaagcttat tttggggaga tatgaaggtc atcttcataa atacataaca accctcaaaa    3180
gtatataggt actttgtctg agaaacattg aaagcaggtt aaatgttttg taactttgaa    3240
atacaaagtc taatgcataa gcagaaccga aaagcagacc gacaattggt taacaaataa    3300 ttctttttttt ttctttttttg atgtgttgag tcttatttttt gtgggttttt ttctctctt  3360 ttttttttaaa tgactgaaat tcactgaaga aaaatatgtg aaggaccttc actctgagat   3420
gttatatttt ttttttaaaaa taactctgag taggggtacc actgaatctg tacagagccg   3480
tacaaaccga agttctgcct ctgatgtact ttgtgaattt gtttctttga attttcattt    3540
ttcatttagt tttccttgca tacaaataag catataaaat ggcaacaaac tgcacatgat    3600
ttcacaaata ttaaaatgtc ttttaaaaag tattgccaaa cagtaatgtt gatttctagt    3660
tatttattct gggaatgtat agtatttgaa aacagaaatt ggtaccttgc acacatcatc    3720
tgtaaactgt tcagttttaaa atactgtaga taattaacca aggtagaatg accttgtaat   3780
gtaactgctc ttgggcaata ttctctgtac atattagcga caacagattg gattttatgt    3840
tgacatttgt ttggttatag tgcaatatat tttgtatgca aacagtttca ataaagtttg    3900
atcttcctct gctaaattga tgttgatgca atccttacaa tgattgcttt taaaatttta    3960
agataggaaa gaaatctata gaaagtgttc tgttacaaaa tgtaactgtt accattggaa    4020
atttcacatg tcaaggagg ttagccgtta tttaccaact ttcaagaacg taatcttgtt     4080
caataaggtg aaatatcaat gattggtaca cagtcacaat gtaccgttaa aatatgcact    4140
aagtctcttt ttttttacaaa ggctgaattc agcaaggcgc taacttgctt aaatgtgaat   4200
tactaacttc taaaactgta atttgattca catcttttca aatggagttg gagttgattc    4260
atattacaat atttgtgtgc aaaatgtgta tgttttcag tttaaagtca tgttttaaa     4320 atcttattaa agtttcaaaa atctgaagat tgtttatctt atctagatgt aaattttat     4380 taaaagttg cacttatgaa aaagcaaaaa aaaaaaaaaa aaaaaa                    4426
```

<210> SEQ ID NO 9

<211> LENGTH: 19
<212> TYPE: DNA
<213> ORGANISM: Artificial Sequence
<220> FEATURE:
<223> OTHER INFORMATION: Synthetic nucleotide

<400> SEQUENCE: 9
uaaggcuaug aagagauac                                                    19

<210> SEQ ID NO 10
<211> LENGTH: 19
<212> TYPE: DNA
<213> ORGANISM: Artificial Sequence
<220> FEATURE:
<223> OTHER INFORMATION: Synthetic nucleotide

<400> SEQUENCE: 10
auaagagaca acuuggugc                                                    19

<210> SEQ ID NO 11
<211> LENGTH: 19
<212> TYPE: DNA
<213> ORGANISM: Artificial Sequence
<220> FEATURE:
<223> OTHER INFORMATION: Synthetic nucleotide

<400> SEQUENCE: 11
uaacuucgga auuauguag                                                    19

<210> SEQ ID NO 12
<211> LENGTH: 20
<212> TYPE: DNA
<213> ORGANISM: Artificial Sequence
<220> FEATURE:
<223> OTHER INFORMATION: Synthetic nucleotide

<400> SEQUENCE: 12
gtggaagtgc ggggctccaa                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic nucleotide

<400> SEQUENCE: 13
gagctggtgg tggaagtgcg                                                   20

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Gly Arg Lys Lys Arg Arg Gln Arg Arg Arg
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Sythetic peptide

```
<400> SEQUENCE: 15

Arg Arg Arg Arg Asn Arg Thr Arg Arg Asn Arg Arg Arg Val Arg
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: Sythetic peptide

<400> SEQUENCE: 16

Thr Arg Arg Gln Arg Thr Arg Arg Ala Arg Arg Asn Arg
1               5                   10

<210> SEQ ID NO 17
<211> LENGTH: 19
<212> TYPE: PRT
<213> ORGANISM: Artificial Sequence
<220> FEATURE:
<223> OTHER INFORMATION: Sythetic peptide

<400> SEQUENCE: 17

Lys Met Thr Arg Ala Gln Arg Arg Ala Ala Ala Arg Arg Asn Arg Trp
1               5                   10                  15

Thr Ala Arg
```